(12) United States Patent
Cowburn et al.

(10) Patent No.: US 10,912,634 B2
(45) Date of Patent: *Feb. 9, 2021

(54) AUGMENTED REALITY DENTAL DESIGN METHOD AND SYSTEM

(71) Applicant: Trispera Dental Inc., Calgary (CA)

(72) Inventors: George Cowburn, Calgary (CA); Steven Cowburn, Calgary (CA); Erin Lenore Derraugh, Calgary (CA)

(73) Assignee: Trispera Dental Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,461

(22) Filed: Nov. 15, 2018

(65) Prior Publication Data

US 2019/0083212 A1 Mar. 21, 2019

Related U.S. Application Data

(62) Division of application No. 15/120,348, filed as application No. PCT/CA2015/000101 on Feb. 20, 2015, now Pat. No. 10,166,091.

(Continued)

(51) Int. Cl.
*A61C 13/34* (2006.01)
*G16H 50/50* (2018.01)
(Continued)

(52) U.S. Cl.
CPC ............ *A61C 13/34* (2013.01); *A61C 9/0053* (2013.01); *A61C 9/0086* (2013.01);
(Continued)

(58) Field of Classification Search
CPC ........... G06K 9/00268; G06K 9/00228; G06K 9/00315; G06F 19/3437; G06F 3/015;
(Continued)

(56) References Cited

U.S. PATENT DOCUMENTS 4,235,594 A 11/1980 Schwartz
6,302,689 B1 10/2001 Mayo
(Continued)

FOREIGN PATENT DOCUMENTS

CN 102170841 A 8/2011
CN 102933171 A 2/2013
(Continued)

OTHER PUBLICATIONS

Burnett., "Clinical Rest and Closest Speech Positions in the Determination of Occlusal Vertical Dimension," Journal of Oral Rehabilitation, Aug. 2000, vol. 27 (8), pp. 714-719.
(Continued)

*Primary Examiner* — Phuc N Doan
(74) *Attorney, Agent, or Firm* — Jones Walker LLP

(57) ABSTRACT

A method and system for designing a dental appliance for an individual. A 3D model of the individual's features including a portion of their face and arches is displayed on a 3D display. The 3D model includes an augmented reality dental appliance. The 3D model can be manipulated by inputs detected by a motion sensor, a brain-computer interface, both, or other sensors. In response to gestures neural activity, or other inputs, the augmented reality dental appliance or other aspects of the 3D model are modified. The 3D model is updated in response to the modified dental appliance or other changes, and repositioned to provide an updated 3D model. The updated 3D model is displayed on the 3D display. This system and method facilitates modification of the augmented reality dental appliance and observation of the resulting aesthetic effects.

136 Claims, 40 Drawing Sheets

Related U.S. Application Data

(60) Provisional application No. 61/942,734, filed on Feb. 21, 2014, provisional application No. 62/075,665, filed on Nov. 5, 2014.

(51) Int. Cl.
*A61C 19/04* (2006.01)
*A61C 9/00* (2006.01)
*G06F 3/01* (2006.01)
*G02B 27/01* (2006.01)
*G06K 9/00* (2006.01)
*G06T 19/20* (2011.01)
*A61C 13/00* (2006.01)
*G02B 27/00* (2006.01)
*G06F 30/00* (2020.01)
*G06F 19/00* (2018.01)

(52) U.S. Cl.
CPC .......... *A61C 13/0004* (2013.01); *A61C 19/04* (2013.01); *G02B 27/017* (2013.01); *G06F 3/011* (2013.01); *G06F 3/013* (2013.01); *G06F 3/015* (2013.01); *G06F 3/017* (2013.01); *G06F 19/00* (2013.01); *G06K 9/00228* (2013.01); *G06K 9/00268* (2013.01); *G06K 9/00315* (2013.01); *G06T 19/20* (2013.01); *G16H 50/50* (2018.01); *G02B 27/0093* (2013.01); *G02B 2027/014* (2013.01); *G02B 2027/0138* (2013.01); *G02B 2027/0187* (2013.01); *G06F 30/00* (2020.01)

(58) Field of Classification Search
CPC .......... G06F 3/013; G06F 17/50; G06F 3/017; G06F 3/011; A61C 19/04; A61C 9/0086; A61C 13/34; A61C 9/0053; A61C 13/0004; G02B 27/0093; G02B 2027/0138; G02B 2027/014; G02B 2027/0187; G02B 27/017; G06T 19/20
See application file for complete search history.

(56) References Cited

U.S. PATENT DOCUMENTS

| | | | |
|---|---|---|---|
| 8,219,438 B1 | 7/2012 | Moon et al. | |
| 2002/0048741 A1 | 4/2002 | Jordan et al. | |
| 2005/0089822 A1 | 4/2005 | Geng et al. | |
| 2005/0271996 A1 | 12/2005 | Sporbert et al. | |
| 2006/0127839 A1 | 6/2006 | Sellmann | |
| 2009/0087817 A1 | 4/2009 | Jansen et al. | |
| 2009/0287332 A1 | 11/2009 | Adusumilli et al. | |
| 2009/0298017 A1 | 12/2009 | Boerjes et al. | |
| 2010/0138025 A1 | 6/2010 | Morton et al. | |
| 2011/0102549 A1 | 5/2011 | Takahashi et al. | |
| 2011/0205341 A1* | 8/2011 | Wilson | G06F 3/011 348/51 |
| 2011/0218426 A1 | 9/2011 | Shinjo et al. | |
| 2011/0244415 A1 | 10/2011 | Batesole | |
| 2012/0015316 A1 | 1/2012 | Sachdeva et al. | |
| 2012/0054018 A1 | 3/2012 | Pradeep et al. | |
| 2012/0077141 A1 | 3/2012 | Massad | |
| 2012/0088208 A1 | 4/2012 | Schulter et al. | |
| 2012/0095732 A1 | 4/2012 | Fisker et al. | |
| 2013/0085591 A1 | 4/2013 | Ertl | |
| 2013/0218530 A1* | 8/2013 | Deichmann | A61O 5/77 703/1 |
| 2013/0242262 A1 | 9/2013 | Lewis | |
| 2014/0372084 A1* | 12/2014 | Cowburn | A61C 19/05 703/1 |
| 2015/0111177 A1* | 4/2015 | Fisker | A61C 13/01 433/196 |
| 2015/0126845 A1 | 5/2015 | Jin et al. | |
| 2015/0134094 A1 | 5/2015 | Thompson et al. | |
| 2015/0301733 A1 | 10/2015 | Acevedo | |
| 2015/0327958 A1 | 11/2015 | Llop et al. | |
| 2016/0166362 A1 | 6/2016 | Nonboe et al. | |

FOREIGN PATENT DOCUMENTS

| | | |
|---|---|---|
| CN | 103079494 A | 5/2013 |
| CN | 103226658 A | 7/2013 |
| EP | 2011449 A1 | 1/2009 |
| EP | 2635232 A2 | 9/2013 |
| JP | H06269468 A | 9/1994 |
| JP | H09206319 A | 8/1997 |
| JP | H11101935 A | 4/1999 |
| JP | 2006513994 A | 4/2006 |
| JP | 2010516329 A | 5/2010 |
| JP | 2010142285 A | 7/2010 |
| JP | 2011510685 A | 4/2011 |
| JP | 2011516940 A | 5/2011 |
| JP | 2011517801 A | 6/2011 |
| JP | 2011177451 A | 9/2011 |
| JP | 2012016573 A | 1/2012 |
| JP | 2012089112 A | 5/2012 |
| KR | 20070061979 A | 6/2007 |
| WO | 0180761 A2 | 11/2001 |
| WO | 03037204 A1 | 5/2003 |
| WO | 2011112454 A1 | 9/2011 |
| WO | 2011120893 A1 | 10/2011 |
| WO | 2013071435 A1 | 5/2013 |
| WO | 2013120955 A1 | 8/2013 |

OTHER PUBLICATIONS

Chinese Patent Application No. 201480069065.X, Notice of Allowance dated Oct. 29, 2018—English Translation Available.
Fujimoto, "Physiological Research Concerning the Mechanics of Jaw Movement Regarding the Rest Position of the Lower Jaw", Journal of Japanese Stomatological Society, 1958, vol. 7 (1), pp. 1-7.
Jarabak et al., "An Electromyographic Analysis of Muscular Behavior in Mandibular Movements from Rest Position," The Journal of Prosthetic Dentistry, Sep. 1957, vol. 7 (5), pp. 682-710.
Motohashi, et al., "A 3D Computer-Aided Design System Applied to Diagnosis and Treatment Planning in Orthodontics and Orthognathic Surgery," The European Journal of Orthodontics, 1999, vol. 21 (3), pp. 263-274.
Nishinaka, "Influence of Muscle Fatigue and Occlusal Vertical Dimension on Power Spectral Distribution in Masticatory Muscle Electromyogram", The Journal of Hiroshima University Dental Society, Jun. 1995, vol. 27 (1), pp. 38-54.
Saini at al., "Craniofacial Pain: A Neurosurgical Outlook," Surgical Neurology International, 2011, vol. 2, pp. 4, 3 pages.
Translation of claims for WO 2011/023784 retreived from https://patentscope.wipo.int!search/en/detail.jsf?docId=W02011023784&recNum=1&tab=PCTCiaims&maxRec=&office=&prevFilter=&sortOption=&queryString= on May 26, 2017.
Translation of description for WO 2011/023784 retreived from https://patentscope.wipo.int!search/en/detail.jsf?docId=W02011023784&recNum=1&maxRec=&office=&prevFilter=&sortOption=&queryString=&tab=PCTDescription on May 26, 2017.
U.S. Appl. No. 15/120,348, Notice of Allowance dated Oct. 31, 2018.
U.S. Appl. No. 15/120,348, Notice of Allowance dated Sep. 17, 2018.
Zegan et al., "Three-Dimensional Analysis of Malocclusion and Orthodontic Treatment Simulation," E-Health and Bioengineering Conference (EHB), 2015, pp. 1-4.
Chinese Patent Application No. CN201580009848.3, Decision of Rejection dated Aug. 5, 2019—English Translation Available.
Australian Patent Application No. AU2015221370, Examination report dated Jun. 19, 2019.
Chan., "Applying the Neuromuscular Principles in TMD and Orthodontics," Journal of the American Orthodontic Society, 2004, pp. 20-29.

(56) References Cited

OTHER PUBLICATIONS

Chinese Patent Application No. 201580009848.3, Office Action dated Nov. 27, 2018—English Translation Not Available.
Excerpt from Dental Technicians Manual, for the Trubyte, The Dentists Supply Company of New York, 1956, 5 pages.
European Patent Application No. EP15751686.5, Communication pursuant to Article 94(3) EPC dated May 16, 2019.
Feldman et al., "Rest Vertical Dimension Determined by Electromyography With Biofeedback as Compared to Conventional Methods," Journal of Prosthetic Dentistry, Aug. 1978, vol. 40 (2), pp. 216-219.
Japanese Patent Application No. 2016-553583, Office Action dated Dec. 17, 2018—English Translation Not Available.
International Patent Application No. PCT/CA2015/000101, International Preliminary Report on Patentability dated Jun. 22, 2016.
International Patent Application No. PCT/CA2015/000101, International Search Report and Written Opinion dated Jun. 11, 2015.
Australian Patent Application No. AU2015221370, Examination report dated May 19, 2020.
Chinese Patent Application No. 201580009848.3, Notice of Allowance dated Apr. 30, 2020—English Translation Available.
Chinese Patent Application No. 201580009848.3, Office Action dated Dec. 31, 2019—English Translation Available.
Japanese Patent Application No. 2016-553583, Notice of Allowance dated Nov. 18, 2019—English Translation Available.

\* cited by examiner

ZOOM IN

INCREASE SELECTION SIZE

DECREASE SELECTION SIZE

AUGMENTED REALITY DENTAL DESIGN METHOD AND SYSTEM

CROSS REFERENCE TO RELATED APPLICATIONS

This application is a divisional of U.S. patent application Ser. No. 15/120,348, filed on Aug. 19, 2016, which is a 371 of PCT Application Serial No. PCT/CA2015/000101, filed Feb. 20, 2015, which claims the benefit of priority of U.S. Provisional Patent Application No. 61/942,734 filed Feb. 21, 2014, and U.S. Provisional Patent Application No. 62/075,665 filed Nov. 5, 2014, all of which are hereby incorporated by reference in their entirety.

FIELD

The present disclosure relates generally to design of dental appliances or restorations.

BACKGROUND

Currently, proposed dental appliances or restorations are visualized by either trying in a replica of the restoration in the mouth of a subject, or by including 2D images of the subject in dental designer software. Examples include Densply's TruRx software for denture designs (see also United States Publication No. 2010/0076581) and 2D image arrangement from 3Shape for use on individuals with teeth (see also United States Publication No. 2013/0218530).

Densply's TruRx method is a commercially-available solution for digital modeling of a subject. This method involves placing reference indicia on the face of the subject, positioning a mouth shield to cover at least cover a portion of a subject's teeth thereby creating a voided area in the following digital photograph of the subject's face. The software uses the reference indicia size in the photograph to compare dimensions of the subject's face. The voided area is identified in the software and the selected materials and structures for making the denture are superimposed on the voided area of the digital image so that a practitioner or the subject can see the results of what the subject may look like with the selected combination.

SUMMARY

Herein provided is a system which integrates 3D imaging, dental designer software, and a 3D display to display hypothetical dental restorations and options in real time, from any angle and perspective. The system senses inputs allowing a layperson individual to interact with a compound model of the individual's head and mouth and an augmented reality ("AR") dental appliance or restoration, by using inputs including one or more of movements and gestures, manipulation of a simple physical interface, or measurement of the individual's neural activity through a brain-computer interface ("BCI") (e.g., an electroencephalographic BCI, a magnetoencephalographic BCI, etc.). The 3D display and the responsiveness to intuitive hand gestures or BCI data of the 3D model facilitate use of this system by a layperson individual. The individual can select a variety of design options for the appliance such as tooth morphology, arrangement, and colour. The compound model is updated in response to the design options, allowing the appearance of a proposed dental appliance to be confirmed and changed. The system similarly provides a view of proposed dental restorations in a multitude of facial expressions, lighting conditions, etc. BCI data may also be compared against empirical data of the individual in various emotional or other involuntary states to assess the individual's preferences and provide a suggested dental appliance.

The primary driver in design of a denture or other dental appliance is providing a physiologically appropriate bite. Such a bite can be provided to an individual by a variety of combinations of replacement teeth. While remaining at an appropriate position, the bite can be composed of a variety of different combinations of shapes and sizes of teeth (particularly where both upper and lower dentition are being replaced by dentures or other appliances). The particular choice of dentition can have a significant impact on the aesthetic result (e.g. on the resulting smile, etc.). It is, therefore, desirable to provide a method and system which allow an individual to have meaningful input into the aesthetic presentation of a denture or other dental appliance based on the size, shape, and/or orientation of the dentition included on the appliance. It is an object of the present disclosure to obviate or mitigate at least one disadvantage of previous approaches to designing dentures.

In a first aspect, the present disclosure provides a method and system for designing a dental appliance for an individual. A 3D model of the individual's features including a portion of their face and arches is displayed on a 3D display. The 3D model includes an augmented reality dental appliance. The 3D model can be manipulated by inputs detected by a motion sensor, a brain-computer interface, both, or other sensors. In response to gestures neural activity, or other inputs, the augmented reality dental appliance or other aspects of the 3D model are modified. The 3D model is updated in response to the modified dental appliance or other changes, and repositioned to provide an updated 3D model. The updated 3D model is displayed on the 3D display. This system and method facilitates modification of the augmented reality dental appliance and observation of the resulting aesthetic effects.

In a further aspect, the present disclosure provides a method of designing a dental appliance for a subject individual including displaying a 3D model of the subject individual on a 3D display, the 3D model including a scanned feature comprising a dental arch of the subject individual, and a portion of a face of the subject individual and the arch for relating the arch to the face; and an augmented reality feature comprising a dental appliance for the subject individual; detecting an input with a sensor; modifying the dental appliance in response to the input to provide a modified dental appliance; repositioning the scanned feature in response to the modified dental appliance to provide a repositioned scanned feature; updating the 3D model in response to the modified dental appliance and the repositioned scanned feature to provide an updated 3D model; and displaying the updated 3D model on the 3D display.

In an embodiment, the input includes a voluntary input.

In an embodiment, the voluntary input includes a gesture-based input.

In an embodiment, the gesture-based input includes gripping a feature of the 3D model on the 3D display and manipulating the feature.

In an embodiment, gripping the feature includes gripping the feature with a hand.

In an embodiment, the feature includes dentition of the dental appliance.

In an embodiment, manipulating the feature includes changing angulation of the dentition.

In an embodiment, the gesture-based input originates from the subject individual.

In an embodiment, the gesture-based input originates from a non-subject individual.

In an embodiment, the input includes a voluntary input.

In an embodiment, the voluntary input includes a gesture-based input.

In an embodiment, the sensor includes a motion sensor.

In an embodiment, the voluntary input includes a neural activity input, and the sensor includes a brain-computer interface.

In an embodiment, the neural activity input includes a conceptualization of the modified dental appliance.

In an embodiment, the neural activity input includes a conceptualization of modifying the dental appliance.

In an embodiment, conceptualization of modifying the dental appliance includes conceptualizing gripping a feature of the 3D model on the display with a hand and manipulating the feature.

In an embodiment, the feature includes dentition of the dental appliance.

In an embodiment, manipulating the feature includes changing angulation of the dentition.

In an embodiment, the voluntary input includes a gesture-based input, and the sensor includes a motion sensor.

In an embodiment, the voluntary input includes a neural activity input, and the sensor includes a brain-computer interface.

In an embodiment, the neural activity input includes neural activity input from the subject individual.

In an embodiment, the neural activity input includes neural activity input from a non-subject individual.

In an embodiment, the input includes constraining at least a portion of the scanned feature to a target position, and the modified dental appliance includes a modified feature which facilitates the target position.

In an embodiment, the target position includes a selected maxillomandibular relationship.

In an embodiment, the selected maxillomandibular relationship is a rest position, and the dentition provides a freeway space of between 1 and 4 mm at the rest position.

In an embodiment, the selected maxillomandibular relationship is at a selected occlusal position, and the dentition provides occlusion at the selected maxillomandibular relationship.

In an embodiment, the modified feature includes dentition of the dental appliance.

In an embodiment, the method includes detecting an involuntary input with the sensor; modifying the dental appliance in response to the involuntary input to provide the modified dental appliance; repositioning the scanned feature in response to the modified dental appliance to provide the repositioned scanned feature; updating the 3D model in response to the modified dental appliance and the repositioned scanned feature to provide the updated 3D model; and displaying the updated 3D model on the 3D display.

In an embodiment, the involuntary input includes involuntary input from the subject individual.

In an embodiment, the involuntary input includes involuntary input from a non-subject individual.

In an embodiment, the involuntary input includes a neural activity input and the sensor includes a brain-computer interface.

In an embodiment, the involuntary input includes a change in a facial expression and the sensor includes an optical sensor.

In an embodiment, the method includes detecting an involuntary input with the sensor; correlating the involuntary input with a preference criterion and with the modified dental appliance to determine a preference of the individual; modifying the modified dental appliance to provide a suggested dental appliance correlated to the preference of the individual; repositioning the scanned feature in response to the suggested dental appliance to provide a suggested scanned feature; updating the 3D model in response to the suggested dental appliance and suggested scanned feature to provide a suggested 3D model; and displaying the suggested 3D model on the 3D display. In an embodiment In an embodiment, the preference criterion includes an emotional state of an individual.

In an embodiment, the preference criterion includes a voluntary input of an individual.

In an embodiment, the involuntary input includes involuntary input from the subject individual.

In an embodiment, the involuntary input includes involuntary input from a non-subject individual.

In an embodiment, the involuntary input includes a neural activity input and the sensor includes a brain-computer interface.

In an embodiment, the involuntary input includes a change a facial expression and the sensor includes an optical sensor.

In an embodiment, the involuntary input is in response to the updated 3D model.

In an embodiment, the 3D model includes a saved position, the saved position having a selected scanned feature of the face.

In an embodiment, the method includes repositioning the scanned feature to the saved position; updating the 3D model in response to the saved position and repositioned the scanned feature to provide a saved position 3D model; and displaying the saved position 3D model on the 3D display.

In an embodiment, the scanned feature includes external feature data of the face for additional detail on the face in the 3D model.

In an embodiment, the external feature data of the subject individual's face includes data for including substantially the entire face of the subject individual's face in the 3D model.

In an embodiment, the method includes acquiring data of the scanned feature.

In an embodiment, acquiring data of the scanned feature includes optically scanning the scanned feature.

In an embodiment, acquiring data of the scanned feature includes ultrasonographically scanning the scanned feature.

In an embodiment, acquiring data of the scanned feature includes acquiring additional data of the scanned feature in response to the input and updating the 3D model to include the additional data.

In an embodiment, acquiring additional data and updating the 3D model to include the additional data are each performed continuously and substantially in real-time.

In an embodiment, adoption of a facial expression by the individual results in updating the 3D model to include the additional data, and wherein the additional data includes external feature data of the individual adopting the facial expression.

In an embodiment, the input includes a neural activity input, and the sensor includes a brain-computer interface.

In an embodiment, acquiring data of the scanned features includes confirming that the subject individual is at a maxillomandibular relationship corresponding to a rest position for the individual and acquiring data of the face when the maxillomandibular relationship is at the rest position.

In an embodiment, confirming that the subject individual is at a maxillomandibular relationship corresponding to the rest position includes measuring jaw muscle activity of the individual to confirm a maxillomandibular relationship having a minimum energy usage.

In an embodiment, measuring the jaw muscle activity includes applying electromyography to the individual.

In an embodiment, confirming that the subject individual is at a maxillomandibular relationship corresponding to the rest position includes exhausting jaw muscles of the individual.

In an embodiment, exhausting jaw muscles of the individual includes applying transcutaneous electrical nerve stimulation to the jaw muscles.

In an embodiment, data for displaying the 3D model includes data of the face when the maxillomandibular relationship is at the rest position.

In a further aspect, the present disclosure provides a system for designing a dental appliance for a subject individual including a computer readable medium for storing a 3D model, the 3D model including a scanned feature including a dental arch of the subject individual and a portion of a face of the subject individual and the arch for relating the arch to the face, and an augmented reality feature including a dental appliance for the subject individual; a 3D display for displaying the 3D model; a sensor for detecting an input; a processor operatively connected with the computer readable medium for processing the 3D model, with the sensor for receiving the input, and with the 3D display for displaying the 3D model, the processor configured and adapted to: modify the dental appliance in response to the input to provide a modified dental appliance; reposition the scanned feature in response to the modified dental appliance to provide a repositioned scanned feature; update the 3D model in response to the modified dental appliance and the repositioned scanned feature to provide an updated 3D model; and display the updated 3D model on the 3D display In an embodiment, the sensor includes a motion sensor for detecting a gesture-based input on the 3D model.

In an embodiment, the sensor includes a brain-computer interface for detecting a neural activity-based input on the 3D model.

In an embodiment, the sensor includes a first input point for input from a first individual and a second input point for input from a second individual.

In an embodiment, the sensor includes an optical sensor for detecting a gesture-based input, a facial-expression-based input, or an ocular dilation-based input.

In an embodiment, the system includes a scanner in communication with the computer readable medium for acquiring data of the scanned feature.

In an embodiment, the scanner includes an intra-oral scanner for acquiring data of the dental arch.

In an embodiment, the scanner includes an extraoral scanner for acquiring data of the portion of the face of the subject individual.

In an embodiment, the scanner includes an optical scanner.

In an embodiment, the scanner includes an ultrasonographic scanner.

In an embodiment, the system includes a muscle activity sensor for measuring muscle activity of the individual's jaw.

In an embodiment, the muscle activity sensor includes an electromyography module.

In an embodiment, the processor is in operative communication with the scanner for causing the scanner to acquire data for modelling the scanned feature; and the muscle activity sensor is in communication with the processor for directing the scanner to acquire data for modelling the scanned feature when the muscle activity is at a selected value.

In an embodiment, the selected value is indicative of a rest position.

In a further aspect, the present disclosure provides a method of designing a dental appliance for a subject individual including: displaying a 3D model on a 3D display, the 3D model including: a scanned feature including a dental arch of the subject individual and a portion of a face of the subject individual and the arch for relating the arch to the face; and an augmented reality feature including a dental appliance for the subject individual; detecting an input with a motion sensor; modifying the dental appliance in response to the gesture-based input to provide a modified dental appliance; repositioning the scanned feature in response to the modified dental appliance; and updating the 3D model in response to the modified dental appliance and the repositioned scanned feature to provide an updated 3D model.

In an embodiment, the input includes a gesture-based input.

In a further aspect, the present disclosure provides a method of designing a dental appliance for a subject individual including: displaying a 3D model on a 3D display, the 3D model including: a scanned feature including a dental arch of the subject individual and a portion of a face of the subject individual and the arch for relating the arch to the face; and an augmented reality feature including a dental appliance for the subject individual; detecting an input with an optical sensor; modifying the dental appliance in response to the gesture-based input to provide a modified dental appliance; repositioning the scanned feature in response to the modified dental appliance; and updating the 3D model in response to the modified dental appliance and the repositioned scanned feature to provide an updated 3D model.

In an embodiment, the input includes a gesture-based input.

In an embodiment, detecting the input includes tracking eye movements.

In an embodiment, the input includes a facial expression.

In a further aspect, the present disclosure provides a method of designing a dental appliance for a subject individual including: displaying a 3D model on a 3D display, the 3D model including: a scanned feature including a dental arch of the subject individual and a portion of a face of the subject individual and the arch for relating the arch to the face; and an augmented reality feature including a dental appliance for the subject individual; detecting an input with a brain-computer interface; modifying the dental appliance in response to the neural activity-based input to provide a modified dental appliance; repositioning the scanned feature in response to the modified dental appliance; and updating the 3D model in response to the modified dental appliance and the repositioned scanned feature to provide an updated 3D model.

In a further aspect, the present disclosure provides a system for designing a dental appliance for a subject individual including: a computer readable medium having a 3D model stored thereon, the 3D model including a scanned feature including a dental arch of the subject individual and a portion of a face of the subject individual and the arch for relating the arch to the face, and an augmented reality feature including a dental appliance for the subject individual; a 3D display for displaying the 3D model; a motion sensor for detecting an input on the 3D model; a processor operatively connected with the computer readable medium for processing the 3D model, operatively connected with the motion sensor for receiving the gesture-based input, and with the 3D display for displaying the 3D model, the processor configured and adapted to: modify the dental appliance in response to the gesture-based input to provide a modified dental appliance; reposition the scanned feature in response to the modified dental appliance to provide a repositioned scanned feature; update the 3D model in response to the modified dental appliance and the repositioned scanned feature to provide an updated 3D model; and display the updated 3D model on the 3D display.

In a further aspect, the present disclosure provides a system for designing a dental appliance for a subject individual including: a computer readable medium having a 3D model stored thereon, the 3D model including a scanned feature including a dental arch of the subject individual and a portion of a face of the subject individual and the arch for relating the arch to the face, and an augmented reality feature including a dental appliance for the subject individual; a 3D display for displaying the 3D model; a brain-computer interface for detecting a neural activity-based input on the 3D model; a processor operatively connected with the computer readable medium for processing the 3D model, operatively connected with the brain-computer interface for receiving the neural activity-based input, and operatively connected with the 3D display for displaying the 3D model, the processor configured and adapted to: modify the dental appliance in response to the gesture-based input to provide a modified dental appliance; reposition the scanned feature in response to the modified dental appliance to provide a repositioned scanned feature; update the 3D model in response to the modified dental appliance and the repositioned scanned feature to provide an updated 3D model; and display the updated 3D model on the 3D display.

In a further aspect, the present disclosure provides a computer readable medium having instructions encoded thereon for: rendering a 3D model including a scanned feature and an augmented reality feature, the scanned feature including a dental arch of a subject individual and a portion of a face of the subject individual and the arch for relating the arch to the face, and the augmented reality feature including a dental appliance for the subject individual; detecting an input from a sensor; modifying the dental appliance in response to the input to provide a modified dental appliance; repositioning the scanned feature in response to the modified dental appliance to provide a repositioned scanned feature; updating the 3D model in response to the modified dental appliance and the repositioned scanned feature to provide an updated 3D model; and displaying the updated 3D model on a 3D display.

In an embodiment, the input includes a voluntary input.

In an embodiment, the voluntary input includes a gesture-based input.

In an embodiment, the gesture-based input includes gripping a feature of the 3D model on the 3D display and manipulating the feature.

In an embodiment, gripping the feature includes gripping the feature with a hand.

In an embodiment, the feature includes dentition of the dental appliance.

In an embodiment, manipulating the feature includes changing angulation of the dentition.

In an embodiment, the gesture-based input originates from a first individual.

In an embodiment, the gesture-based input originates from a first individual and a second individual.

In an embodiment, the sensor includes a motion sensor.

In an embodiment, the voluntary input includes a neural activity input, and the sensor includes a brain-computer interface.

In an embodiment, the neural activity input includes a conceptualization of the modified dental appliance.

In an embodiment, the neural activity input includes a conceptualization of modifying the dental appliance.

In an embodiment, conceptualization of modifying the dental appliance includes conceptualizing gripping a feature of the 3D model on the display with a hand and manipulating the feature.

In an embodiment, the feature includes dentition of the dental appliance.

In an embodiment, manipulating the feature includes changing angulation of the dentition.

In an embodiment, the voluntary input includes a gesture-based input, and the sensor includes a motion sensor.

In an embodiment, the neural activity input includes neural activity input from a first individual.

In an embodiment, the neural activity input includes neural activity input from a first individual and a second individual.

In an embodiment, the input includes constraining at least a portion of the scanned feature to a target position, and the modified dental appliance includes a modified feature which facilitates the target position.

In an embodiment, the target position includes a selected maxillomandibular relationship.

In an embodiment, the selected maxillomandibular relationship is at a rest position, and the dentition provides a freeway space of between 1 and 4 mm at the rest position.

In an embodiment, the selected maxillomandibular relationship is at a selected occlusal position, and the dentition provides occlusion at the selected maxillomandibular relationship.

In an embodiment, the modified feature includes dentition of the dental appliance.

In an embodiment, the instructions encoded thereon include detecting an involuntary input with the sensor; modifying the dental appliance in response to the involuntary input to provide the modified dental appliance; repositioning the scanned feature in response to the modified dental appliance to provide the repositioned scanned feature; updating the 3D model in response to the modified dental appliance and the repositioned scanned feature to provide the updated 3D model; and displaying the updated 3D model on the 3D display.

In an embodiment, the involuntary input includes involuntary input from a first individual.

In an embodiment, the involuntary input includes involuntary input from a first individual and a second individual.

In an embodiment, the involuntary input includes a neural activity input and the sensor includes a brain-computer interface.

In an embodiment, the involuntary input includes a change in a facial expression and the sensor includes an optical sensor.

In an embodiment, the instructions encoded thereon include detecting an involuntary input from a first individual with the sensor; correlating the involuntary input with a preference criterion and with the modified dental appliance to determine a preference of the first individual; modifying the modified dental appliance to provide a suggested dental appliance correlated to the preference of the first individual;

repositioning the scanned feature in response to the suggested dental appliance to provide a suggested scanned feature; updating the 3D model in response to the suggested dental appliance and suggested scanned feature to provide a suggested 3D model; and displaying the suggested 3D model on the 3D display.

In an embodiment, the preference criterion includes an emotional state of the first individual.

In an embodiment, the preference criterion includes a voluntary input of an individual.

In an embodiment, the involuntary input includes involuntary input from a second individual, and the preference criterion includes an emotional state of the second individual.

In an embodiment, the involuntary input includes a neural activity input and the sensor includes a brain-computer interface.

In an embodiment, the involuntary input includes a change a facial expression and the sensor includes an optical sensor.

In an embodiment, the involuntary input is in response to the updated 3D model.

In an embodiment, the 3D model includes a saved position, the saved position having a selected scanned feature of the face.

In an embodiment, the instructions encoded thereon include: repositioning the scanned feature to the saved position; updating the 3D model in response to the saved position and repositioned the scanned feature to provide a saved position 3D model; and displaying the saved position 3D model on the 3D display.

In an embodiment, the scanned feature includes external feature data of the face for additional detail on the face in the 3D model.

In an embodiment, the external feature data of the face includes data for including substantially the entire face in the 3D model.

In an embodiment, the instructions encoded thereon further including acquiring data of the scanned feature with a scanner.

In an embodiment, acquiring data of the scanned feature includes optically scanning the scanned feature.

In an embodiment, acquiring data of the scanned feature includes ultrasonographically scanning the scanned feature.

In an embodiment, acquiring data of the scanned feature includes acquiring additional data of the scanned feature in response to the input and updating the 3D model to include the additional data.

In an embodiment, acquiring additional data and updating the 3D model to include the additional data are each performed continuously and substantially in real-time.

In an embodiment, adoption of a facial expression by the individual results in updating the 3D model to include the additional data, and wherein the additional data includes external feature data of the individual adopting the facial expression.

In an embodiment, the input includes a neural activity input, and the sensor includes a brain-computer interface.

In an embodiment, acquiring data of the scanned features includes confirming that the subject individual is at a maxillomandibular relationship corresponding to a rest position for the individual and acquiring data of the face when the maxillomandibular relationship is at the rest position.

In an embodiment, confirming that the subject individual is at a maxillomandibular relationship corresponding to the rest position includes measuring jaw muscle activity of the individual to confirm a maxillomandibular relationship having a minimum energy usage.

In an embodiment, measuring the jaw muscle activity includes applying electromyography to the individual.

In an embodiment, confirming that the subject individual is at a maxillomandibular relationship corresponding to the rest position includes exhausting jaw muscles of the individual.

In an embodiment, exhausting jaw muscles of the individual includes applying transcutaneous electrical nerve stimulation to the jaw muscles.

In an embodiment, data for rendering the 3D model includes data of the face when the maxillomandibular relationship is at the rest position.

Other aspects and features of the present disclosure will become apparent to those ordinarily skilled in the art upon review of the following description of specific embodiments in conjunction with the accompanying figures

BRIEF DESCRIPTION OF THE DRAWINGS

Embodiments of the present disclosure will now be described, by way of example only, with reference to the attached figures, in which features sharing reference numerals with a common final two digits of a reference numeral correspond to corresponding features across multiple figures (e.g. the processor 12, 112, 212, 312, 412, 512, 612, 712, 812, 912, 1012, 1112, 1212, 1312, etc.).

DETAILED DESCRIPTION

Figure 1:
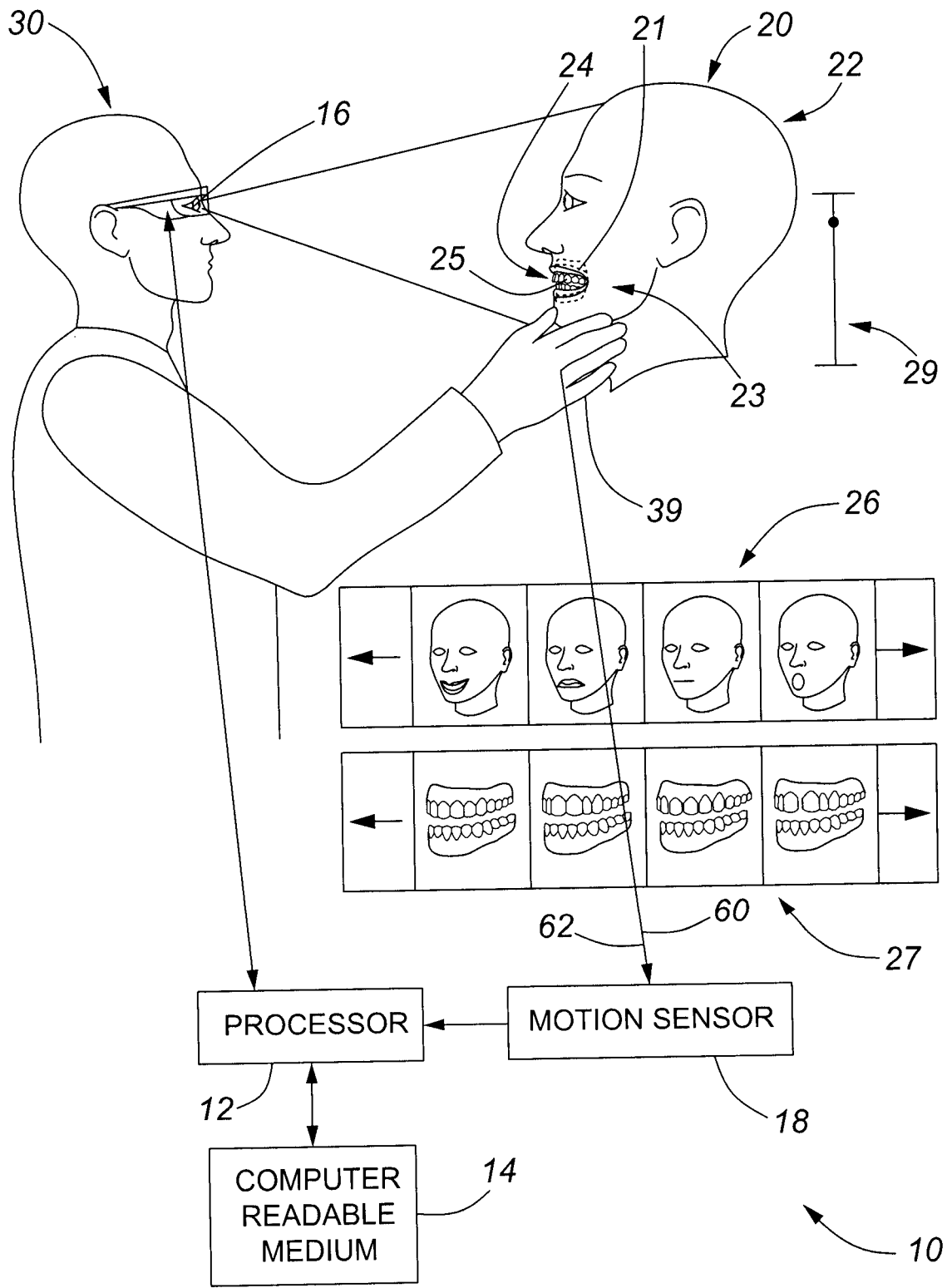
FIG. 1 is a schematic of a system for displaying and manipulating a 3D model of an edentulous individual.

Generally, the present disclosure provides a method and system for observing the aesthetic effect of changes in dentition of a dental appliance or restoration during design of the appliance or restoration.

Current practice in the dental field is for a professional to assess an individual's dental condition, and to recommend treatments if required. In aesthetic dentistry, a dental professional would present treatments which require an appliance to an individual. Design of the appliance is primarily the responsibility of the dental professional and the dental lab, with minimal input from the individual. Expensive mock ups or try-ins can be made from moldable materials by time-consuming procedures. For this reason, if a presented try-in or mock up is not desirable, it is rare to create more than a few mockups until one is decided on. The individual may desire an alternative, but as they are not skilled dental lab technicians, they may not be able to fully communicate their desires and a "doctor knows best" mentality commonly leaves the individual with a compromise result, not fully achieving their initial desires. Empowering the individual to design their own restoration is not a practical alternative as the education necessary to design a dental restoration is significant.

A person skilled in designing dental restorations on current modeling software typically requires days of training to correctly use and understand design software before becoming proficient. It is impractical to train a layperson individual who requires a dental appliance on such dental design software. Therefore a system which allows an average individual the ability to interact with dental design software immediately and intuitively observe aesthetic results from changes in a proposed appliance would be desirable.

An individual for whom a dental appliance is being designed is typically interested in having input into their resulting appearance with the appliance. When preparing an appliance, preliminary models are often prepared by moulding and casting, which is time consuming, expensive, and imprecise. Predicting the effects of a particular change on the resulting smile of the individual and effectively communicating the prediction is challenging. As a result, it is challenging to provide meaningful input to the individual as to their resulting appearance. Given the impact on the individual's appearance of their dentition, satisfaction as to resulting appearance is vital to positive treatment results.

A method which allows the individual to observe and evaluate a proposed appliance prior to the costly fabrication of try-ins or final prostheses would be advantageous over current methods of treatment visualisation. Many current systems rely on software which overlays 2D images on a 3D model. Such software is often specialized, difficult for most laypeople to use and understand, and is not directed to real-time use with a layperson individual. Manipulation of dentition in such software is done by rotating, tilting, and otherwise changing the position and angulation of individual teeth or groups of teeth to change the features of the appliance without affecting the resulting bite. In addition, the dentition can be switched out with other pre-modeled dentition. The present disclosure provides methods and systems which include real-time augmented reality ("AR") integrated with 3D modeling, dental design software, 3D display, and sensors. The sensors may include a motion sensor or motion capture device (e.g. an optical motion sensor, eye tracking sensors such as the SMI Eye Tracking Glasses 2 Wireless system, hand-based motion capture devices such as CyberGlove systems, etc.) for receiving inputs based on gestures (e.g. tracking hand gestures, tracking eye movements, etc.), other optical sensors, a brain-computer interface ("BCI") for receiving inputs based on neural activity, sensors for measuring pulse, temperature, or perspiration, or combinations of multiple tests used as a polygraph, or any other appropriate sensor. Hand-based sensors may also provide tactile feedback to simulate handling of a corporeal 3D model.

A 3D model of a portion of the individual's head is used in the methods and systems described herein. The 3D model includes empirical data of the individual's arches and of the individual's head which relates the arches to the head (e.g. data from a 3D intra-oral optical scanner for the arches and data from a 3D extraoral optical scanner for the arch and head together). The 3D model is displayed in three dimensions (e.g. by visualization through an Oculus Rift virtual reality headset, a Google Glass device, a holographic projection, etc.). In addition to the portions based on empirical data, the 3D model includes an augmented reality dental appliance. Both the individual's head and the augmented reality dental appliance can be manipulated by the individual through use of the individual's hands or other gestures, or through a BCI. Motion sensors detect the movement of the individual's hands or other gestures to receive an input, or the BCI receives input. The 3D model is manipulated based on the input. Features of the appliance (e.g. teeth, festoons and other features of gums in a denture, etc.) shown on the 3D model can be grasped and manipulated, or the individual can imagine doing so in the case of BCI. In addition, well-known hand gestures can be used or imagined for rotation, zooming, and other common functions. Combining eye tracking and a BCI may allow real time synchronizing of data from both systems with a common time stamp to correlate patterns of attention with emotional states.

Changes to the augmented reality dental appliance can be made in real-time on the 3D model by the individual, or another user of the system (e.g. a health care practitioner or a trusted layperson assisting the individual). The individual can then view the model from any angle and at varying zoom angles to observe the aesthetic result of the specific sizes, shapes, and orientation of the teeth in the appliance. Through manipulation and modification of the augmented reality dental appliance and the 3D model more broadly, the individual may provide meaningful input into the aesthetic result of changes to the particular design of the appliance. These manipulations may be accomplished through intuitive hand or other gestures. The gestures may be actual gestures (in the case or motion sensors or BCI), or imagined gestures (in the case of BCI). Using a BCI, imagined hand movements can be deciphered and mental commands given to manipulate the 3D model. AR features and elements of the model can, for example, be pushed, pulled, rotated, enlarged, shrunk, etc. to the individual's tastes. Additionally, elements like colour and shade can likewise be changed using mental commands. The individual's involuntary responses to the 3D model (e.g. emotional responses, etc.) may be accounted for and the model automatically updated in response to the individual's involuntary responses. The involuntary responses may be measured by sensors which measure optical changes, neural activity (a BCI), pulse, temperature, perspiration, combinations of multiple tests used as a polygraph, or any other appropriate indicator of an emotional state.

Interacting with the proposed appliance design is as simple as reaching out and moving a tooth or other feature of the model with the individual's hand, or where a BCI is used, imagining reaching and moving the feature or imagining the results of the change. As a result, only basic instruction to the individual is required. The design software includes preset functional limits on permissible changes to dentition to ensure that the resulting appliance has an appropriate bite with equal interdigitation, and allows an appropriate physiological rest position. The resulting appliance would be functional, but the aesthetics would be in the hands of the individual, subject to constraints imposed to ensure that the resulting dental appliance provides appropriate clearance between upper and lower dentition at rest, provides an appropriate maxillomandibular relationship at occlusion, and is otherwise optimized functionally. The aesthetic results of changes to the proposed appliance can be verified in real time, and the individual is able to find a design they are satisfied with. Alternatively, the individual may realize that their ideal design lies outside of functional limits, and therefore is not achievable. The individual could then manipulate the 3D model to prepare a suitable compromise between aesthetics and functionality. The 3D nature of the model and the display, including the ability to view from any angle and with varying levels of opacity, provides the individual with an understanding of how they will look in three dimensions with a proposed appliance.

The 3D model can also be updated to reflect different facial expressions. Smiles derived from old pictures of preexisting teeth can be input into the system to restore an individual's natural smile. Celebrity smiles can also be input to influence design options. The individual can express their desired design result without fear of judgment or criticism from dental professionals. Similarly, a second individual may participate and propose change to the appliance. The preset smile or other constrains may be set as aesthetic goals, and a dental appliance modeled to reach or approximate the goals while maintaining functional constraints related to a bite. Additional data may be acquired while manipulating the 3D model to provide empirical data at a given position, such as empirical data at an occlusal position with current dentures, of a smile, or of the individual at a physiological rest position ("rest position").

A 3D model prepared from empirical data acquired when the individual's maxillomandibular relationship is at the rest position provides an accurate representation of the individual's maxillomandibular relationship at the rest position (in contrast with acquiring data at a different position and extrapolating to the rest position). The individual's actual rest position determines that of the 3D model. The rest position of the 3D model thereby accounts for the interrelationship of all the entities within the stomatognathic system, including joints, muscles, nerves, gums, implants (if any), and teeth (if any), which affect the rest position. A 3D model prepared without any data of an individual at rest position is less likely to reliably distinguish a rest position from a habitual or other position.

The rest position is a position of the mandible in space relative to the maxilla (vertical, anterior-posterior, and lateral relative to the head in an upright postural position) along an isotonic path of mandibular closure. At the rest position, jaw musculature, including the extensor and depressor muscles that move the mandible, is postured at a position wherein it exerts a minimum of electrical activity. Expenditure of energy by the jaw musculature required to maintain the rest position is minimal compared to other positions along a path of mandible hinging. In the rest position, the individual's condyles are in a neutral, unrestrained position.

The rest position of an individual can be determined with reference to the individual. The rest position cannot be determined on a mechanical device that simulates mandibular movements, such as a dental articulator. A mandibular position, or maxillomandibular relationship, can be influenced by factors including postural problems of the head, neck cervical region, and back region. Internal derangements of the temporomandibular joint, emotional factors and systemic health factors of the individual can also contribute to a compromised mandibular position. It is generally beneficial to account for these factors before establishing a rest position. In some cases, failure to account for these factors results in an erroneous rest position. For example, a factor may have to be addressed or removed before establishing a rest position, which may be used to extrapolate to a bite registration. In another example, a factor may further complicate extrapolating rest position from other positions, increasing an advantage to acquisition of data of the individual at rest position.

A 3D model including empirical data at the rest position facilitates accurate determination of other potentially useful maxillomandibular relationships. For example, the 3D model may be applied to jaw tracking and extraoral bite assessment of individuals lacking sufficient dentition to establish a bite, for example edentulous individuals. The data may facilitate determination of a natural position at which centric occlusion ("CO"; which occurs when an individual's teeth are at maximum intercuspation, and the individual's jaw is at a "CO position") would occur if the individual had sufficient dentition to establish a bite. The data may thus facilitate approximation of an optimal neuromuscular CO position. An estimated CO position may be applied to preparing dentures for individuals who do not have enough teeth to define a bite.

It is common for a denturist or other dental professional to establish a CO position when preparing an appliance. Where the individual lacks sufficient dentition to establish the CO position, extrapolation is necessarily required to determine an appropriate maxillomandibular relationship in which CO should occur with an appliance. An edentulous individual will lack sufficient dentition to establish the CO position. Some partially dentate individuals will also lack sufficient dentition to establish CO, for example individuals with incisors but no molars.

Establishing a CO position based on the rest position when preparing an appliance may facilitate improvement and optimization of resulting dental function, stability, and harmony, of the stomatognathic system including the appliance. Establishing the CO position based on the rest position may also facilitate one or more of the following:

- optimization of the individual's occlusal scheme to a normal occlusal scheme where a normal occlusal scheme will provide appropriate functionality to the individual, or accounting for any jaw relationship classification or malocclusion where the individual's CO position may require as much;
- optimization of dental aesthetics (including tooth shape, contour, anatomy and morphology in both the anterior and posterior regions);
- optimization of facial cosmetics due to a more harmonious muscular balance when an optimal physiologic mandibular position is found; or
- mitigation of possible musculoskeletal occlusal signs and symptoms including: headaches, ear congestion feelings, ringing in the ears, pressure behind the eyes, teeth sensitivities, temporomandibular joint noise, masticatory muscle tenderness, neck and shoulder pain.

The rest position is a true rest position, in contrast with a habitual position. The habitual position is an acquired maxillomandibular position that may be anteriorly positioned along the condylar translation pathway. In a given individual, the rest position and the habitual position may coincide or be very close. However, the energy required by jaw musculature to maintain the habitual position is not necessarily a minimum as is the rest position. The habitual position is sometimes used as a starting point in determining a CO position in edentulous individuals. However, beginning with the habitual position may provide a less desirable outcome with respect to planning dental treatment than beginning with the rest position.

The 3D model is displayed by a 3D technique (e.g. Google Glass, Oculus Rift, Microsoft HoloLens, 3D television or monitor, holographic projection, etc.). Gestures used to manipulate the 3D model may be intuitive and simple (e.g. gripping a tooth with the individual's hand and rotating the tooth, etc.). As a result, the individual can easily manipulate the dentition of a proposed appliance to observe the aesthetic impact of a given choice of dentition. Performing similar manipulations on a two-dimensional display would require greater proficiency and abstraction. Using the 3D display makes fine and specific changes in the position of teeth accessible to the layperson individual, particularly where the individual is unaccustomed to three-dimensional visualization and manipulation on a two-dimensional display (which would be more common in the elderly, who are a major user of dentures and other dental appliances). Similarly, language barriers between the individual and a dental professional are not a bar to reviewing and manipulating the 3D model. This may have application when designing dentures for individuals in impoverished or inaccessible areas where multiple visits with a professional is impractical.

The hands-free nature of the manipulation means that infections are less likely to spread through contact with a tablet surface, keyboards, mouse, or other physical interface device.

A second individual may manipulate the 3D model, and where a BCI or other sensor which receives inputs of data indicative of emotional states is used, the emotional responses of the individual, the second individual, or both may be applied to predict the preferences of the individual, the second individual, or both. These preferences may be weighted to facilitate design of an appliance which both the individual and the second individual have a strong response to. The second individual may manipulate the 3D model in conjunction with the individual, or the second individual may do so without the participation or input of the individual (e.g. where the individual is unable to communicate or effectively choose for themselves, etc.).

Limitations of some previous methods result from the analysis being based on two integrated 2D images of the subject and teeth. The two images do not share common features and cannot be used for generation of a 3D model. The resulting compound image is not visible from any other angles. Also lighting conditions during the taking of the digital photograph may be inconsistent, and accurate representation of tooth shading in the representation to the subject's face, may not be fully accurate. Representation of the proposed prosthesis suffers from the lack of reference points between the existing denture or restoration and the subject's face. In addition, without a true 3D model, functional limits of design are more difficult to test and apply as constraints. As a result, non-functional designs may be to be modeled without indication of the potential problem. Finally, by placing a shield into a subject's mouth for a green screen, face and lip support which are changed, altering the resulting aesthetics which are to be modeled.

Previous green screen technology, such as the TruRx system, involves overlaying a projection of a proposed design on top of the individual's dental arches. In contrast, the 3D model used in the methods and systems disclosed herein relates arches to facial structures. In the event that the arches and teeth are completely obscured by the lip in a given position, the 3D model remains capable of accurately representing the proposed appliance and its effect on aesthetics.

A benefit of using a 3D model relates to the resting lip line. At the resting lip line, the lip is relaxed and the majority, often the entirety, of the teeth are not visible. By application of extraoral structures (e.g. facial features, etc.) in addition to intraoral features (e.g. the dentition proposed by the augmented reality), the 3D model provides an accurate depiction of the effects of teeth on the external features even when the arches and appliance are not visible.

System

FIG. 1 is a system 10 for displaying and manipulating a 3D model 20 of a subject individual 30. The system 10 includes a processor 12 and a computer readable medium 14. The 3D model 20 is rendered, manipulated, updated, and displayed through execution of instructions by the processor 12. The 3D model 20 is based on data maintained on the computer readable medium 14. The processor 12 and the computer readable medium 14 may be on the same or device or separate devices, may be at separate network locations, or any other suitable arrangement. The functions of the processor 12 and the computer readable medium 14 may be divided among multiple individual processors and computer readable media.

The system 10 includes a 3D display 16 in operative communication with the processor 12 for displaying the 3D model 20 such that the individual 30 can place their hands on the 3D model 20 to manipulate the 3D model 20 on the 3D display 16, for example through intuitive gestures. In FIG. 1, the individual 10 is manipulating the 3D model 20 with a hand 39. The system 10 may allow the individual to change the position or view of the 3D model 20, change selected features of the 3D model 20, or otherwise manipulate the 3D model 20 using gestures directed at the 3D model 20 as shown on the 3D display 16. The gestures may include gripping a portion of the 3D model 20 with a hand and applying similar hand gestures as would be used if manipulating a physical model. Examples of such manipulations may also include changing the view of the 3D model 20 shown on the display, such as rotating, panning, zooming in or out, changing the lighting conditions, etc.

The 3D display 16 is shown as an eyewear-style AR interface (e.g. Google Glass, Oculus Rift, Microsoft HoloLens, Meta Spaceglasses, etc.). Eyewear AR interfaces allow the 3D model 20 to display over the actual physical environment from the perspective of the individual 30. The 3D display 16 projects a compound environment, allowing the individual 30 to see the 3D model 20 in three dimensions and with real-time updates. The eyewear-style 3D display 16 is interchangeable with any display device that provides a perception to the individual 30 that the 3D model 20 is in front of their eyes and can be manipulated with their hands or other commands, and viewed from multiple angles.

The system 10 includes a motion sensor 18. The motion sensor 18 detects gestures of the individual 30 (e.g. movements of the hands, head, feet, etc.). The gestures result in inputs of first input data 60, which is provided to the processor 12. The first input data 60 includes voluntary action data 62 corresponding to gestures of the individual 30 detected by the motion sensor 18. The motion sensor 18 monitors the motion, location, position, and angle of the gestures of the individual 30, allowing the individual 30 to manipulate of the 3D model 20 on the 3D display 16. The motion sensor 18 may detect motion based on any suitable data (e.g. optical, Doppler radar, passive IR, tomographic, combinations thereof, etc.).

Other sensors may be included in the system 10 in addition to the motion sensor 18 or in place of the motion sensor 18 to allow the individual 30 to interact with the 3D model 20 and the dental design software otherwise than through gestures (e.g. by using eye movements, voice commands, facial expressions, etc.) (not shown) to provide the voluntary action data 62 that can be interpreted by the processor 12. Such sensors may be based on capture of optical data or other forms of data from the individual 30 (e.g. the optical sensor 1296 of FIG. 39, etc.).

Figure 30:
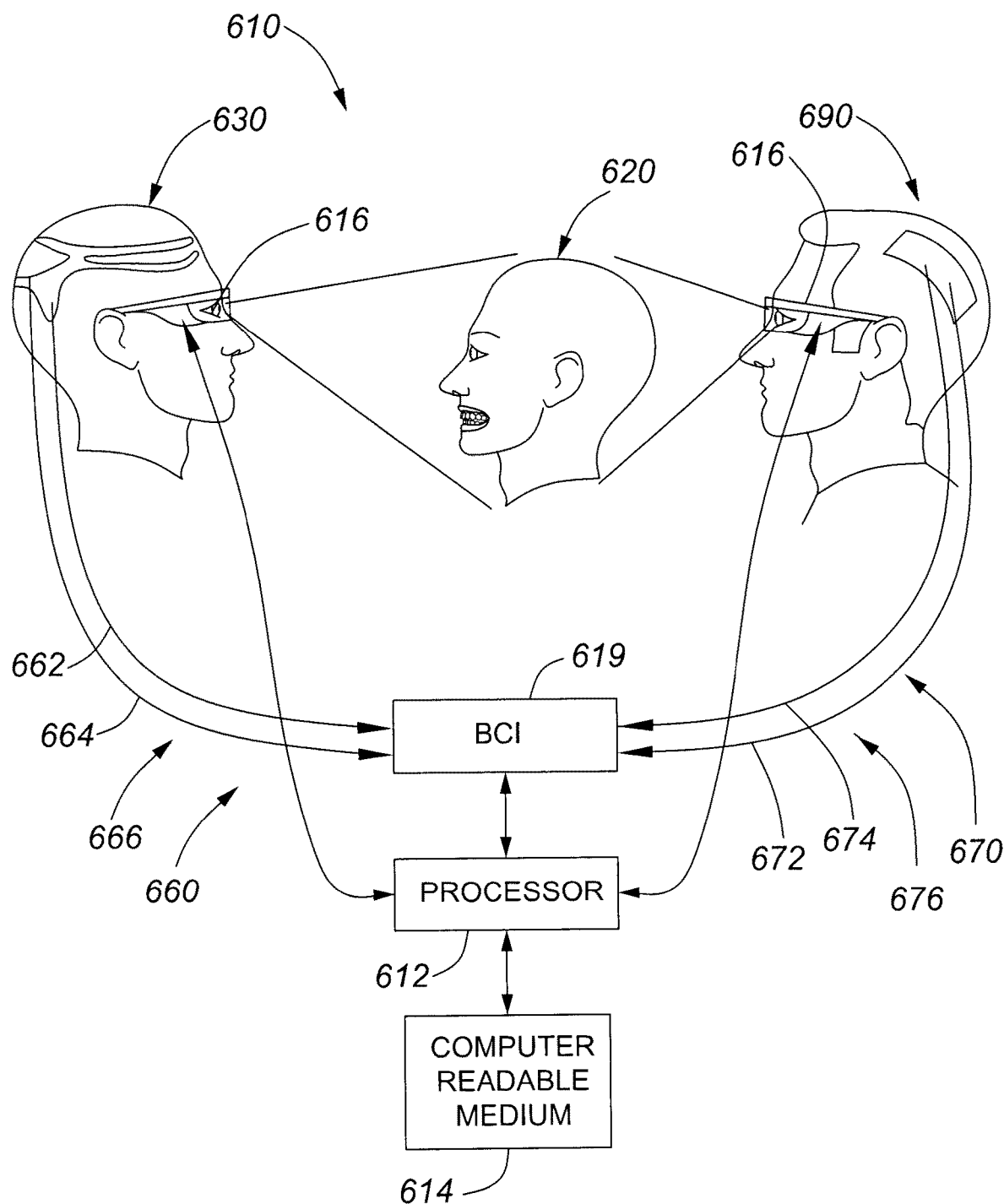
FIG. 30 is a schematic of a system for displaying and manipulating a 3D model of an edentulous individual.

The 3D model 20 may also be manipulated in response to voluntary action data from a person other than the individual 30 (e.g. the system 610 of FIG. 30, etc.).

Figure 2:
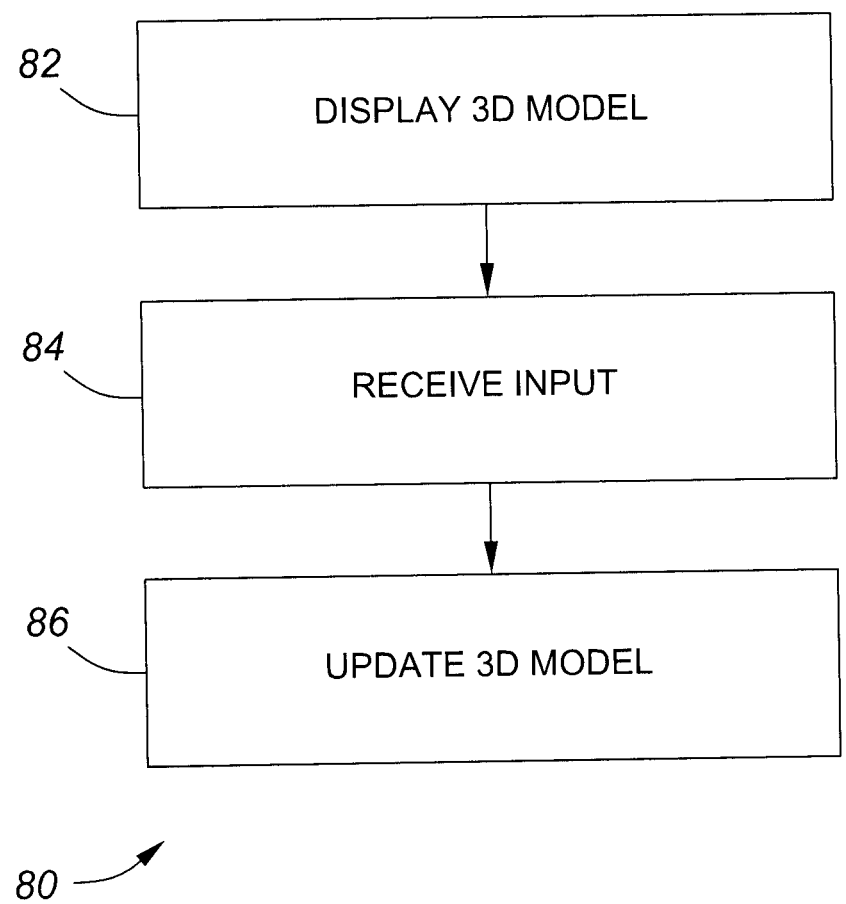
FIG. 2 is a flow chart of a method for displaying and manipulating the 3D model of FIG. 1.

FIG. 2 shows a method 80 of working with a 3D model. The method 80 includes displaying the 3D model 82, receiving an input 84, and updating the 3D model 86 in response to receiving an input 84. The method 80 may be performed using the system 10. Displaying the 3D model 82 and updating the 3D model 86 may be completed on the 3D display 16 by execution of instructions by the processor 12 using data stored in the computer readable medium 14. Receiving an input 84 may include detection of a hand gesture by the motion sensor 18 of the system 10, other voluntary inputs, involuntary inputs, or combinations of inputs.

Components of 3D Model

Figure 3:
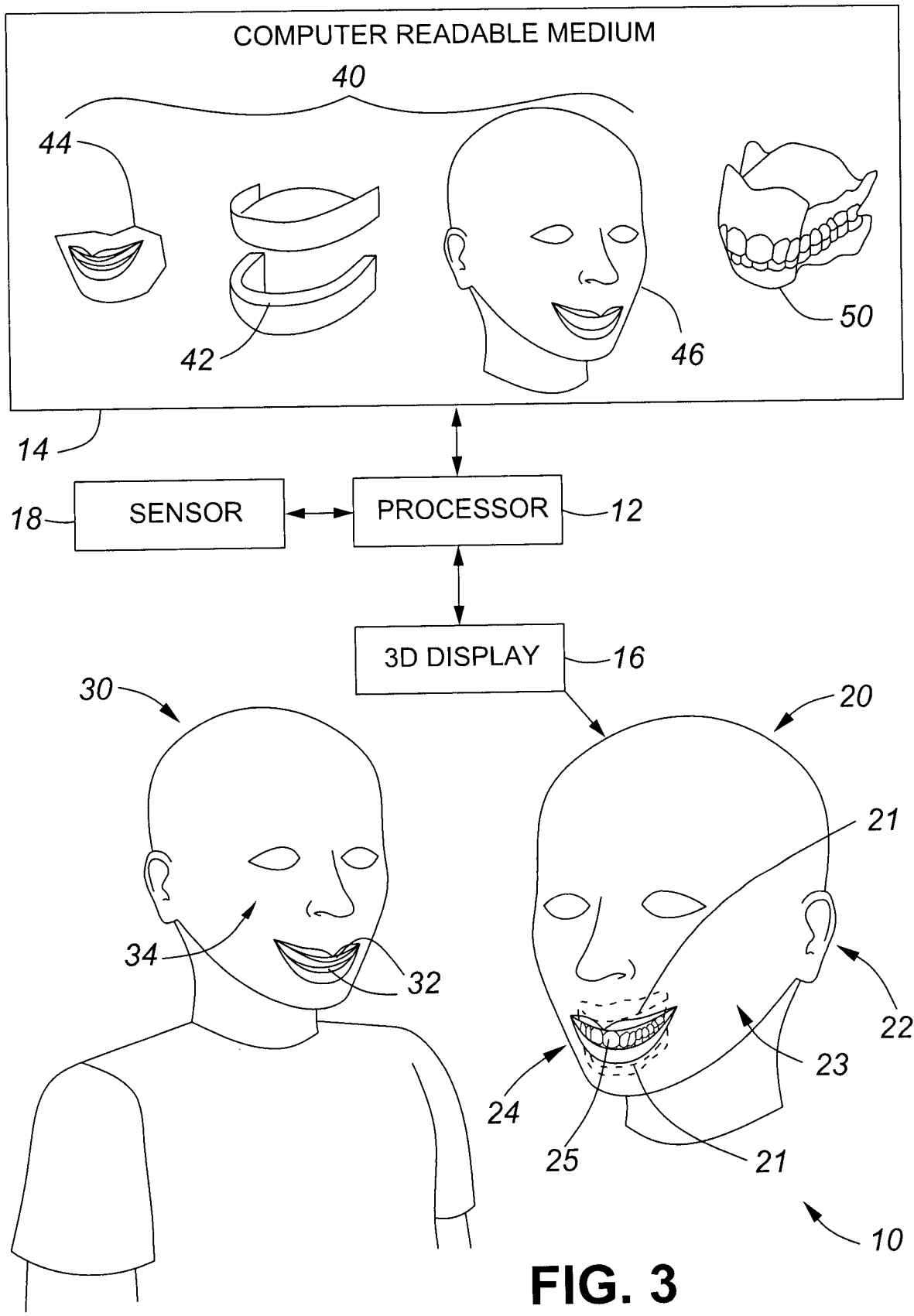
FIG. 3 is the individual of FIG. 1 viewing the 3D model of FIG. 1.

FIG. 3 shows the individual 30 viewing the 3D model 20. The 3D model 20 is modeled based on scanned features data 40 and augmented reality data 50. The 3D model 20 includes subject features 22 and a proposed dental appliance 24. The subject features 22 include modeled arches 21 and modeled external features 23. Unlike the 3D display 16 of FIG. 1, which applies an eyewear-based in interface, the 3D model 20 of FIG. 3 is shown as a three-dimensional projector (e.g. holographic projector, the TelePresence system by Musion Das Hologram Ltd., the Digital Lightfield system by Magic Leap, etc.) which functions in the absence of eyewear. Either of these types of displays, or any other suitable display, may be used as the 3D display 16.

The scanned features data 40 includes arches data 42, relational data 44, and external features data 46. The scanned features data 40 is empirical data, which is acquired for example by scanning arches 32 of the individual 30 with an intraoral optical scanner (e.g. acquired using the system 910 of FIG. 33, etc.) and external features 34 of the individual 30 with an extraoral optical scanner (e.g. acquired using the system 910 of FIG. 33, etc.). While additional scanned features data 40 may provide additional accuracy to the 3D model 20 for a given position, the 3D model 20 can be manipulated to many positions based only on initially-acquired scanned features data 40. Where the individual 30's appearance does not change much between sessions with the 3D model 20, the same scanned features data 40 may be applied across multiple sessions. The scanned features data 40 may be acquired from an optical scanner, ultrasound scanner, other suitable scanner, or other suitable data acquisition technique applied to the external features 34.

The arches data 42 facilitates modeling of the maxillary and mandibular dental arches 32 of the individual 30, providing the modeled arches 21.

The external features data 46 facilitates modelling portions of the individual 30's external features 34. The greater the amount of external features data 46, the more extensive are the modelled external features 23, with correspondingly more expansive observation of aesthetic effects on the external features face than a 3D model which lacks the additional external feature data (e.g. see the 3D model 120 in FIG. 16). Acquiring data similar to arches data 42, relational data 44, and external features data 46, and preparing a model based on types of data is further discussed in WO 2013/071435, which shares an inventor with this application. Features for acquiring data may be included, such as the extraoral scanners 992, 1092, 1192, or 1392 shown in FIGS. 33, 35, 38, and 40, respectively.

The relational data 44 includes data of the arches 32 and of the external features 34 (e.g. portions of the face, portions of the neck, etc.). The relational data 44 facilitates establishing a relationship between the arches 32, and between the external features 34 and the arches 32. The relative positions of the arches 32 define a maxillomandibular relationship. The relational data 44 allows the external features 34 to be modeled based on the relative positions of the arches 32 in addition to being modeled based on the dentition 25. The maxillomandibular relationship at occlusion for a given proposed dental appliance 24 contributes to the appearance of the modeled external features 23. Given a constraint on a particular maxillomandibular relationship at occlusion, the dentition 25 will drive the appearance of the modelled external features 23 at occlusion with the proposed dental appliance 24.

The relational data 44 also allows the maxillomandibular relationship of the 3D model 20 to be modeled based on the position of the external features 34. Constraints may be placed on how the modeled external features 23 are to look. The proposed dental appliance 24 will be modeled to result in the selected appearance of the modeled external features 23. Constraints would also be applied to the proposed dental appliance 24 to ensure that the maxillomandibular relationship at occlusion and at rest which the proposed dental appliance 24 results in are both appropriate for the individual 30. The modeled external features 23 selected for a resulting appearance may result from a position included in the external features data 46, or be substantially similar to a position included in the external features data 46. Empirical data of such a position may increase the effectiveness of the 3D model 20 in providing the proposed dental appliance 24 with dentition 25 and other features correctly selected for the individual 30. The rest position may be defined with empirical evidence, for example as discussed below and in WO 2013/071435, which shares an inventor with this application, the external features data 46 may include empirical data of the individual 30 at the rest position. The system 1310 includes features to facilitate acquiring empirical external features data 46 at the rest position.

The relational data 44 facilitates manipulation of the maxillomandibular relationship in the 3D model 20 while maintaining an accurate relationship between the two modeled arches 21, and between the modeled arches 21 and the modeled external features 23. The relationships are accurate in that the 3D model 20 conforms to relationships that are reflective of corresponding relationships in the individual 30 between the arches 32, and between the arches 32 and the external features 34.

The augmented reality data 50 includes a representation of the proposed dental appliance 24. The proposed dental appliance 24 shown is a pair of dentures. Other appliances may also be modelled (e.g. a single denture, a prosthetic, a restoration, etc.). The proposed dental appliance 24 is modeled based on the augmented reality data 50 and overlaid on the modeled arches 21. The proposed dental appliance 24 results in a maxillomandibular relationship between the modeled arches 21 at interdigitation facilitated by dentition 25 on the proposed dental appliance 24. The maxillomandibular relationship, and the resulting locations of the modeled arches 21 and the modeled external features 23, are informed by the scanned features data to represent in the 3D model 20 the effects of the maxillomandibular relationship between the arches 32 on the external features 34.

The proposed dental appliance 24 is based on a defined maxillomandibular relationship appropriate for the individual 30 (e.g. providing appropriate occlusal and rest positions, etc.) and condular angles which define movement direction from the bite position.

When modeling the proposed dental appliance 24 in real time with AR, a verification procedure may facilitate the 3D model 20 accurately modelling the proposed maxillomandibular relationship position to align with the observed movement of the individual 30. With no dental appliances worn, the individual moves their jaw (e.g. in a regular chewing function, etc.). The observed data can be compared to the 3D model 20 and if inconsistencies are discovered, the 3D model 20 can be corrected, with the maxillomandibular occlusion position or condular angles as useful landmarks when comparing the movement of the 3D model 20 to the observed movements of the individual 30. The verification procedure may be based on the external feature data 46. The verification procedure may also be based on additional external feature data 46 acquired using, for example, the system 910 (FIG. 33), the system 1010 (FIG. 35), the system 1110 (FIG. 37), the system 1310 (FIG. 40), etc.

Manipulation of 3D Model

The system 10 facilitates intuitive manipulation of the 3D model 20 by the individual 30, who may be a lay person. Manipulation may include changing perspective of the 3D model 20. Manipulation may include changing the position of the subject features 22, altering the proposed dental appliance 24, changing the underlying external feature data 46, or changing the underlying augmented reality data 50, to facilitate observing the resulting effects on the aesthetics of the 3D model 20, particularly with respect to the modeled external features 23. Constraints may be applied to the maxillomandibular position at occlusion, the spacing of the dentition 25 at the rest position, the appearance of the modeled external features 23, combinations of these features, or other appropriate features depending on the goals of designing the proposed dental appliance 24.

When applying constrains to the spacing of the dentition 25 at the rest position, a freeway space of between 1 and 4 mm may be defined, for example a freeway space of about 2 mm. The freeway space is the clearance between the dentition 25 on upper and lower portions of the proposed dental appliance at the rest position. Excessive or insufficient freeway space each distort facial appearances. Excessive freeway space ("over-closed") causes the mandible and lips to protrude and have a 'collapsed' or 'frowning' appearance. Insufficient freeway space ("over-opened") causes the face to elongate, this causes the lips to appear thinned and stretched out and the face has a general uncomfortable look. This is due to the strain of the facial muscles which cannot rest as they are engaged in an attempt to close to the proper dimension. If an individual presents in an over-opened or over-closed state, the present methods and systems could be used to determine how to change the maxillomandibular relationship to achieve a desired external appearance and an appropriate rest position and occlusal position.

Figure 4:
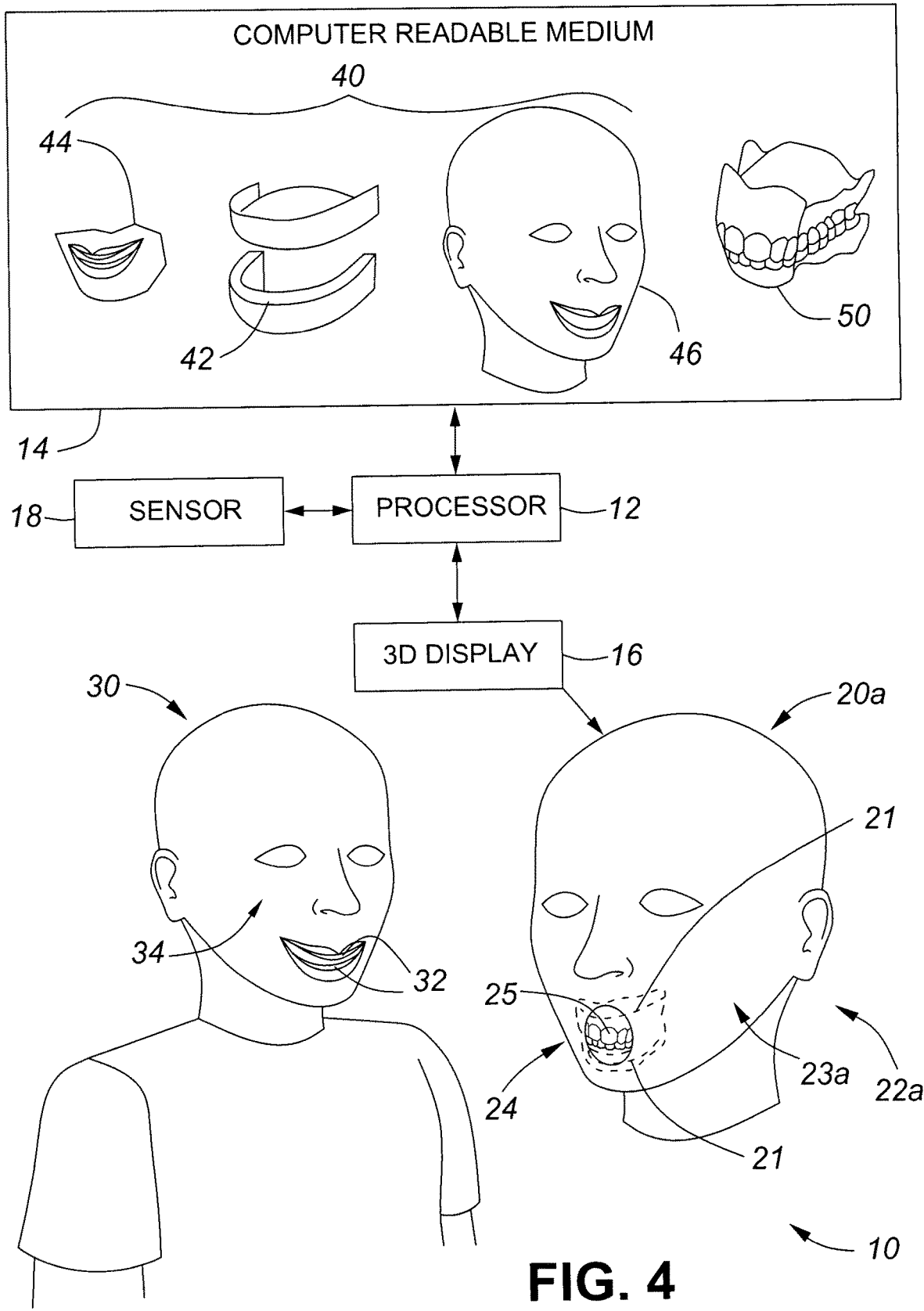
FIG. 4 is the 3D model of FIG. 1 after manipulation of the maxillomandibular relationship.

FIG. 4 shows an updated 3D model 20a having a different maxillomandibular relationship than the 3D model 20. The updated 3D model 20a results from manipulation of the subject features 22. The different maxillomandibular relationship may result in repositioning of the modeled external features 23, providing repositioned modeled external features 23a (and similarly, the subject features 22 are repositioned to repositioned subject features 22a). The maxillomandibular relationship of the 3D model 20 may be manipulated as a result of gestures or other input directed at the 3D model 20 as displayed on the 3D display 16 and detected by the motion sensor 18. Through application of the relational data 44, the positions of the modeled arches 21 relative to each other and to the modeled external features 23 may be updated in the 3D model 20 following a change in the maxillomandibular relationship to the updated 3D model 20a.

Figure 5:
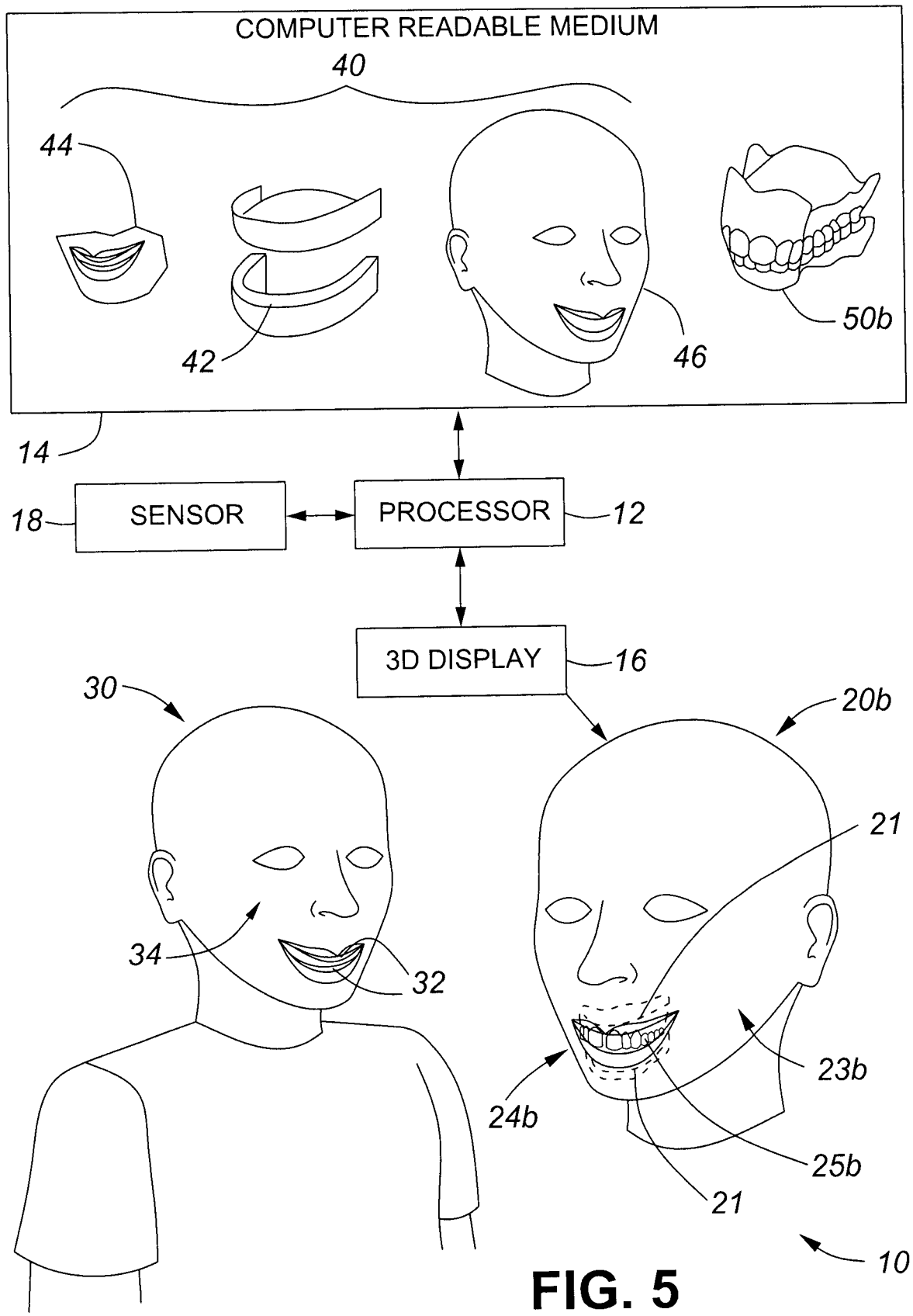
FIG. 5 is the 3D model of FIG. 1 after manipulation of a proposed dental appliance.

FIG. 5 shows an updated 3D model 20b including a modified dental appliance 24b resulting from manipulation of the proposed dental appliance 24 and modeled based on modified augmented reality data 50b. The modified dental appliance 24b may result in a different maxillomandibular relationship at occlusion than the proposed dental appliance 24. The different maxillomandibular relationship may result in repositioning of the modeled external features 23, providing repositioned modeled external features 23b (and similarly, the subject features 22 are repositioned to repositioned subject features 22b). In addition, the modified dental appliance 24b may have the same maxillomandibular relationship at occlusion as the proposed dental appliance 24, but may nonetheless result in differing positions and appearances of the modeled external features 23, providing the repositioned modeled external features 23b. The size, orientation, shape, colour tone, and any other appropriate features of the proposed dental appliance 24 and its components may also be updated to provide the modified dental appliance 24b. Structural changes to dentition 25 or other features of the proposed dental appliance 24 may have an effect on the subject features 22 in that the maxillomandibular relationship at the rest position, the occlusion position, or other selected reference points change following changes to the proposed dental appliance 24. The other features may include the interface between the proposed dental appliance 24 and the modeled arches 21 or other aspects of the proposed dental appliance 24 which determine how the proposed dental appliance 24 will sit on the modeled arches 21. The modeled external features 23 may also be manipulated to result in a new maxillomandibular relationship which provides or approximates the selected position of the modeled external features 23. Changes to the proposed dental appliance 24 may be constrained within preset limits defined by the individual 30 or a second individual (e.g. the second individual 690 in FIG. 30, etc.). Such constraints would typically be to provide a physiologically appropriate rest position or occlusion position.

Figure 6:
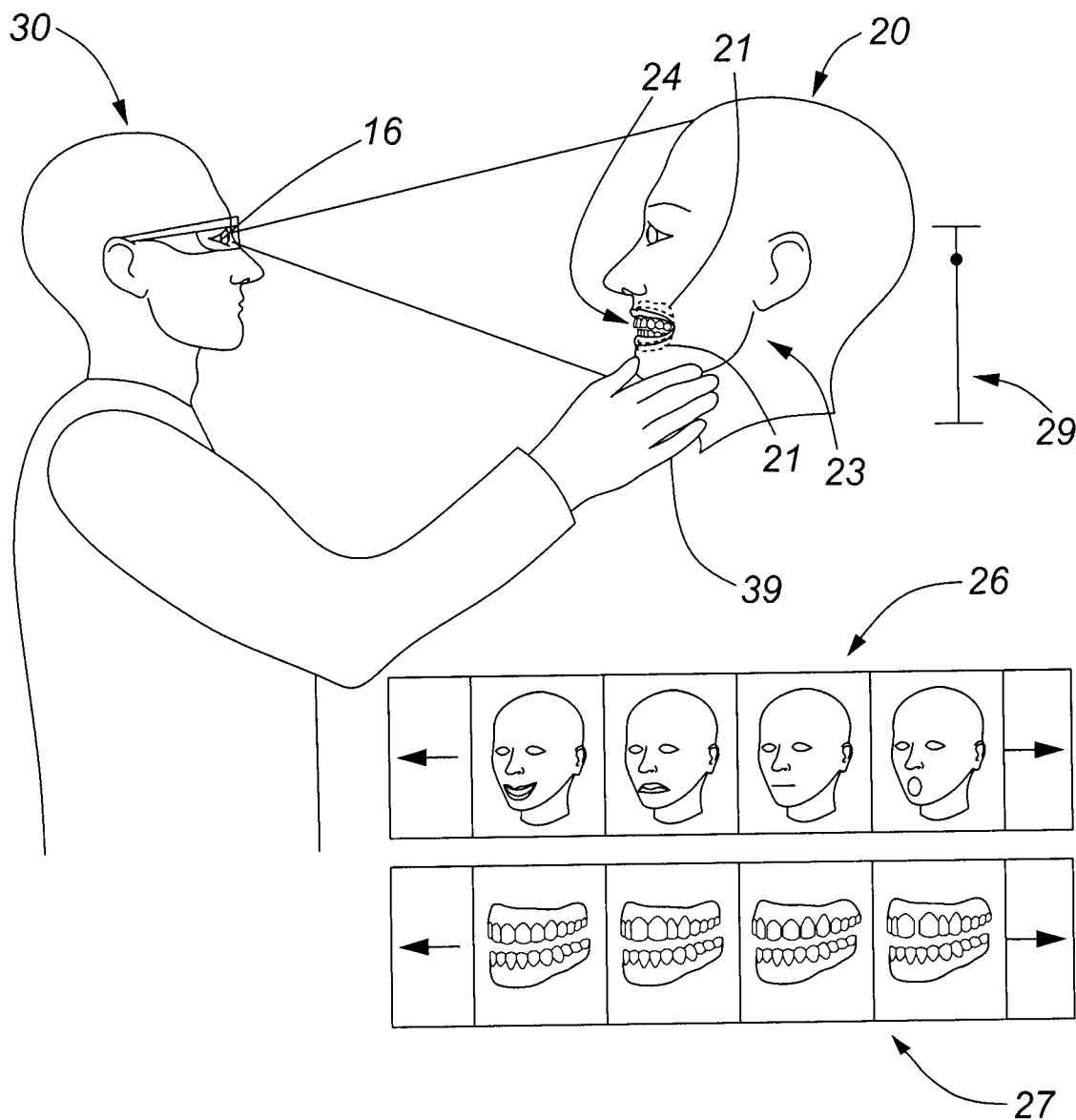
FIG. 6 is the individual manipulating the 3D model of FIG. 1.

FIG. 6 shows the individual 30 directly interacting with the 3D model 20. The individual 30 is gesturing as if to grip the 3D model 20 shown on the 3D display with the hand 39. The maxillomandibular relationship between the modeled arches 21, the modeled external features 23, and the proposed dental appliance 24 may each be manipulated, and the resulting effects on the 3D model 20 calculated by the processor 12. The 3D model 20 is updated to account for differences in the subject features 22, the proposed dental appliance 24, or both. Corresponding differences on the external features 34 of the individual 30 are reflected by changes in the modeled external features 23 and the corresponding portions of the 3D model 20. Gripping a portion of the 3D model 20 and manipulating the 3D model 20 with intuitive gestures updates the 3D model 20 in real time, facilitating comparing the effects of these changes on aesthetics of the modeled external features 23, the dentition 25, or other aspects of the 3D model 20.

Saved positions 26 for the model 20 may be available for viewing. The saved positions 26 may include, for example, saved facial expressions (e.g. smiles, frowns, etc.). In the saved positions 26, the maxillomandibular relationship of the modeled arches 21, the modeled external features 23, or both, are updated to reflect the saved positions 26. The features of the proposed dental appliance 24 and the corresponding augmented reality data 50 can be updated from the saved position 26, and any resulting differences on the external features 34 of the individual 30 reflected in the 3D model 20. The saved positions 26 may include custom smiles with preset sizes and position of dentition 25, for example to reflect celebrity smiles or a smile that the individual 30 previously had.

Saved dental appliances 27 may also be available for including in the 3D model 20. The individual 30 may choose between the prearranged saved dental appliances 27 and make custom alterations to the saved dental appliances 27. In addition, the tooth shade can changed with a shade selector 29. A new saved dental appliance 27 may be selected before or after selection of a saved position 26 to facilitate observing the relative aesthetics of different saved dental appliances 27 at different saved positions 26.

The method 80 of FIG. 2 is applied when the 3D model 20 is manipulated. In response to receiving the first input data 60 from the motion sensor 18, the processor 12 evaluates whether the first input data 60 results in updates to the 3D model 20, the augmented reality data 50, or the external feature data 46. The arches data 42 and the relational data 44 will remain constant.

In addition to gripping the 3D model 20 as shown in FIG. 6, other hand gestures can be used to manipulate the model 20.

Figure 7:
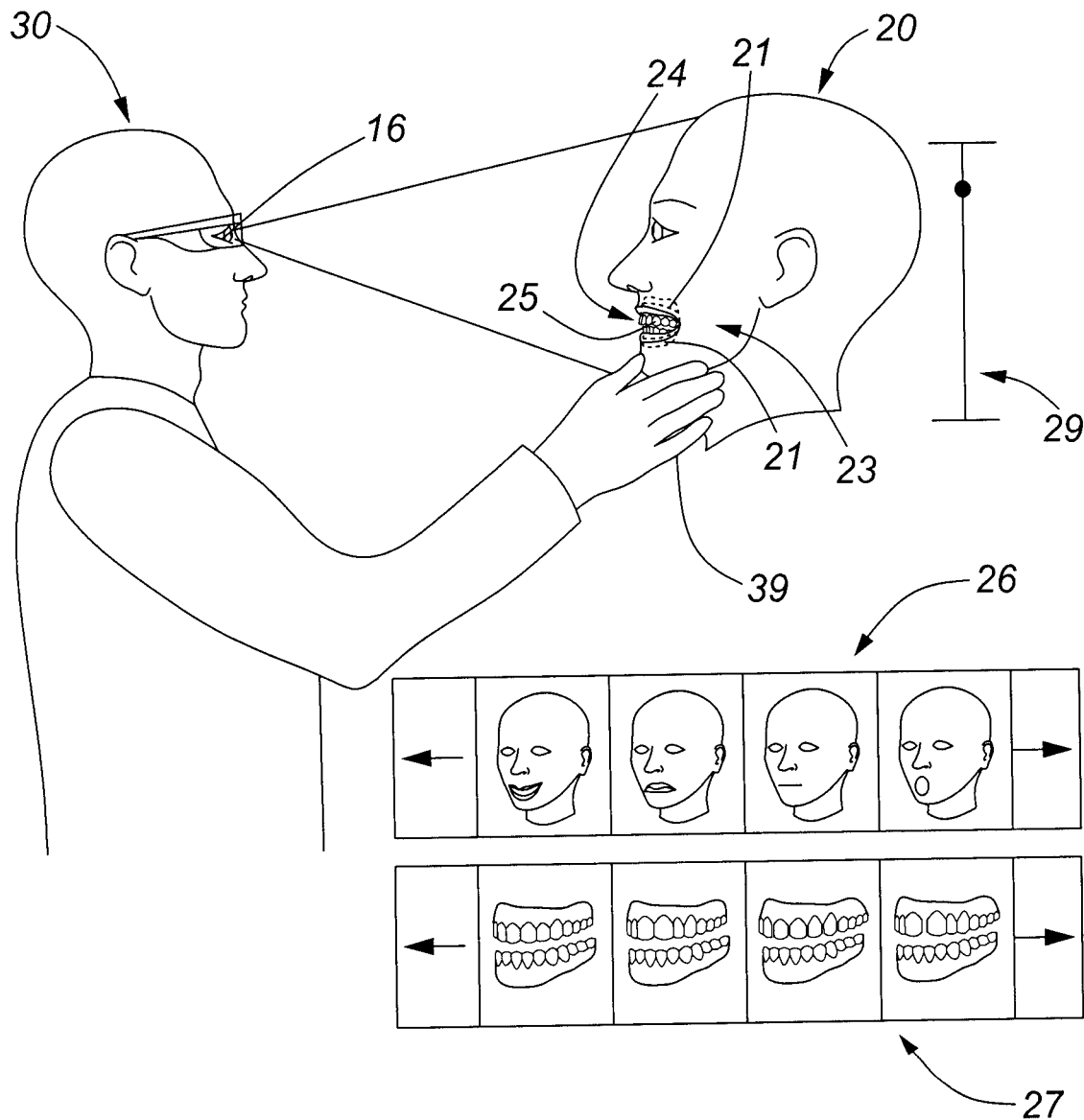
FIG. 7 is the individual manipulating the 3D model.
Figure 8:
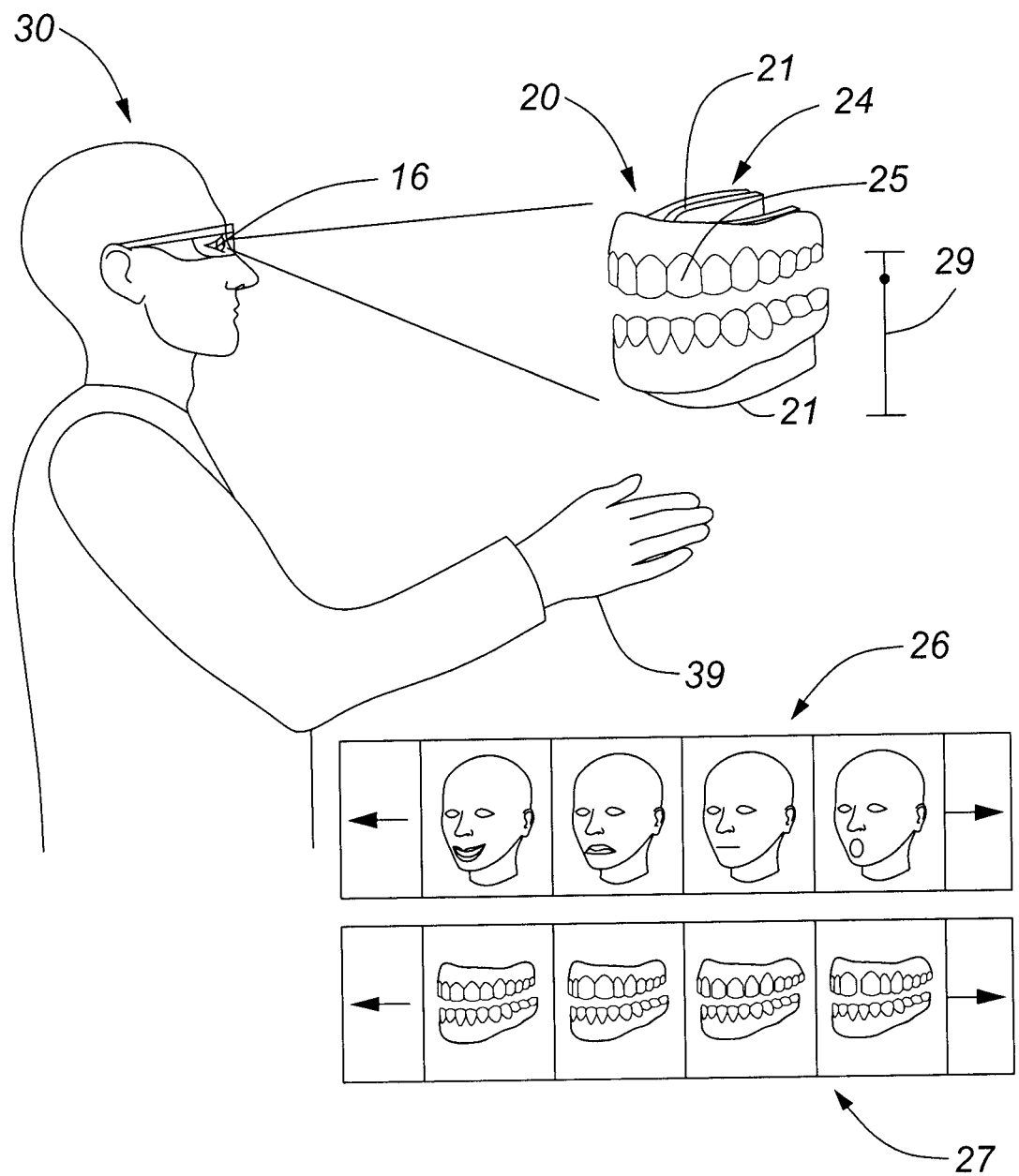
FIG. 8 is the individual manipulating the 3D model.

FIGS. 7 and 8 show the individual 30 manipulating the model 20 without contacting the model 20 with the hand 39. In FIG. 8, only the proposed dental appliance 24 portion of the 3D model 20 is shown. In this way, the dentition 25 and other aspects of the proposed dental appliance 24 may be updated free of obstruction by the subject features 22. Once changes to the dentition 25 or other features of the proposed dental appliance 24 are complete, the subject features 22 may be reintroduced into the 3D model 20 as displayed on the 3D display 16 to facilitate observation of the effects of the changes to the proposed dental appliance 24 on the modeled external features 23.

In additional to facilitating manipulation of the proposed dental appliance 24 and the subject features 22, the system may facilitate intuitive viewing from multiple angles, zooming, and other changes in perspective.

Figure 9:
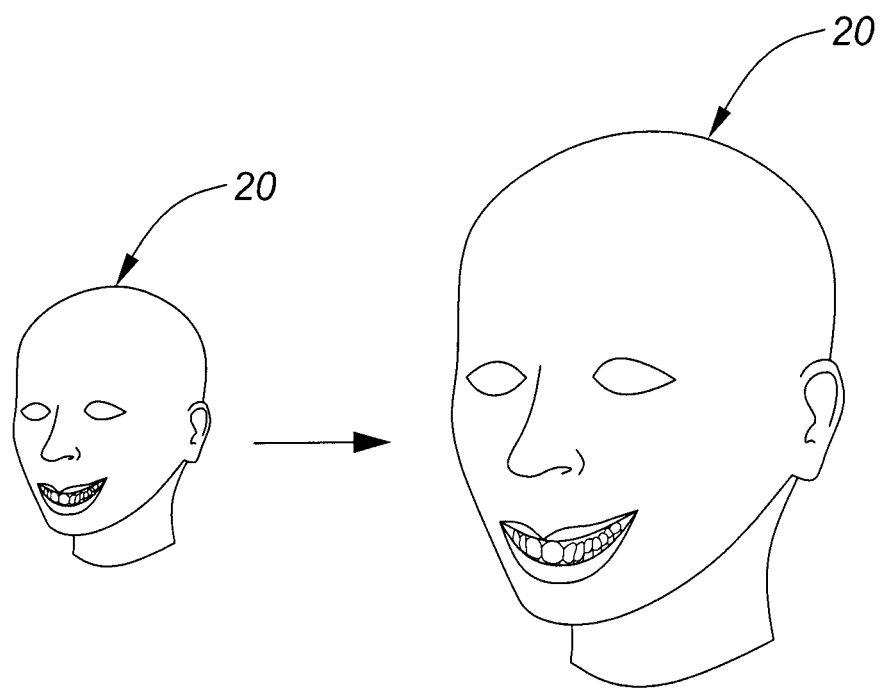
FIG. 9 is the individual zooming in on the 3D model.
Figure 9:
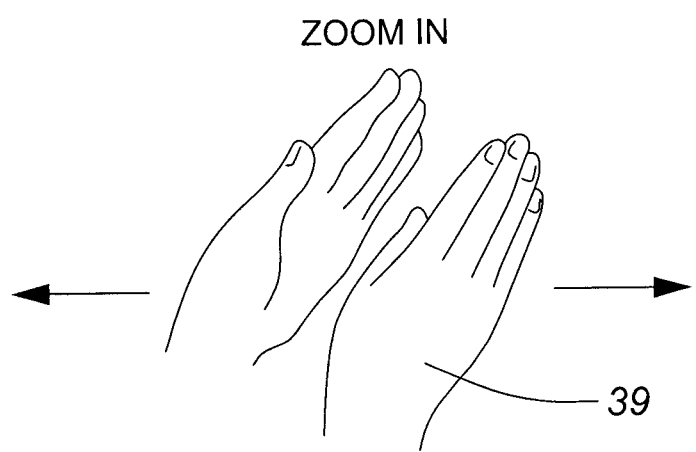
Figure 10:
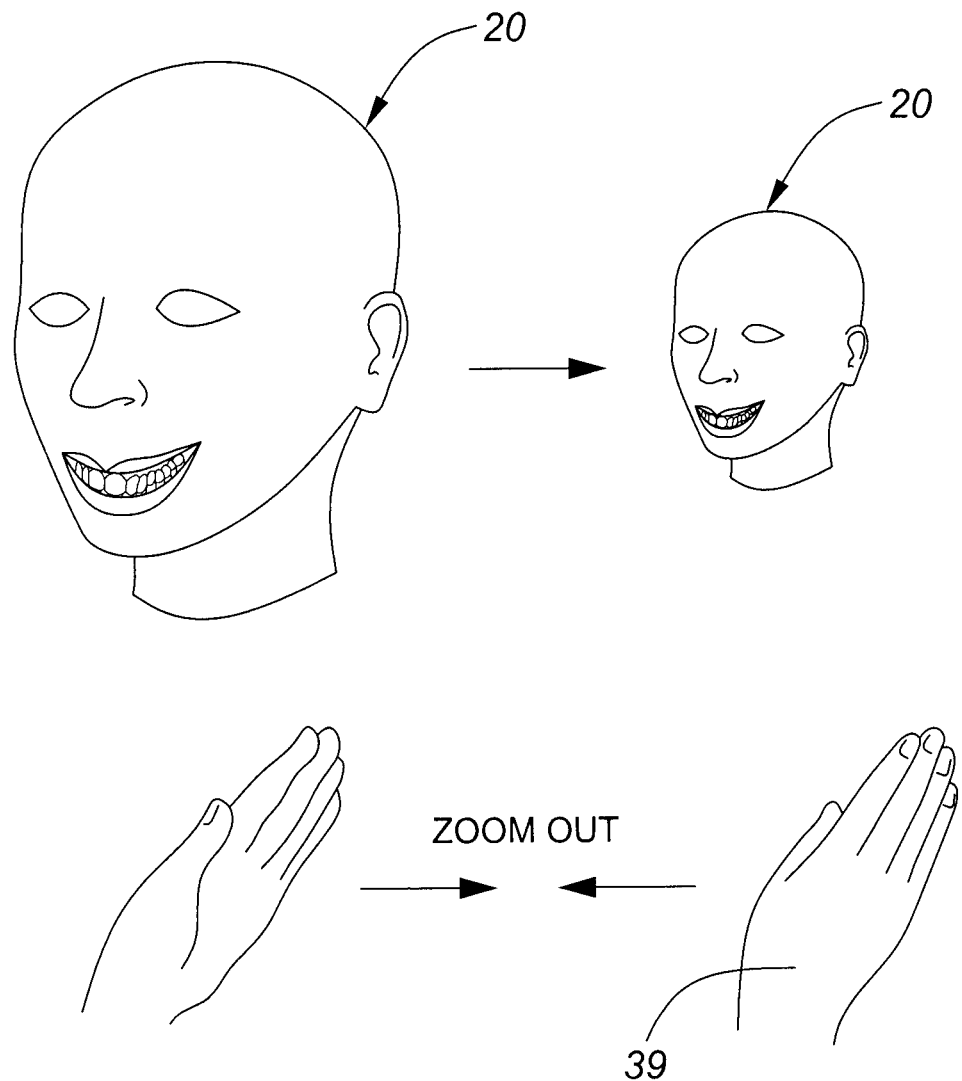
FIG. 10 is the individual zooming out from the 3D model.

FIGS. 9 and 10 respectively show the individual 30 manipulating the model 20 by moving two hands 39 together to zoom in and moving the hands 39 apart to zoom out.

Figure 11:
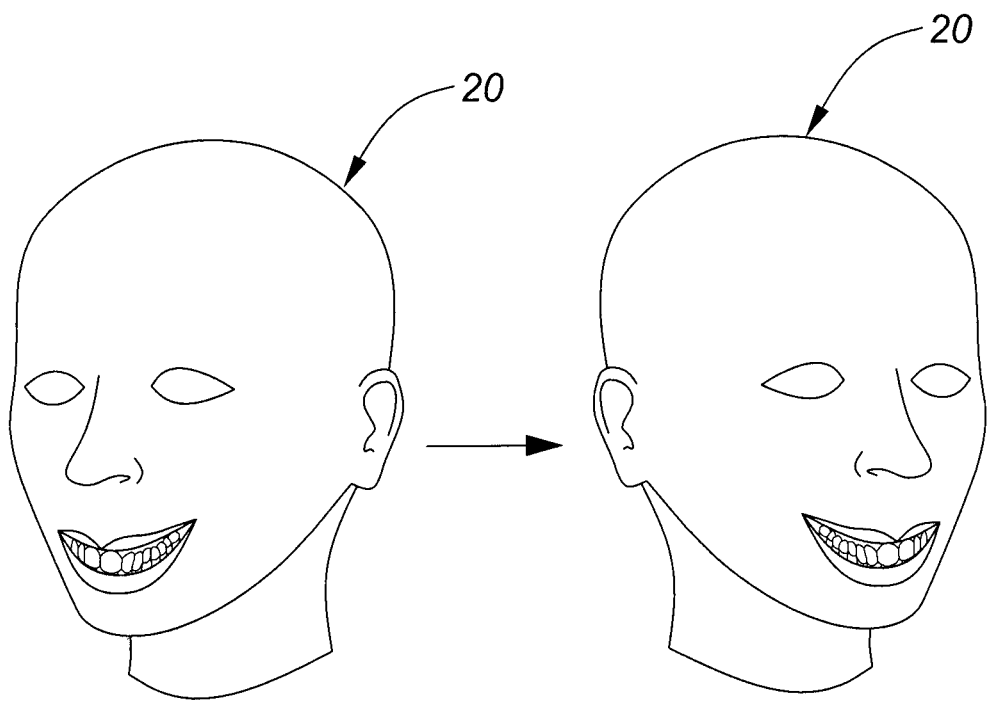
FIG. 11 is the individual rotating the 3D model.
Figure 11:
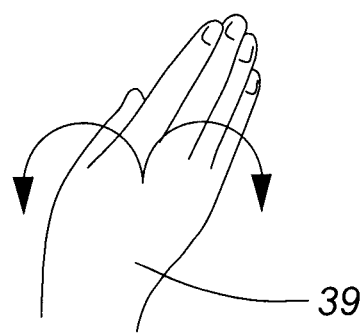

FIG. 11 illustrates the individual 30 rotating the 3D model 20 by rotating the hand 39.

Figure 12:
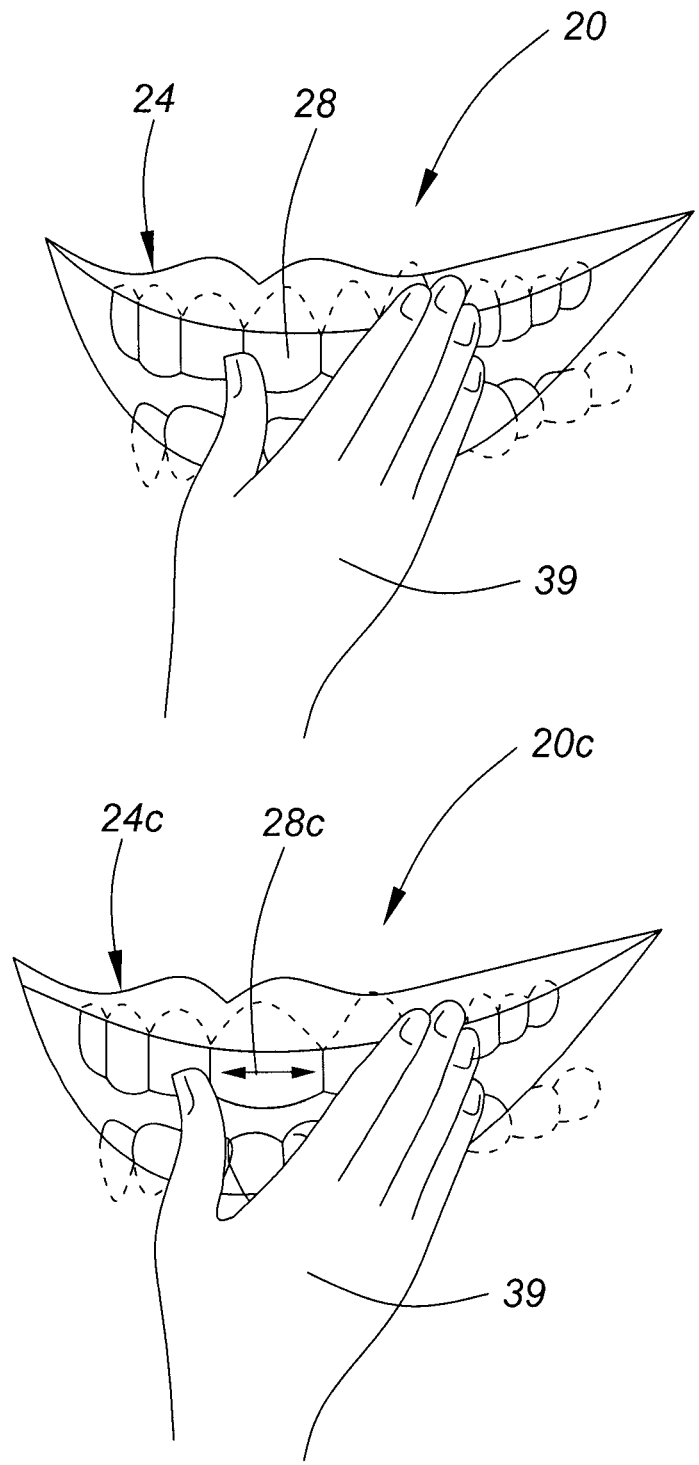
FIG. 12 is the individual increasing the size of one tooth in the 3D model.
Figure 13:
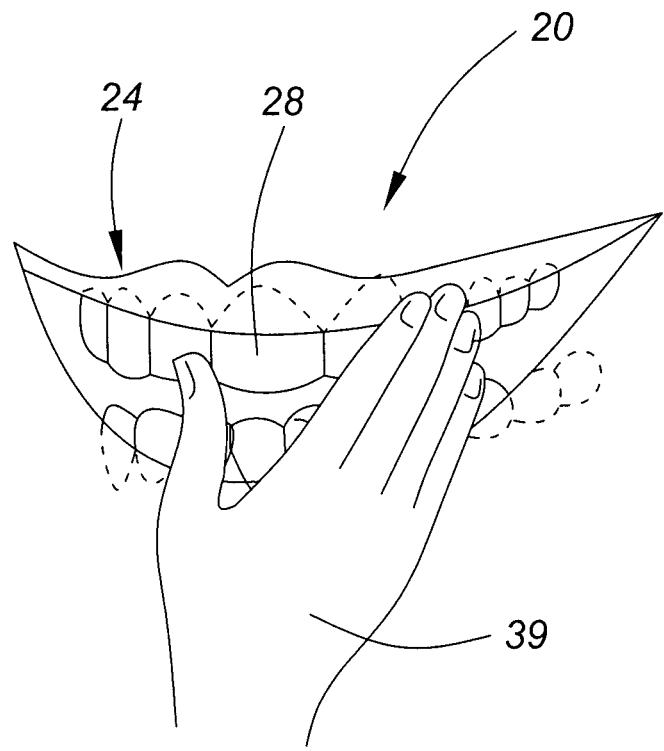
FIG. 13 is the individual decreasing the size of one tooth in the 3D model.
Figure 13:
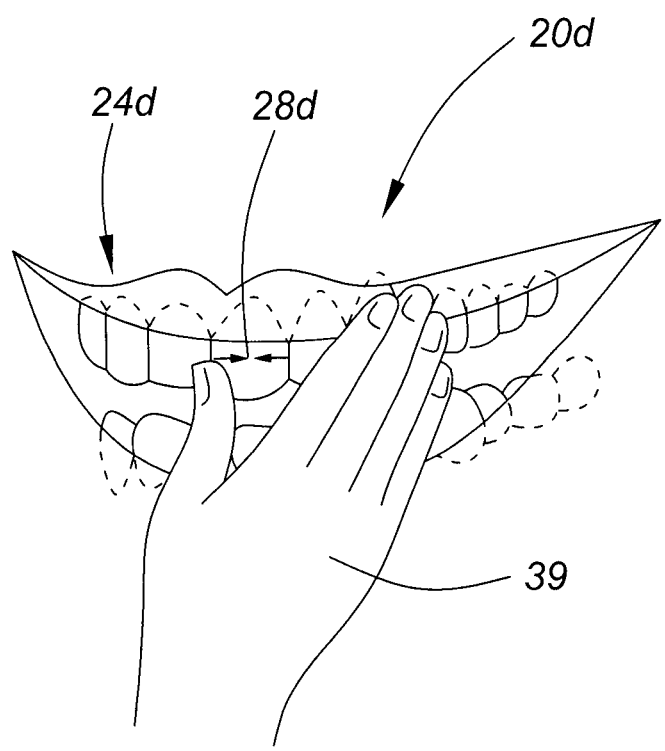

FIGS. 12 and 13 illustrate the individual 30 respectively enlarging and shrinking a single tooth 28 by gripping the single tooth 28 on the 3D model 20 and moving the hand 39 as if to stretch or compress the single tooth 28. Enlarging the single tooth 28 results in an enlarged single tooth 28c, and a corresponding modified dental appliance 24c and updated 3D model 20c. Similarly, shrinking the single tooth 28 results in a reduced single tooth 28d and a corresponding modified dental appliance 24d and updated 3D model 20d.

Figure 14:
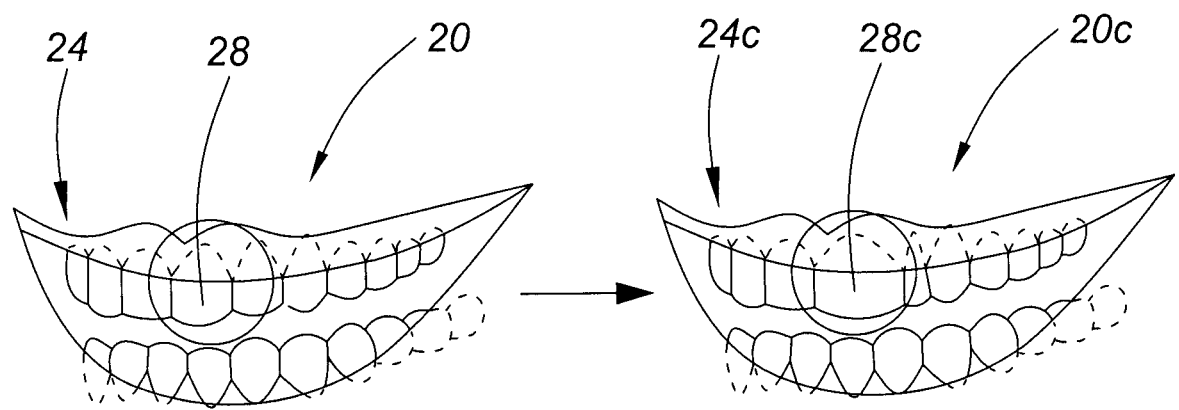
FIG. 14 is the individual increasing the size of one tooth in the 3D model.
Figure 14:
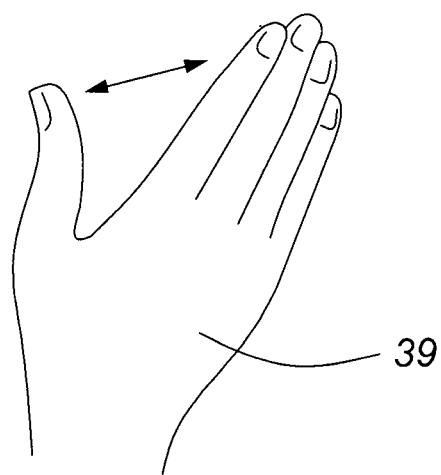
Figure 15:
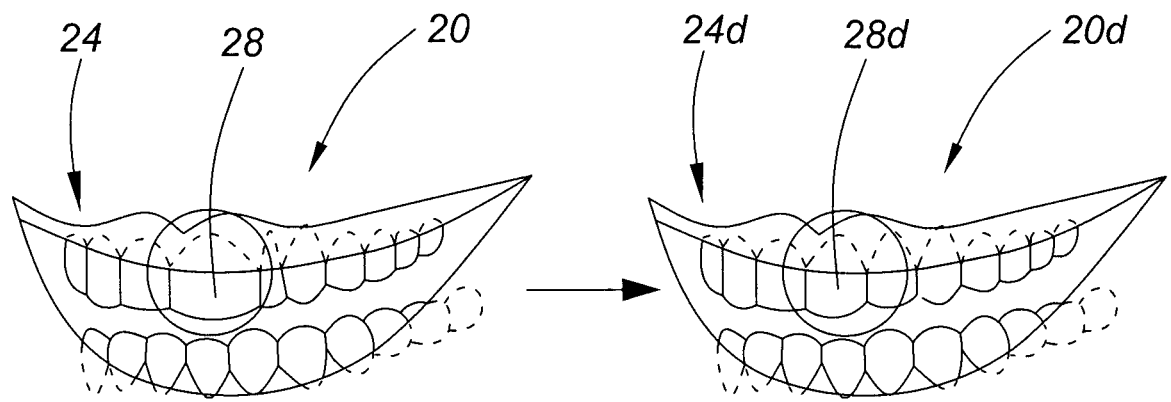
FIG. 15 is the individual decreasing the size of one tooth in the 3D model.
Figure 15:
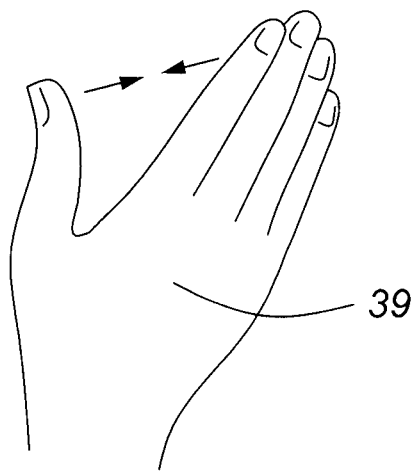

FIGS. 14 and 15 illustrate the individual 30 respectively enlarging and shrinking a single tooth 28 by hand gestures similar to those of FIGS. 12 and 13 but which do not include gripping the 3D model 20.

The individual 30 can change tooth shape, size, shade and position of the proposed dental appliance 24 and observe the resulting changes on the modeled external features 23 and on the 3D model 20 as a whole in real-time. The 3D model 20 may be viewed from any angle or position, facilitating observation of changes to the 3D model 20 from various angles. The 3D model 20 may be viewed with a first facial expression, the facial expression updated to an updated facial expression, and the external features 23 of the 3D model 20 updated accordingly. The updated facial expression may for example be selected from the saved positions 26, prepared by manipulating the individual features 22 of the 3D model 20, or may be prepared based on additional external features data 46 which is acquired (e.g. with the extraoral scanners 992, 1092, 1192, or 1392 shown in FIGS. 33, 35, 38, and 40, respectively). The positions of dentition 25 on the proposed dental appliance 24 are limited within preset parameters which are selected to maintain a selected bite, so as to not allow the dentition 24 to be arranged such that the bite is outside of functional limits.

Data Included in the 3D Model

Figure 16:
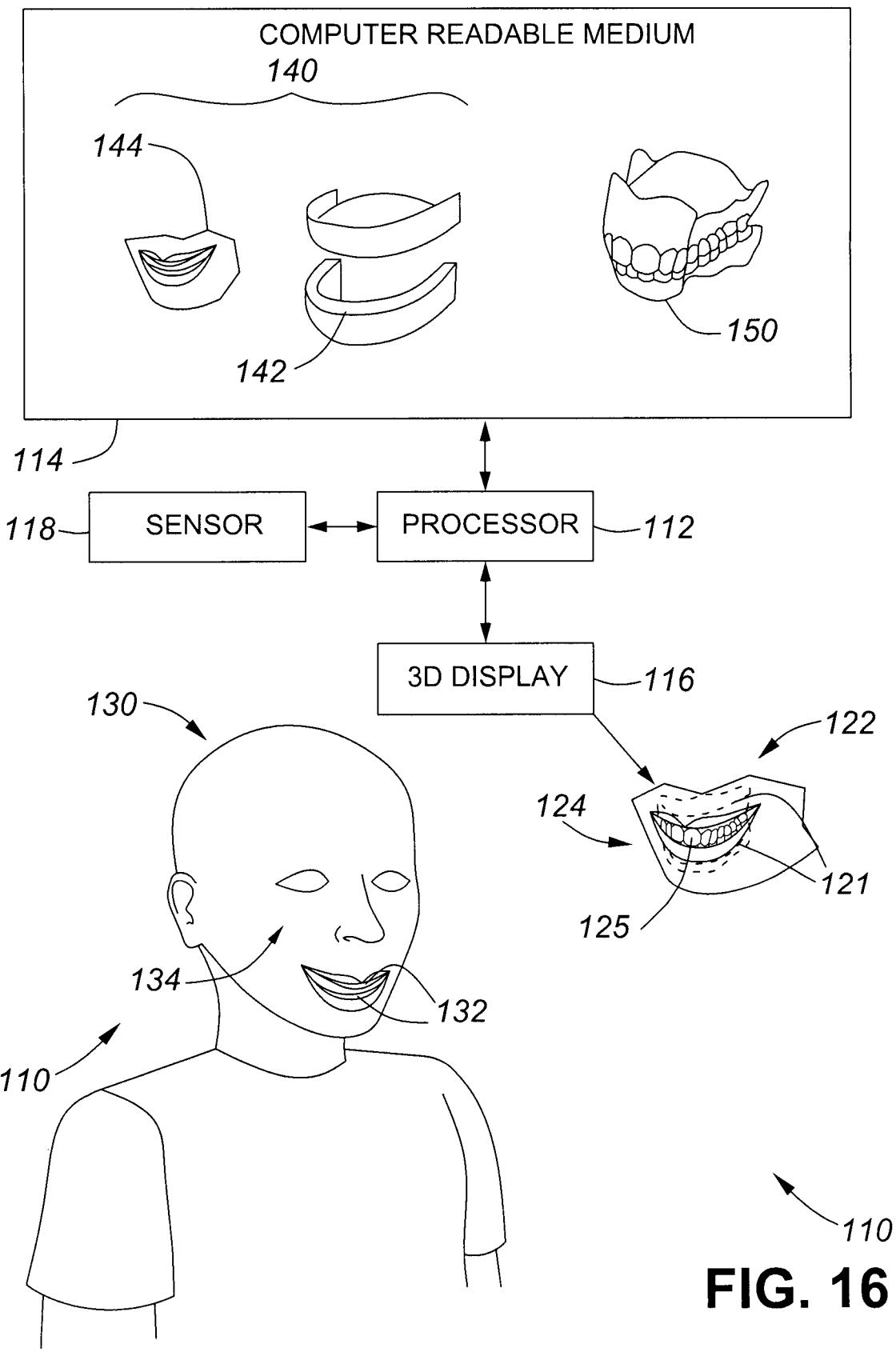
FIG. 16 is a schematic of a system for displaying and manipulating a 3D model of an edentulous individual.

FIG. 16 shows a system 110 in which the scanned features data 40 lacks the external feature data 46 and the 3D model 120 lacks the modeled external features 23. The scanned features data 140 includes only the arches data 142 and the relational data 144.

Figure 17:
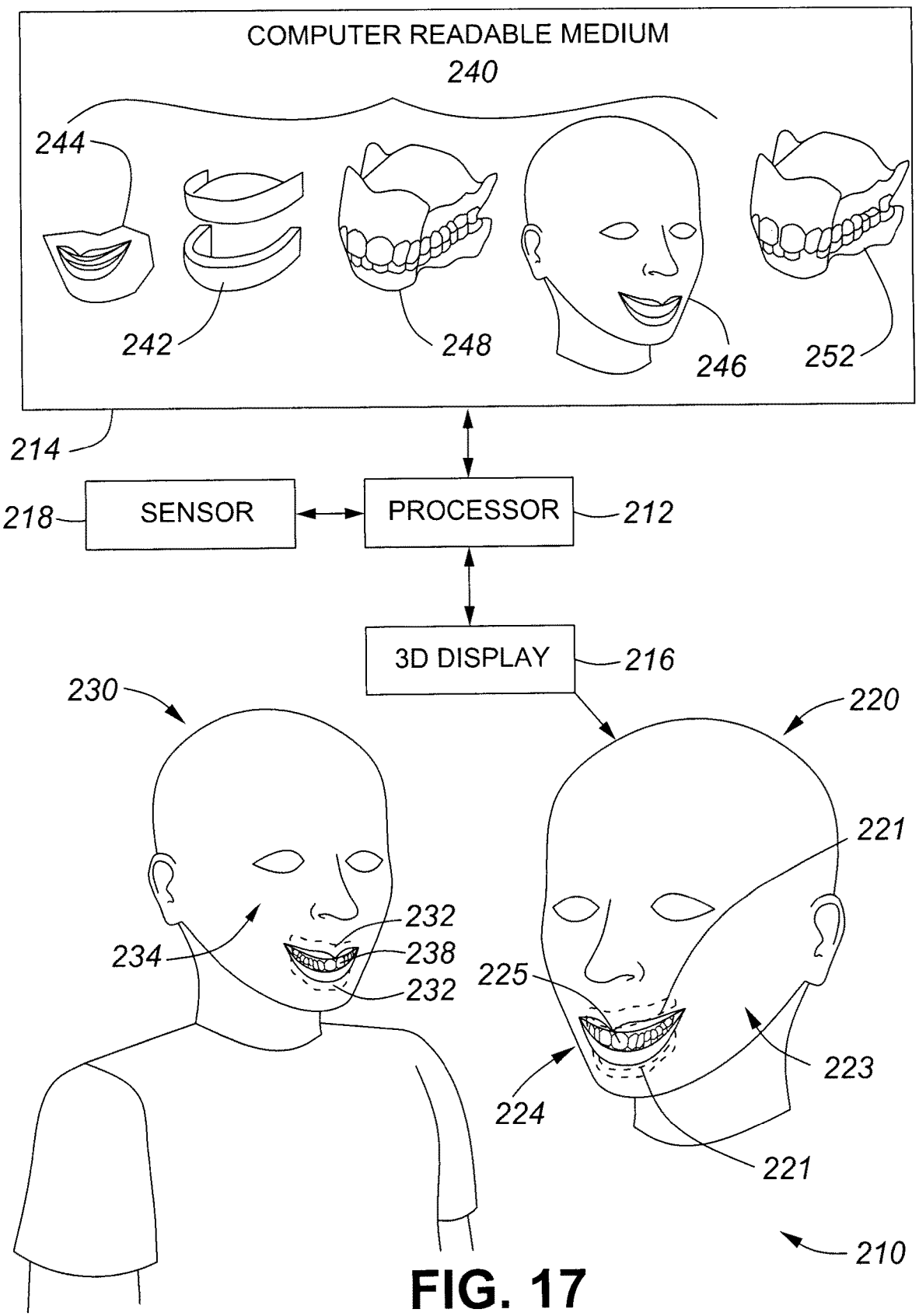
FIG. 17 is a schematic of a system for displaying and manipulating a 3D model of an edentulous individual.

FIG. 17 shows a system 210 wherein the 3D model 220 includes denture data 248 for modeling the individual's dentures 238. The denture data 248 is reflective of the individual 230's current dentures 238 and may be acquired by scanning the individual 230's current dentures 238, for example with an extraoral optical scanner 992 as included in the system 910 of FIG. 33, etc. Augmented reality data 252 is based in part on the denture data 248. The denture data 248 may inform the augmented reality data 252 as a starting point to redesign dentures for the individual 230 by presenting the proposed dental appliance 224 for review in the 3D model 220 and modification. If the individual has more than one pair of current dentures, more than one set of dentures data 248 may be acquired and a corresponding number of sets of augmented reality data 252 would be provided. As with the system 10, the proposed dental appliance 224 may be modified through manipulation of the 3D model 20 without altering the underlying augmented reality data 252. The maxillomandibular relationship at occlusion of the proposed dental appliance 224 may be the same as that of the individual's current dentures 238 or may be modified from that of the individual's current dentures 238 (e.g. to provide an appropriate spacing between the dentition 225 at the rest position, etc.).

Figure 18:
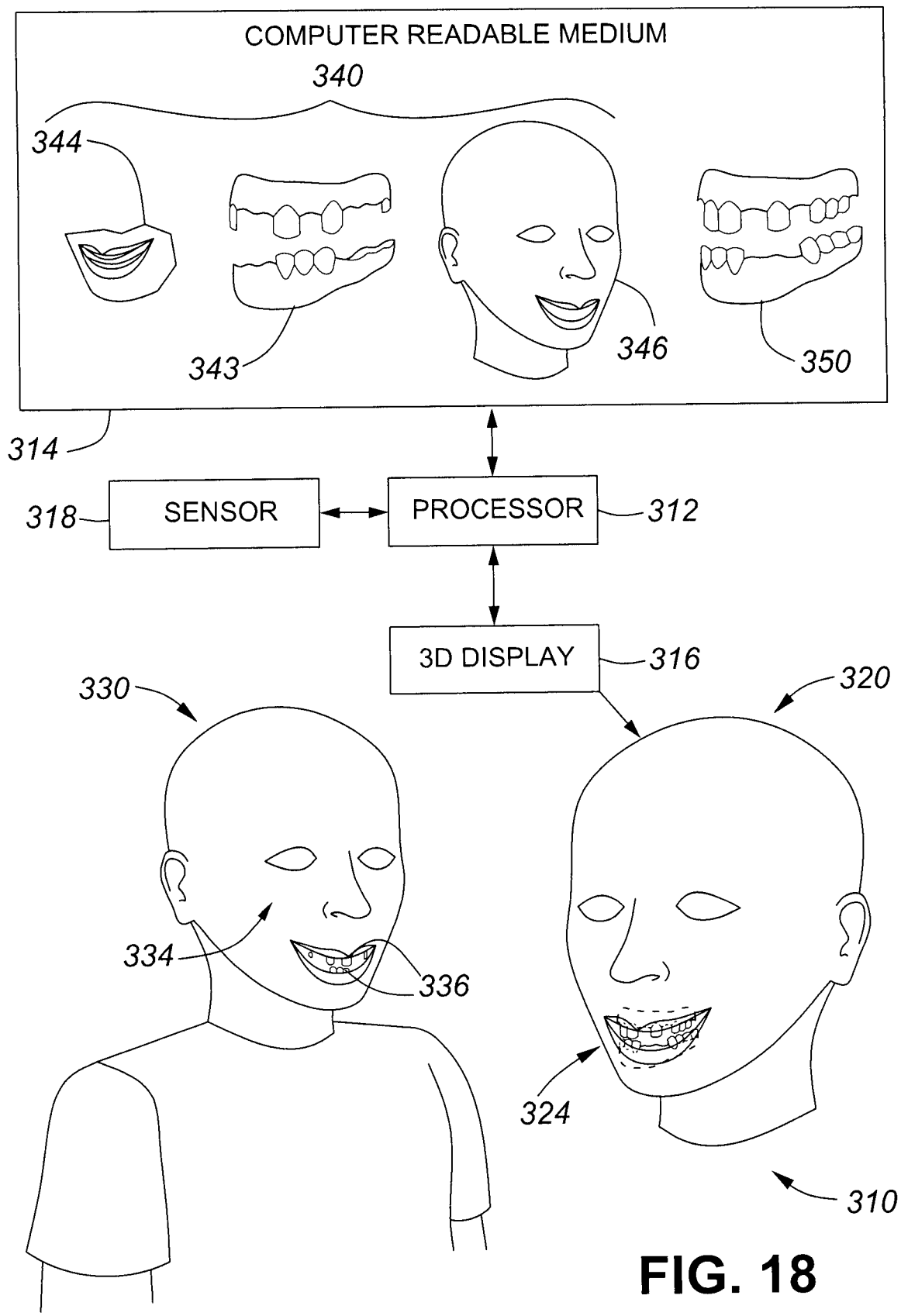
FIG. 18 is a schematic of a system for displaying and manipulating a 3D model of a partially dentate individual.

FIG. 18 shows a system 310 wherein the individual 330 has partial dentition 336. The 3D model 320 includes a representation of the partial dentition 336, which is represented in partially dentate arches data 343. The augmented reality data 350 used to prepare the proposed dental appliance 324 takes into account the presence of the partial dentition 336 as shown in the partially dentate arches data 343.

Brain-Computer Interface

Figure 19:
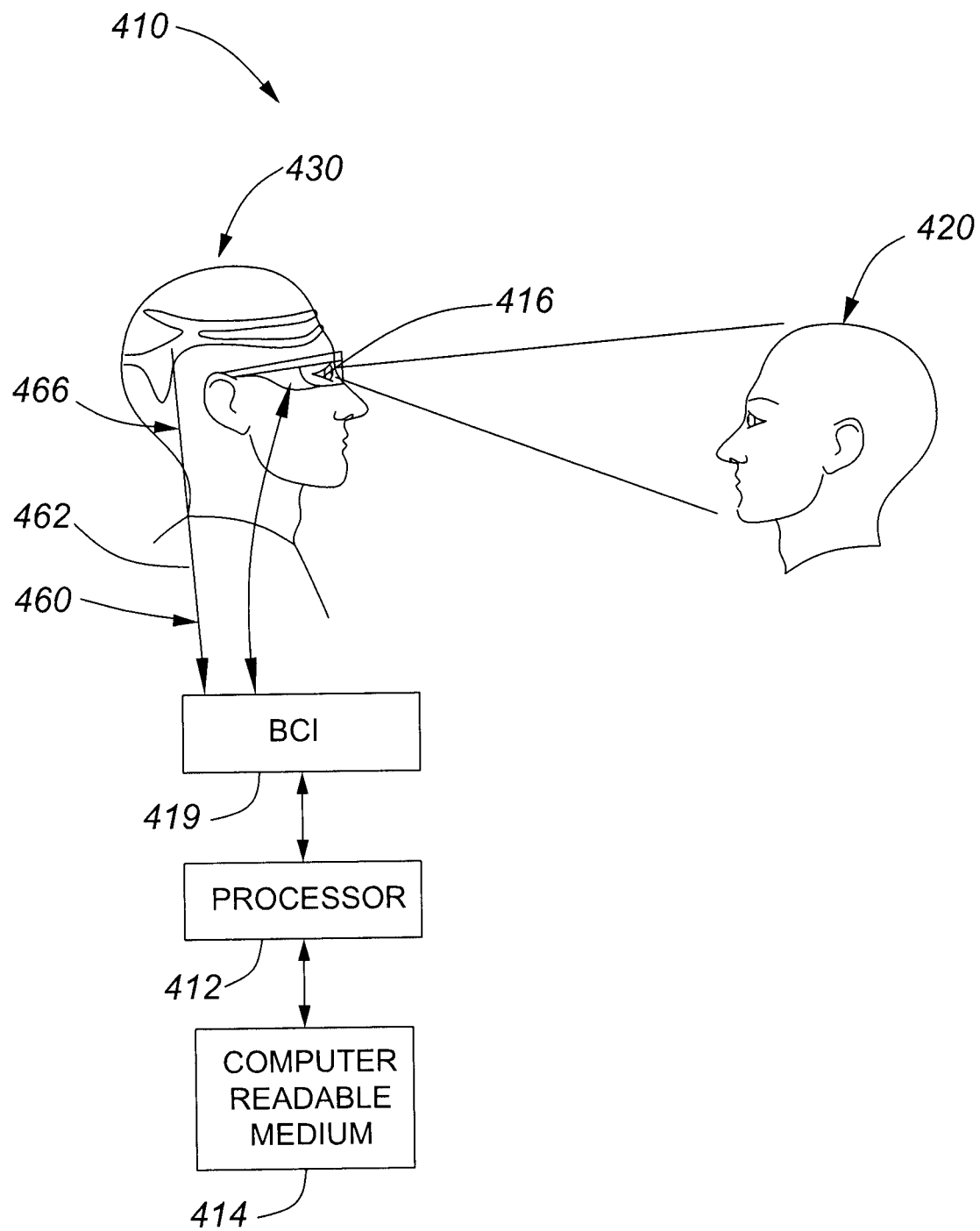
FIG. 19 is a schematic of a system for displaying and manipulating a 3D model of an edentulous individual.

FIG. 19 is a system 410 for displaying and manipulating the 3D model 420.

Figure 20:
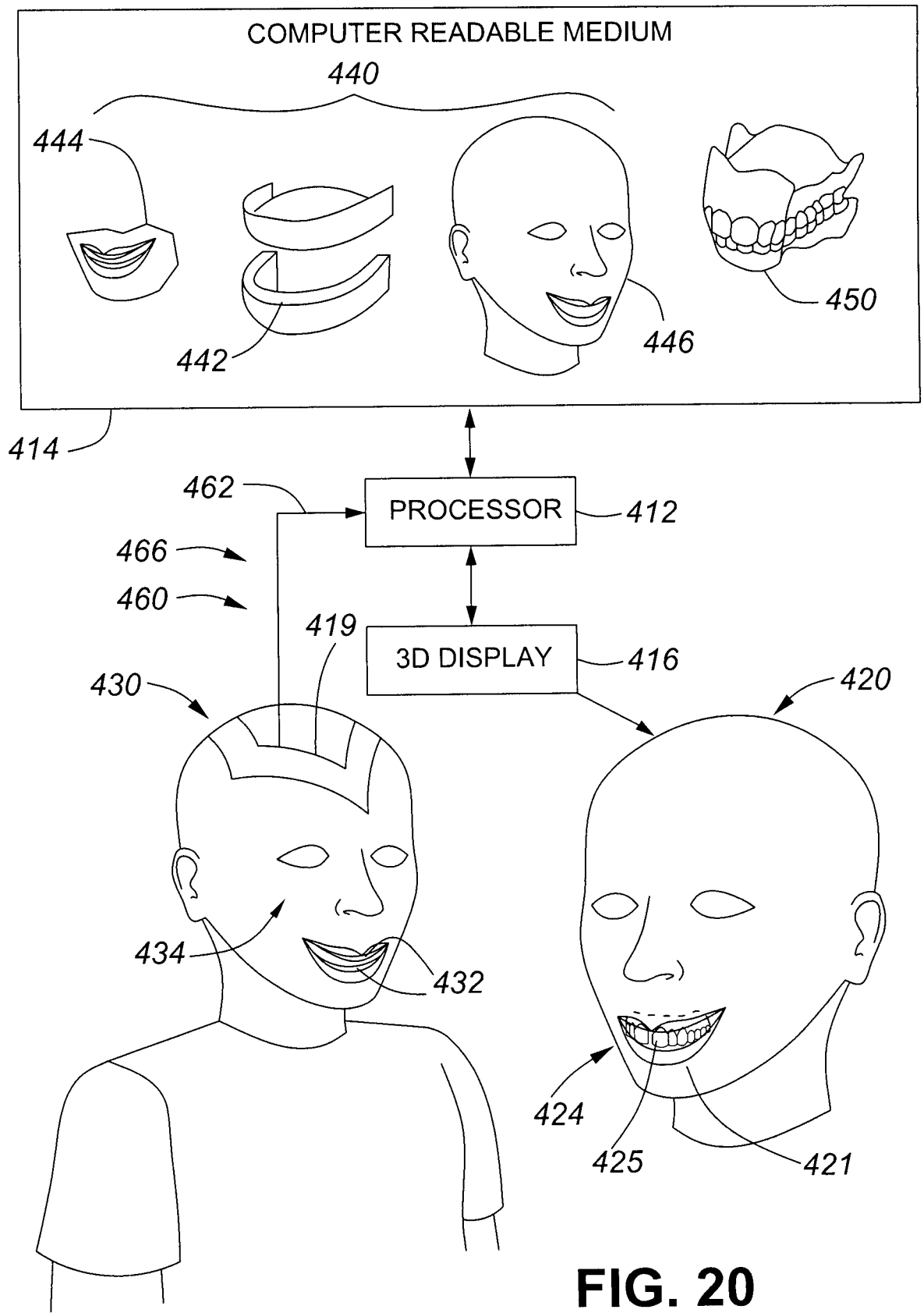
FIG. 20 is the individual of FIG. 16 viewing the 3D model of FIG. 16.

FIG. 20 shows the system 410 and the data 440, 450 used to prepare the 3D model 420.

The system 410 includes the processor 412, the computer readable medium 414, and the 3D display 416. The individual 430 interacts with the 3D model 420 through use of a brain-computer interface ("BCI") 419. The BCI 419 monitors a property of the individual 430's brain indicative of neural activity to receive an input of neural activity data 466. Current examples of BCI systems which may be used as the BCI 419 include the Insight and EPOC/EPOC+ systems manufactured by Emotive and the MindWave system manufactured by NeuroSky, which are both based on electroencephalography ("EEG") and monitor electrical activity of the brain. The BCI 419 may include any suitable BCI which supports real-time use by the individual 430, and is not restricted to a BCI applying EEG. Functional magnetic resonance imaging, which monitors blood flow in the brain, and magneto electroencephalography, which monitors magnetic fields resulting from electrical activity of the brain, may also be used in the BCI 419 to receive the input of neural activity data 466.

The BCI 419 facilitates responsive updating of the 3D model 420 without the need for a motion sensor, audio sensor, or other sensors based on actions of the individual 30 downstream of mental conceptualization of the action or of a change to the 3D model 420. In addition, facial expressions such as blinking, winking, and smiling result in neural activity which may be received as inputs by the BCI 419 and can be used to update the modeled external features 423. Such updates to the modeled external features may be to a saved position 426, other modifications to the positions of the modeled external features 423, or through acquisition of additional external feature data 446 (e.g. as in the system 1010 of FIG. 35, the system 1110 of FIG. 37, etc.). An action actually taken by the individual 420 would include conceptualization of the action, facilitating use of the system 410 where the individual 420 is unfamiliar with use of a BCI 419.

The inputs of neural activity data 466 include the voluntary action data 462 corresponding to mental commands from the individual 430, which are provided to the processor 412. Once calibrated to the individual 430 to the extent necessary for the particular BCI 419 and processor 412, the neural activity data 466 includes the voluntary action data 462 corresponding to thoughts, conceptualized gestures (including gestures which are physically made) conceptualized changes to the 3D model 420, or other mental or emotional activity of the individual 430 related to actions which may be taken in respect of the 3D model 420.

The voluntary action data 462 may correspond to motion, location, position, and angle of gestures of the individual 430 which are mentally conceptualized by the individual 430 (e.g. the inputs may correspond to a series of common and intuitive conceptualized hand gestures which allows the individual 430 to rotate, pan, zoom in and change the lighting conditions on the 3D model 420, etc.). Examples of such gestures which may be conceptualized by the individual 430 and the resulting manipulations to the 3D model 420 may include the hand gestures used to manipulate the proposed dental appliance 24 or the perspective on the model 20 shown in FIGS. 6 to 15 when using the system 10, although with the system 410, the gestures would merely be conceptualized or imagined by the individual 430.

A system may also be prepared combining the features of the system 10 and the system 410, providing a system with both motion sensors and a BCI (not shown). Input from the motion sensors and from the BCI may be weighted differently. In addition, motion sensor input may be used to calibrate the BCI to the individual using such a system.

FIGS. 21 to 27 show the individual 430 manipulating the model 420 by conceptualizing the results of changes, resulting in voluntary action data 462 being received by the BCI 419 in the absence of actual gestures or conceptualized gestures.

Figure 21:
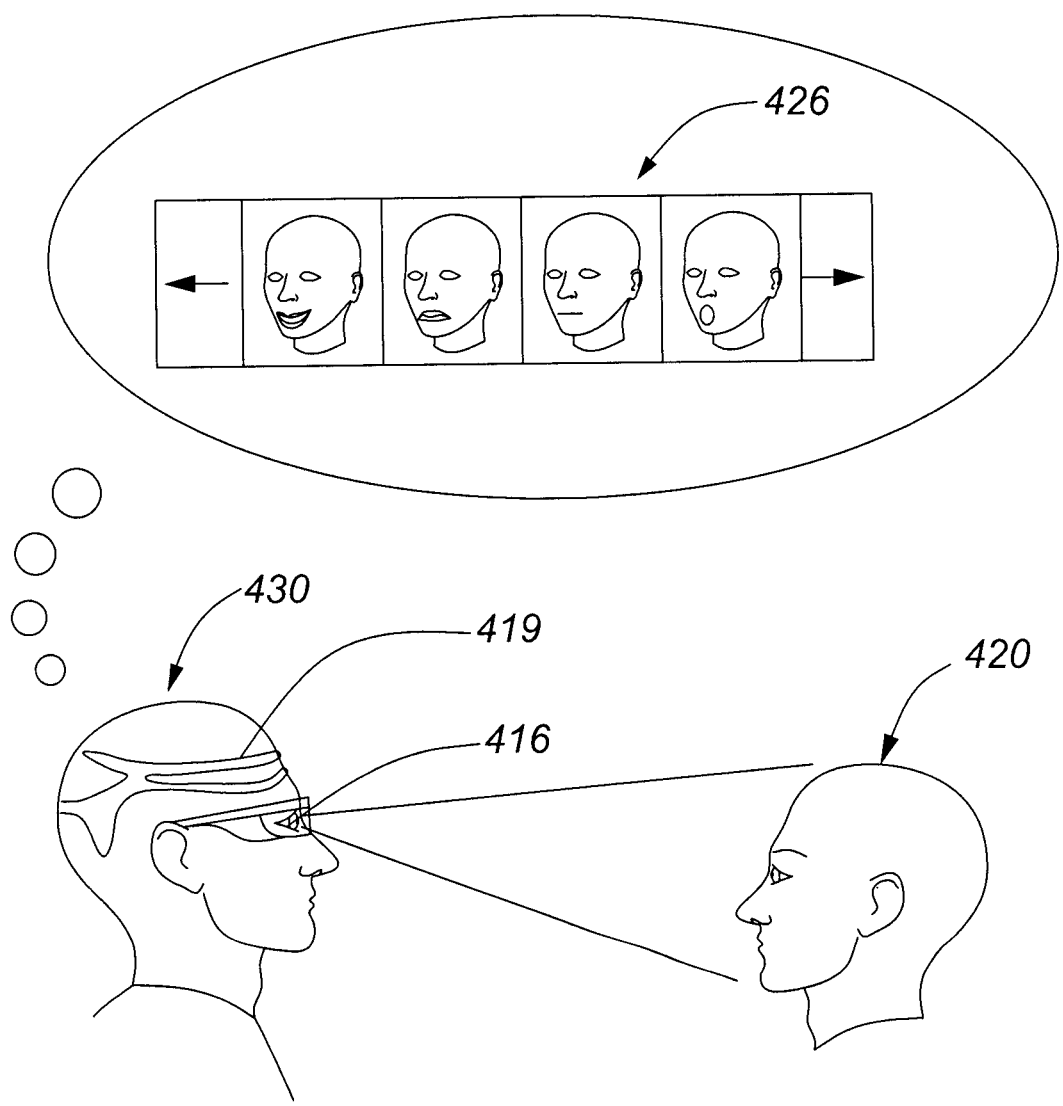
FIG. 21 is the individual manipulating the 3D model.

FIG. 21 shows the individual 430 manipulating the model 420 by conceptualizing a change to one of the saved positions 426, or conceptualizing one of the saved positions 426.

Figure 22:
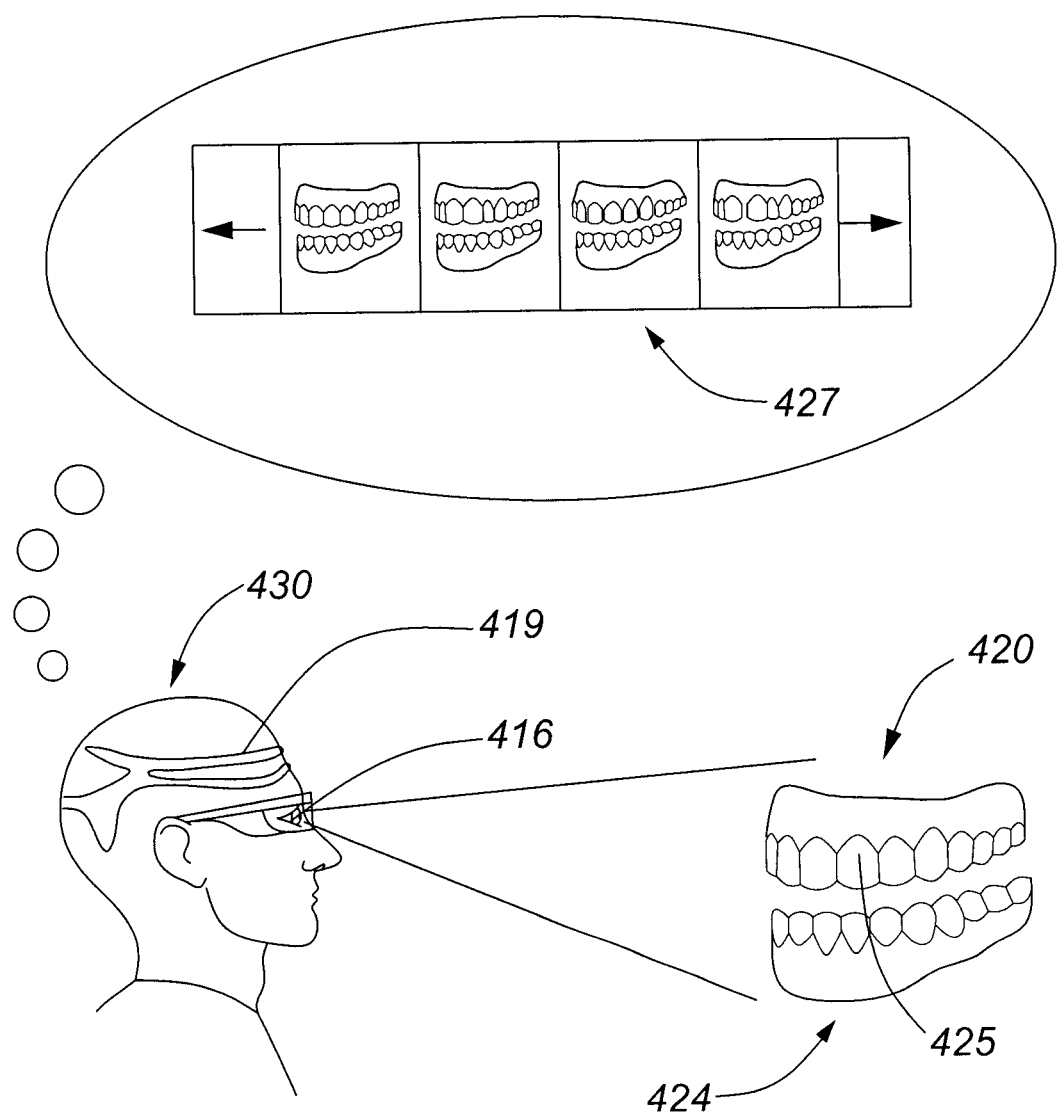
FIG. 22 is the individual manipulating the 3D model.

FIG. 22 shows the individual 430 manipulating the 3D model 420 by conceptualizing changes in the colour and shade of the teeth in the proposed dental appliance 424. In FIG. 22, only the proposed dental appliance 424 portion of the model 420 is shown. The same approach applies to selection of one of the saved dental appliances 427. The 3D display 416 may show the saved positions 426, saved dental appliances 427, and the shade selector 429 for the individual 430 to focus on and change through the voluntary action data 462. Alternatively, these features may be omitted from display on the 3D display 416 and the individual need only conceptualize which saved position 426, saved dental appliance 427, or change in shade that the individual 430 would like to see displayed on the 3D model 420.

Figure 23:
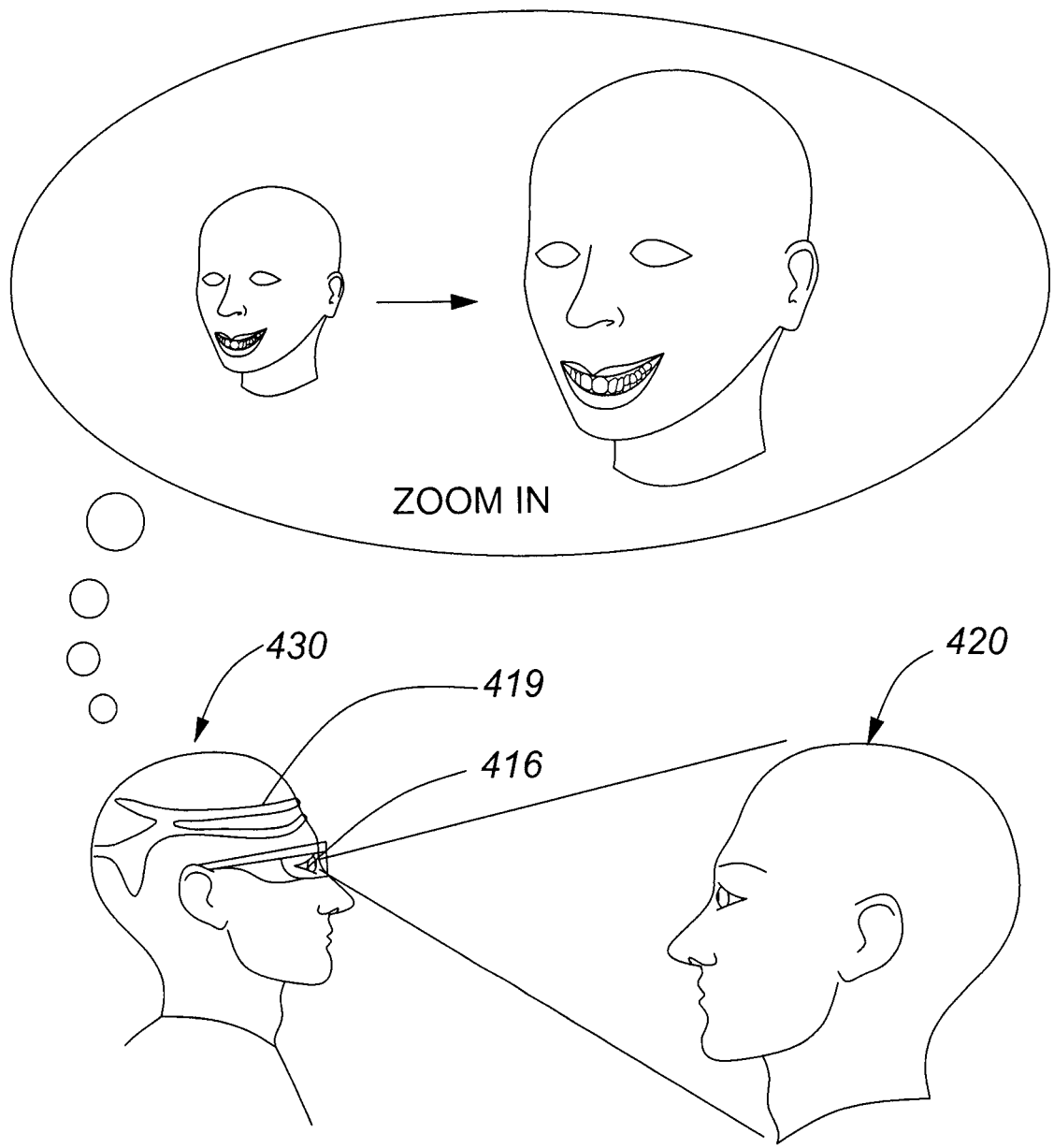
FIG. 23 is the individual zooming in on the 3D model.
Figure 24:
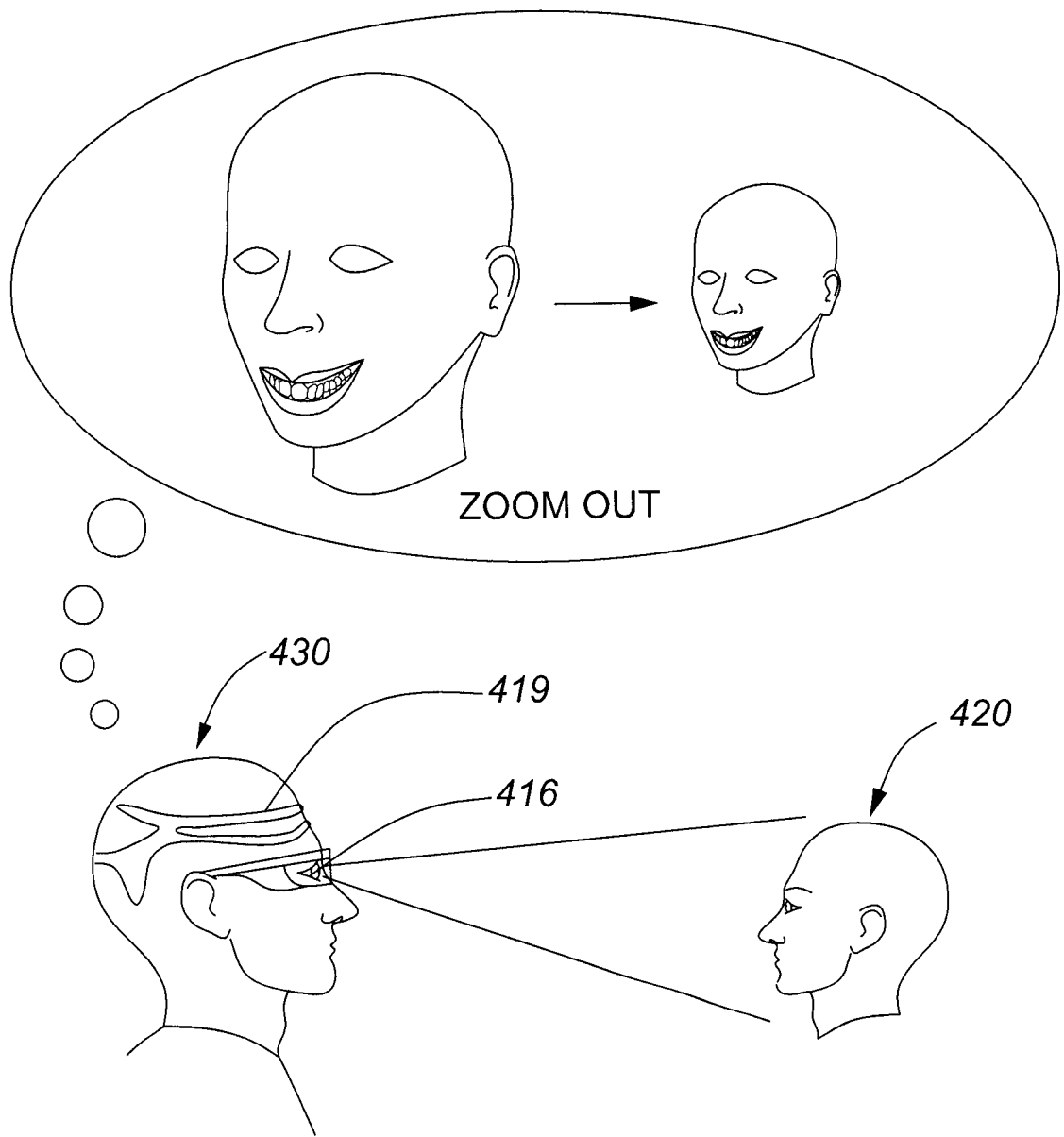
FIG. 24 is the individual zooming out from the 3D model.
Figure 25:
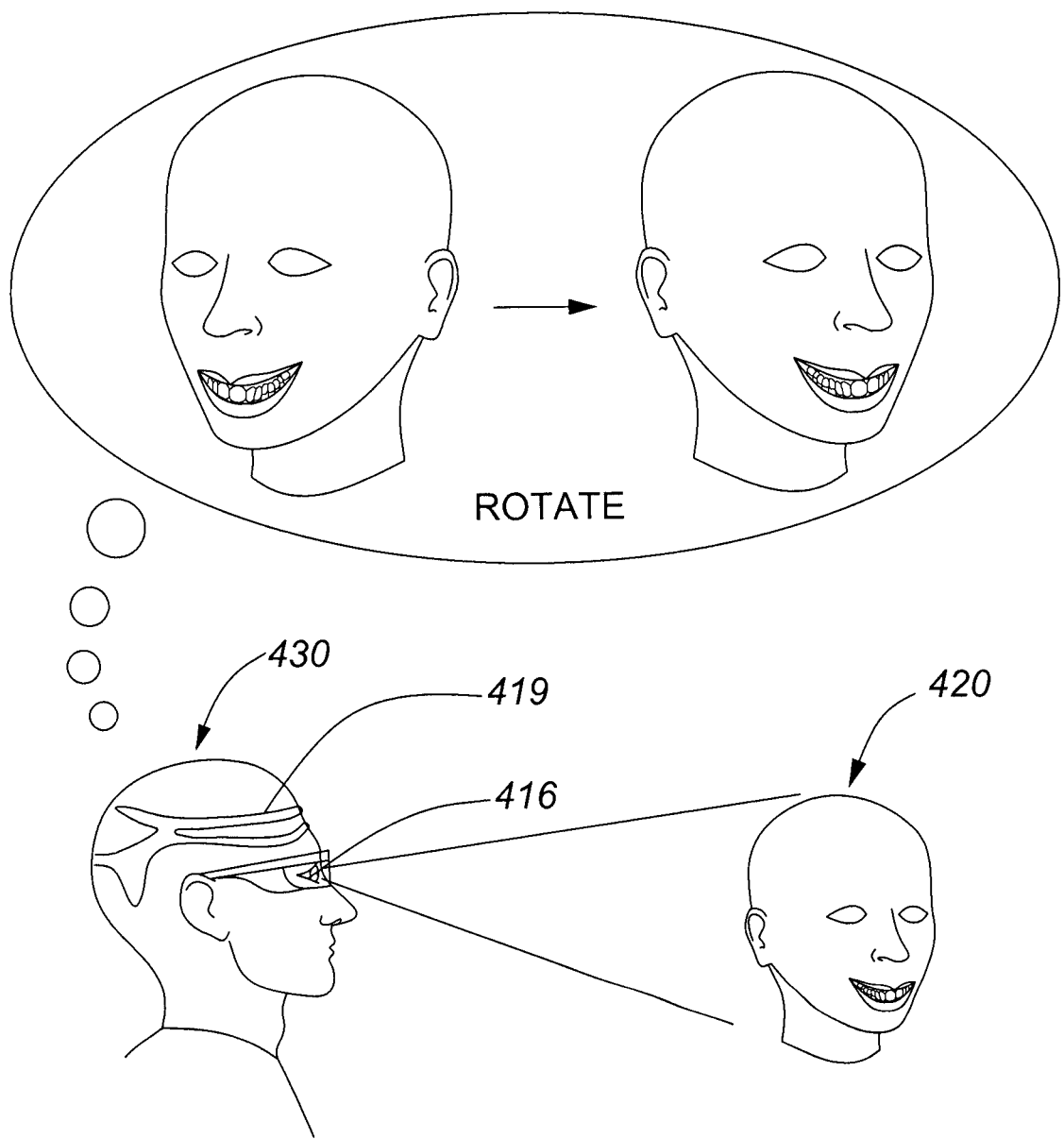
FIG. 25 is the individual rotating the 3D model.

FIGS. 23 to 25 respectively show the individual 430 manipulating the model 420 by conceptualizing zooming in, zooming out, and rotating the 3D model 420.

Figure 26:
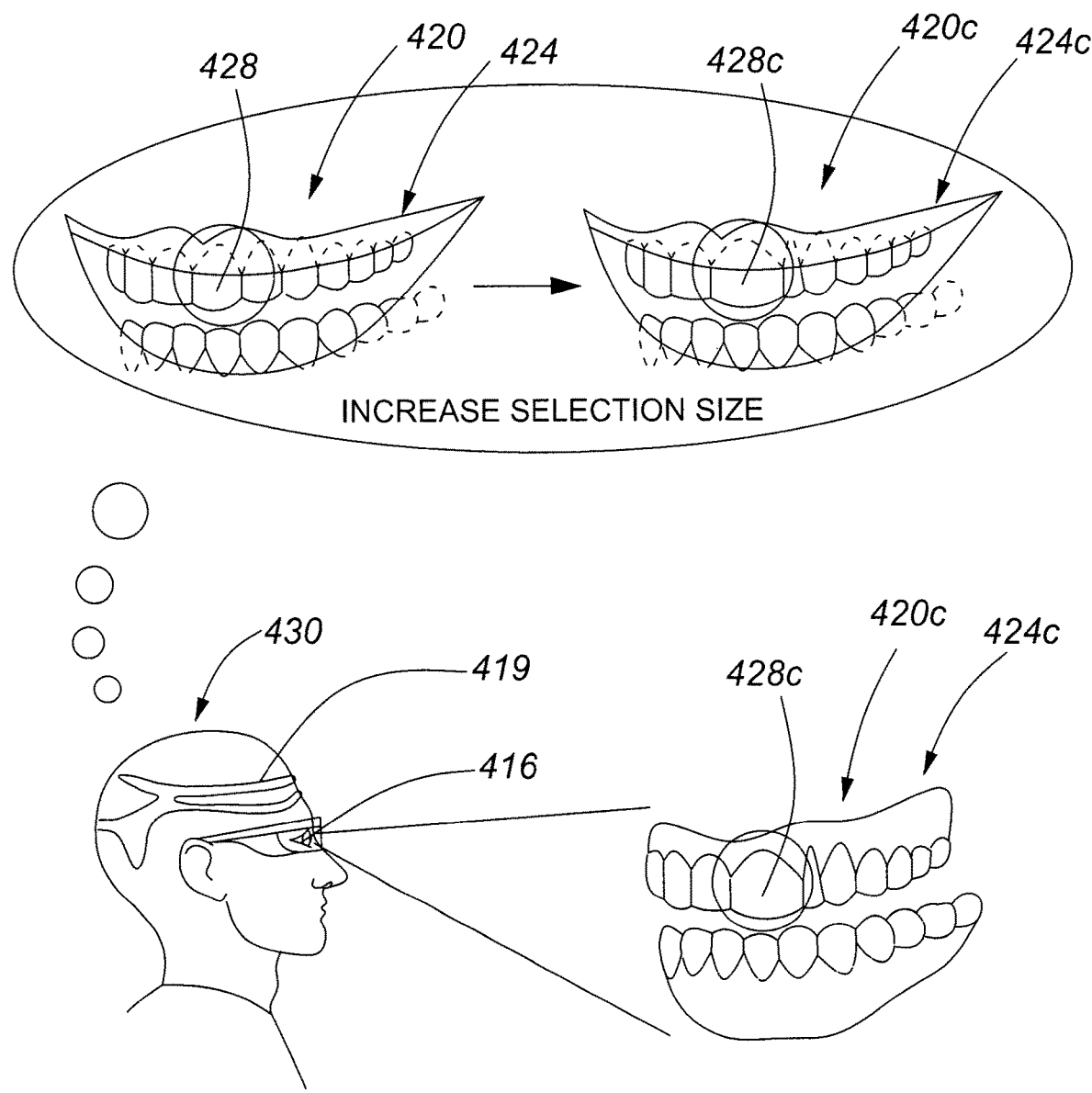
FIG. 26 is the individual increasing the size of one tooth in the 3D model.
Figure 27:
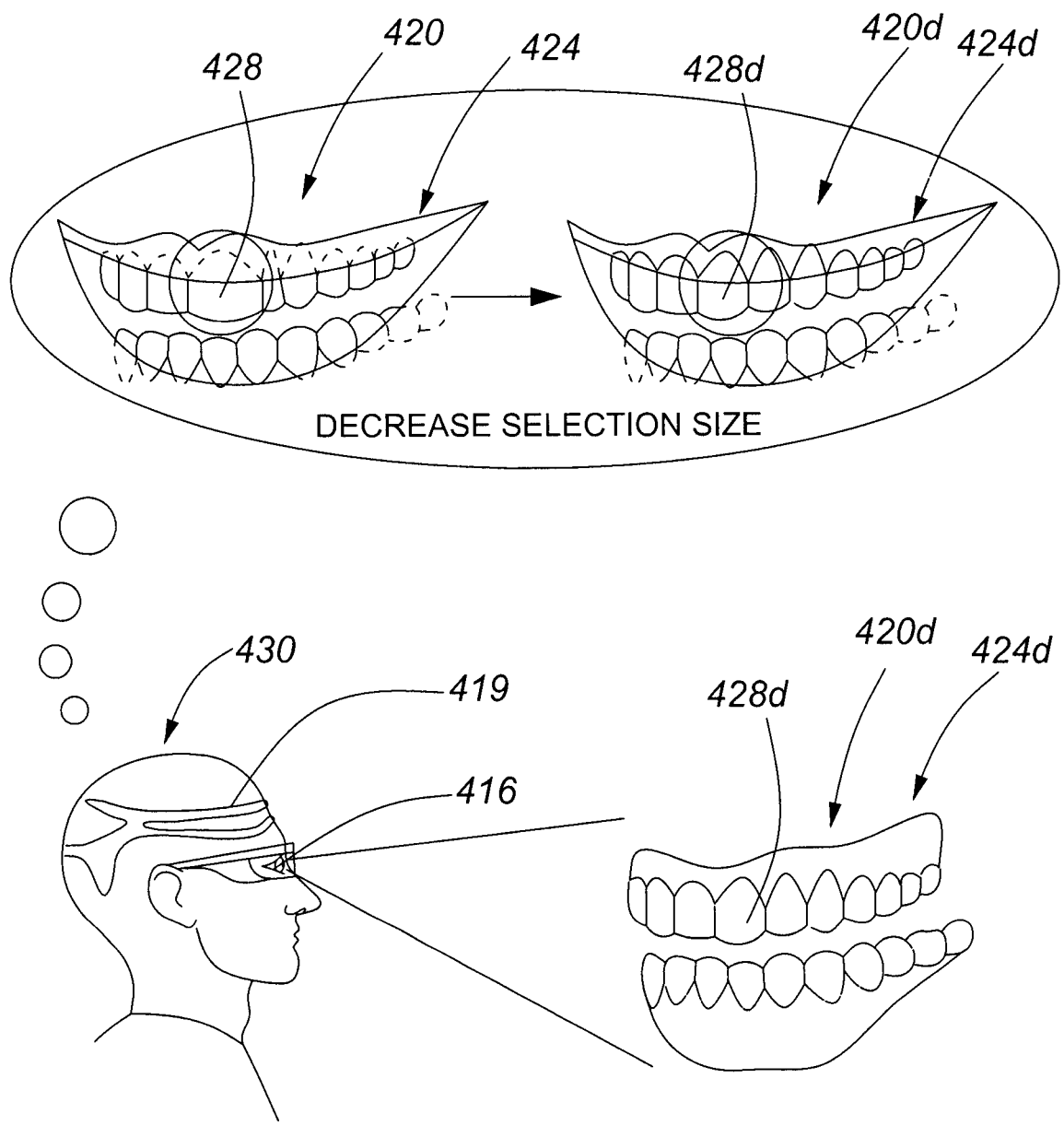
FIG. 27 is the individual decreasing the size of one tooth in the 3D model.

FIGS. 26 and 27 illustrate the individual 430 respectively enlarging and shrinking a single tooth 428 by conceptualizing selection of the single tooth 428 and changes in size of the single tooth 428.

Involuntary Response Data

Figure 28:
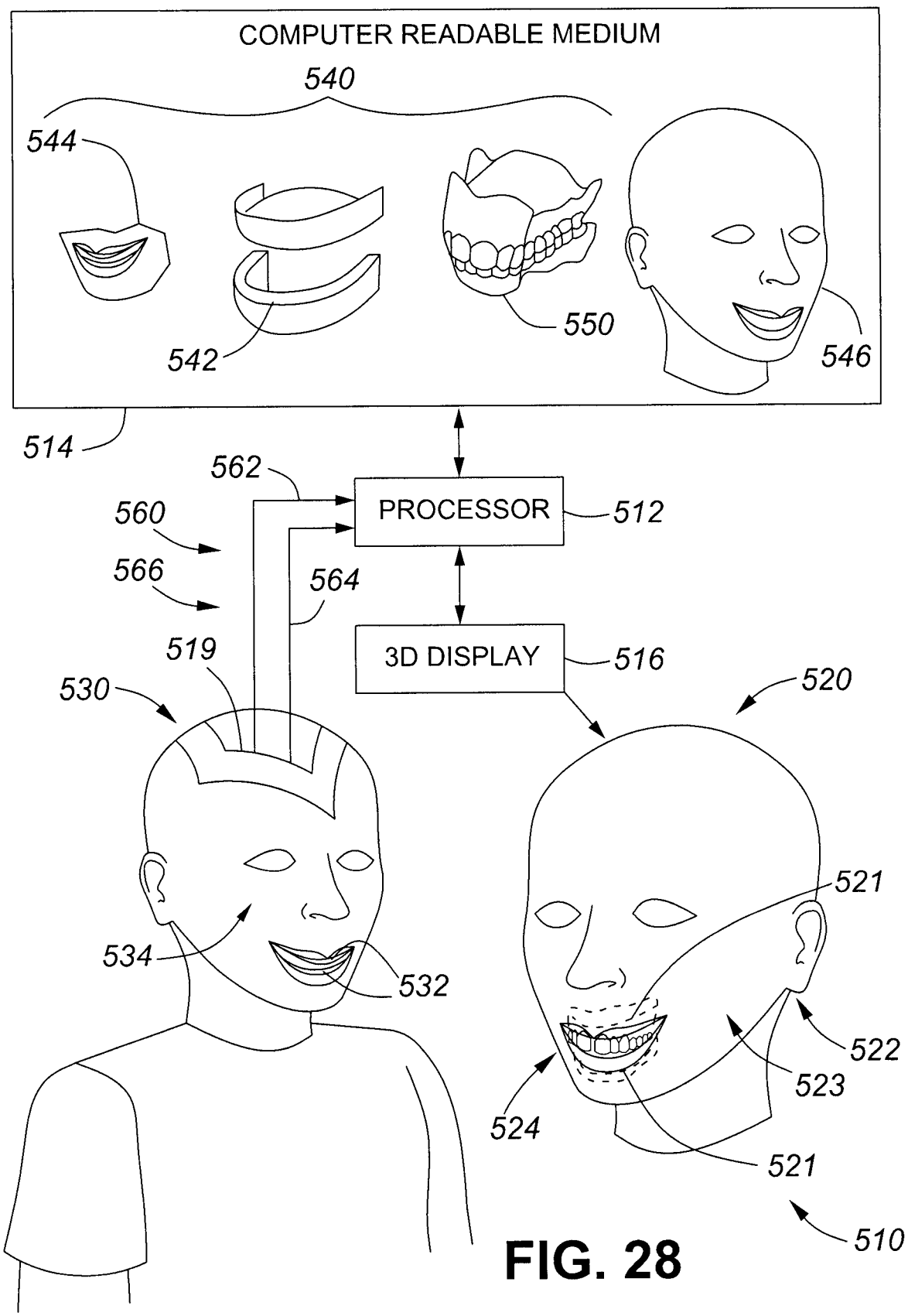
FIG. 28 is schematic of a system for displaying and manipulating a 3D model of an edentulous individual.

FIG. 28 shows a system 510 wherein the BCI 519 receives inputs of the neural activity data 566 corresponding to emotions, reactions, or other involuntary responses of the individual 530, providing involuntary response data 564 of the individual 530. With reference to the involuntary response data 564 and with calibration, the BCI 519 facilitates assessment of the emotional states and reactions of the individual 530, which in turn may facilitate predicting preferences of the individual 530 with respect to the proposed dental appliance 524.

The BCI 519 facilitates receiving inputs corresponding to facial expressions of the individual 530, either as voluntary action data 562 or involuntary response data 564. The individual 530 need not actually smile or otherwise change facial expressions to trigger the update to the 3D model 520. As with the neural activity data 566 of conceptualized hand gesture inputs detected by the BCI 519, neural activity data 566 corresponding to facial expressions need only be conceptualized, whether voluntary action data 562 of voluntary facial expressions or involuntary response data 564 of involuntary facial expressions. Facial expressions originate as nerve impulses in the brain, which travel through motor neurons to a neuromuscular junction. Upon adequate stimulation, the motor neuron releases a flood of neurotransmitters that bind to postsynaptic receptors and trigger a response in the muscle fiber which results in muscle movement. The BCI 519 facilitates responsive and intuitive changes to the 3D model 520 based on emotions or other factors (e.g. request to view celebrity smile, voluntary or involuntary adopting or conceptualizing a given facial expression, etc.).

The external feature data 546 may include empirical optical image data which is correlated to neural activity data 566 from the BCI 519 by the processor 512. The 3D model 520 may be updated in real-time in response to the neural activity data 566 (e.g. to show a smile, frown, close one eye, etc.). For example, the 3D model 520 may be updated to assume a saved position 526 corresponding to a smile in response to the individual 530 smiling and generating neural activity data 566 from the smile (whether voluntary action data 562 or involuntary response data 564). Since the external feature data 546 has already been acquired based on the external features 534, the facial expression or other update based on data from the BCI 519 would not necessarily correspond to the particular smile the individual 520 is presently making. Rather, the update to the 3D model 520 would be based on previously acquired scanned features data 540 corresponding to the relevant command (e.g. smile, frown, close one eye, etc.). The previously acquired scanned features data 540 may be included with the saved positions 526. The system 1010 of FIG. 35 and the system 1110 of FIG. 36 include extraoral optical scanners for adding additional data to the external features data during use of the systems.

The processor 512 may be programmed to assess and quantify involuntary response data 564 corresponding to different hypothetical dental design elements of the proposed dental appliance 524 (tooth shape and size, arrangement, shade, imperfections, etc.). The augmented reality data 550 can be organized in a hierarchical order of preferences specific to the individual 530 based on the involuntary response data 564. The order of preferences may be based on preference criteria such as an emotional state of the individual 530 or a voluntary input from the individual 530 (or another individual; e.g. the second individual 690, the second individual 790, the second individual 890, etc.). A preference criterion based on an emotional state equates the involuntary response data 564 to an emotional state to determine whether the 3D model 520 as displayed elicits a defined emotional response from the individual 530. The response may be binary or more nuanced as described below in relation to statistical models which may be applied to the involuntary response data 564. A preference criterion based on a voluntary input from the individual 530 measures the involuntary response data 564 against guidelines or constraints which are voluntarily selected by a user of the system 510 (e.g. the dentition 525 not exceed a given width or spacing on the front teeth, overbite necessary, underbite necessary, etc.). The guidelines may be applied by the individual 530 or by another person (e.g. the second individual 690, the second individual 790, the second individual 890, etc.).

The involuntary response data 564 may be fitted to a statistical model (e.g. an ordinal utility function may be estimated or interval preference data may be applied to provide an estimate of the component utility part-worth functions which can be statistically developed, etc.). The processor 512 can use the statistical model to recommend a proposed dental appliance 524 with a greater probability of approval by the individual 530, either by choosing a saved dental appliance 527 or by modifying the proposed dental appliance 524. Involuntary response data 564 facilitates assessment of reactions of the individual 530 to different arrangements of the proposed dental appliance 524 and quantification of the preferences of the individual 530. The statistical model may be a simple like/dislike model, or may include a variety of types of responses (e.g. nostalgia, happiness, confidence, excitement, indifference, disgust, etc.) of differing magnitudes and weighting factors, as has been well-known (e.g. with applications to preparing effective advertising, etc.).

As with the system 410, a system may also be prepared combining the features of the system 10 and the system 510, providing a system with both motion sensors and a BCI which responds to inputs of involuntary response data (not shown). Input from the motion sensors and from the BCI may be weighted differently. In addition, motion sensor input may be used to calibrate the BCI to the individual using such a system. Similarly, a system may be prepared combining the features of the system 510 and the system 1210, providing a system with two streams of involuntary response data from both a BCI and an optical or other sensor which responds to inputs of involuntary response data (not shown). Such a system would provide a cross-check for calibrating detection of the involuntary response data for the particular individual using the system.

Figure 29:
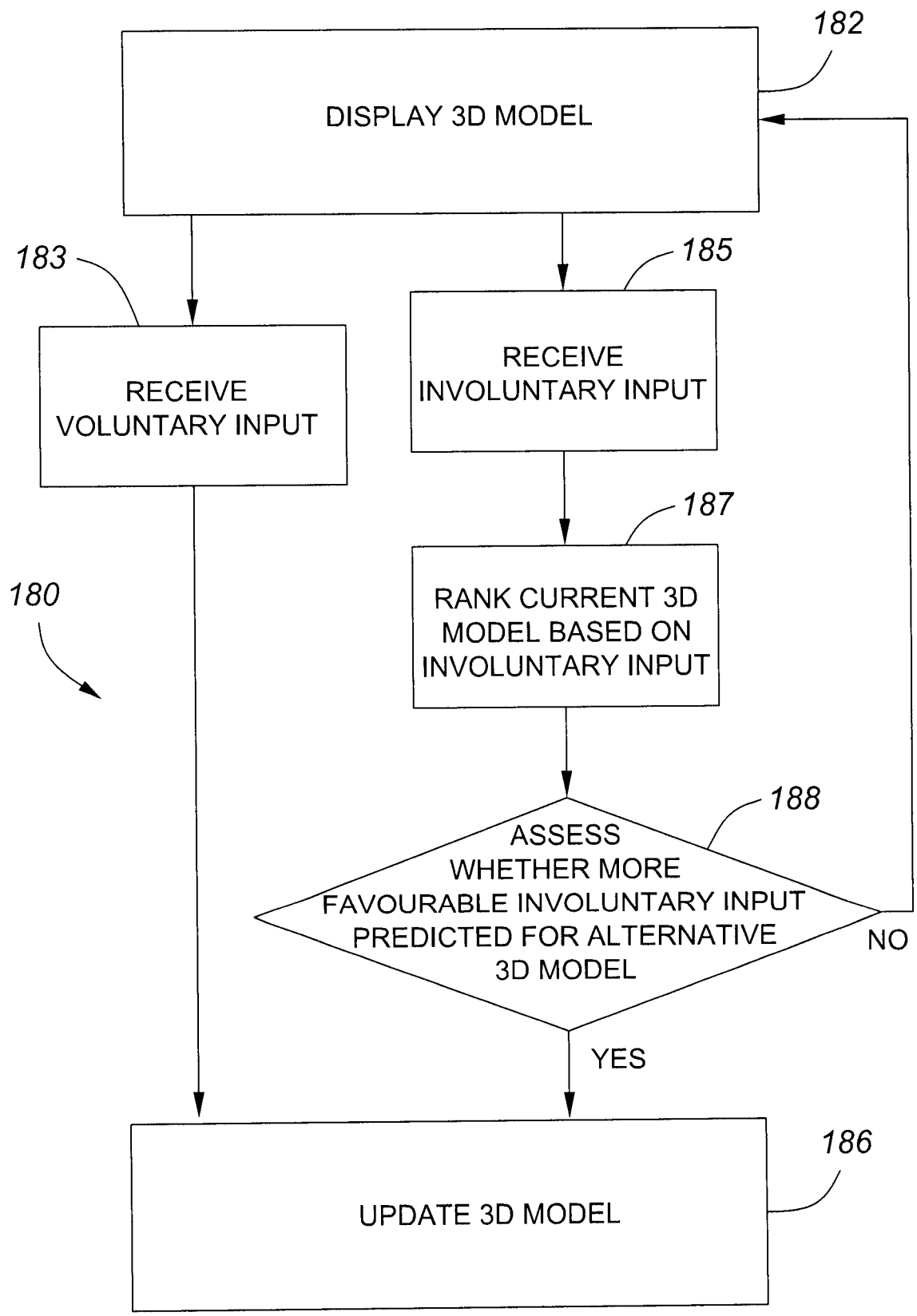
FIG. 29 is a flow chart of a method for displaying and manipulating the 3D model of FIG. 28.

FIG. 29 shows a method 180 of working with a 3D model using both voluntary action data inputs and involuntary response data inputs (e.g. with the 3D model 520, the 3D model 620, the 3D model 1220, etc.). The method 180 includes displaying the 3D model 182, receiving an input of voluntary action data 183, and updating the 3D model 186 in response to receiving an input of voluntary action data 183. The method 180 also includes receiving an input of involuntary response data 185 and ranking the current 3D model as displayed based on the involuntary response data

187. Once ranking the 3D model as displayed based on the involuntary response data 187 is complete, the method 180 applies an algorithm for assessing whether changes to the 3D model are likely to elicit a more positive involuntary response 188. If the algorithm indicates that changes to the 3D model are not likely to elicit a more positive involuntary response than the data resulting from receiving an input of involuntary response data 185, the method 180 returns to displaying the 3D model 182 until either of receiving an input of voluntary action data 183 or receiving an input of involuntary response data 185 occurs.

If the algorithm indicates that changes to the 3D model are likely to elicit a more positive involuntary response than the data resulting from receiving an input of involuntary response data 185, the method proceeds to updating the 3D model 186 in response to receiving an input of involuntary response data 185. In this case, updating the 3D model 186 applies the changes that are likely to elicit a more positive involuntary response than the data resulting from receiving an input of involuntary response data 185. Updating the 3D model 186 in response to receiving an input of involuntary response data 185 may be subject to the user approving updating of the 3D model 186, or may occur automatically upon determining whether changes to the 3D model are likely to elicit a more positive involuntary response 188. The method 180 may be performed using the processor 512 with reference to data stored in the computer readable medium 514 of the system 510, with the corresponding features of the system 610, the system 1210, or with any system including a sensor to detect involuntary response data.

The step of receiving an involuntary input 185 may be from a BCI, an optical scanner, other sensors for detecting pupil dilation, pulse, and other factors to assess emotional state, a polygraph combining such sensors, or any other suitable approach to measuring the emotional state and preferences of the individual providing the involuntary input.

In an application of the method 180, the individual 30 may have a better reaction to, for example, the right side of their smile than to the left side. The individual 30's preference for any design elements present on the right side, but missing from the left side would be ranked, and proposed alterations could be recommended to a proposed dental appliance to provide increase the chances of a positive emotional reaction. These responses may be binary response or more detailed in terms of how much the individual 30 likes the 3D model 20 as displayed compared to other options, and design software could suggest design elements to incorporate or leave out based on preferences, design elements that cannot coexist in the same design, constraints, and other factors.

The method 180 depends on the quality of data (e.g. from a BCI, optical emotion detector, polygraph, etc.). An applicable algorithm may be based on an ordinal utility function estimation, interval preference data (with a statistically-developed estimate of the component utility part-worth functions), etc. Developments of BCIs will further increase the accuracy of such algorithms to provide every more accurate preferential information.

Use by Two Individuals

FIG. 30 shows a system 610 wherein a second non-subject individual 690 is engaged with the BCI 619. The BCI 619 receives the neural activity data 666 from the individual 630, second neural activity data 676 from the second individual 690, or both. The neural activity data 666 may include the voluntary action data 662, the involuntary response data 664, or both. The second neural activity data 676 may include second voluntary action data 672, second involuntary response data 674, or both.

The second voluntary action data 672 and second involuntary response data 674 may be received by the BCI 619 and applied as mental commands, emotional states, reactions or other neural activity of the second individual 690. In contrast, the system 510 receives voluntary action data 562 and involuntary response data 564 from the individual 530 or from a non-subject individual (not shown) only. However, contemporaneous control by, and the opinion of, the second individual 690 (e.g. a spouse, partner, family member, confidant, etc.) is often also valuable (e.g. when the individual 630 is visually impaired, is uncommunicative, etc.). The processor 612 may be configured in a variety of manners to differently respond to the neural activity data 666, the second neural activity data 676, or both. In this way the method 180 may be practiced wherein receiving an input of voluntary action data 183 and receiving an input of involuntary response data 185 are each applied to the first input data 660, the second input data 670, or both, and with any appropriate weighting as between the first input data 660 and the second input data 670.

The processor 612 may be configured to respond to both voluntary action data 662 and second voluntary action data 672, and weigh both involuntary response data 664 and second involuntary response data 674 when preparing a proposed dental appliance 624. This configuration would facilitate control by, and ranking of the proposed dental appliance 624 in response to the reactions of, both the individual 630 and the second individual 690. The involuntary response data 664 and second involuntary response data 674 may be weighted differently.

The processor 612 may be configured to respond to both voluntary action data 662 and second voluntary action data 672, but weigh only involuntary response data 664 or second involuntary response data 674 when preparing a proposed dental appliance 624. This configuration would facilitate control by both the individual 630 and the second individual 690, but provide suggestions and measure the involuntary responses of only one of the individual 630 or the second individual 690.

The processor 612 may be configured to respond to only one of voluntary action data 662 or second voluntary action data 672, but weigh both involuntary response data 664 and second involuntary response data 674. This configuration would facilitate control by only one of the individual 630 or the second individual 690, but would account for the involuntary responses of both the individual 630 and the second individual 690 when preparing a proposed dental appliance 624. The involuntary response data 664 and second involuntary response data 674 may be weighted differently.

The processor 612 may be configured to respond to only the second voluntary action data 672, and weigh only the second involuntary response data 674. This configuration would facilitate control by the second individual 690, and would result in a proposed dental appliance 624 selected with reference to only second involuntary response data 674.

The processor 612 may be configured to respond to only the voluntary action data 662, and weigh only the second involuntary response data 674. This configuration would facilitate control by only of the individual 630, and would result in a proposed dental appliance 624 selected with reference to only the second involuntary response data 674.

The processor 612 may be configured to respond to only the second voluntary action data 672, and weigh only the involuntary response data 664. This configuration would facilitate control by the second individual 690 only, and would result in a proposed dental appliance 624 selected with reference to only the involuntary response data 664.

Figure 31:
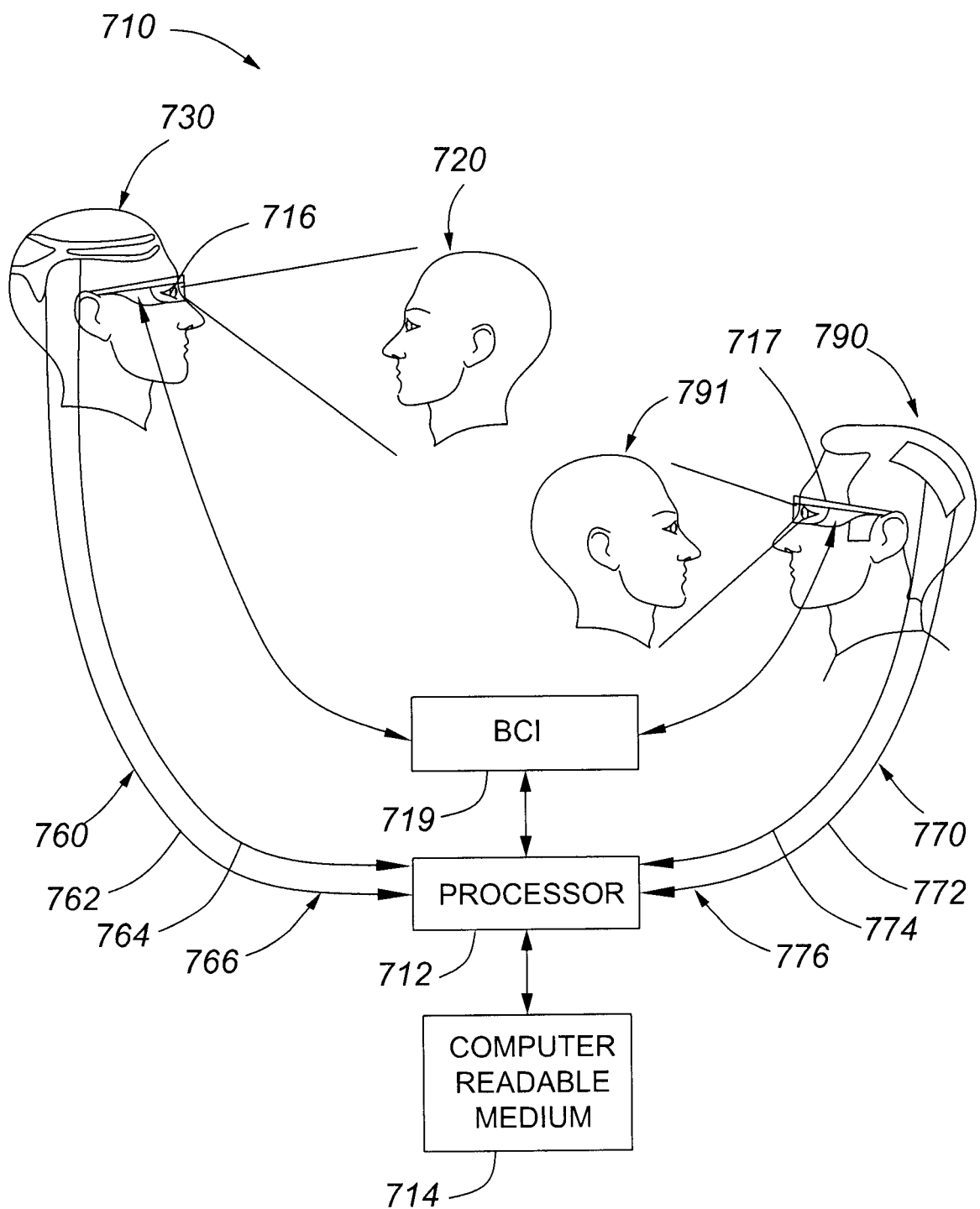
FIG. 31 is a schematic of a system for displaying and manipulating two 3D models of an edentulous individual.

FIG. 31 is a system 710 wherein the individual 730 and the second individual 790 each provide input data to the BCI 719. The individual 730 views the 3D model 720 on the 3D display 716 and manipulates the 3D model 720 through the BCI 719 by inputting the first input data 760. A second 3D model 791 of the individual 730 is displayed for the second individual 790 on a second 3D display 717. The second individual 790 views the second 3D model 791 on the second 3D display 717 and manipulates the second 3D model 791 through the BCI 719 by inputting the second input data 770. Application of the first input data 760 with respect to the 3D model 720 and of the second input data 770 with respect to the second 3D model 791 may each be as described elsewhere in this application. The individual 730 may provide voluntary action data 762, involuntary response data 764, or both, for manipulating the 3D model 720. Similarly and independently of the individual manipulating the 3D model 720, the second individual 790 may provide voluntary action data 772, involuntary response data 774, or both, for manipulating the second 3D model 791. Alternatively, the involuntary response data 764 may be applied to a method similar to that of method 180 in respect of the second 3D model 791, or the second involuntary response data 774 may be applied in respect of the 3D model 720.

Figure 32:
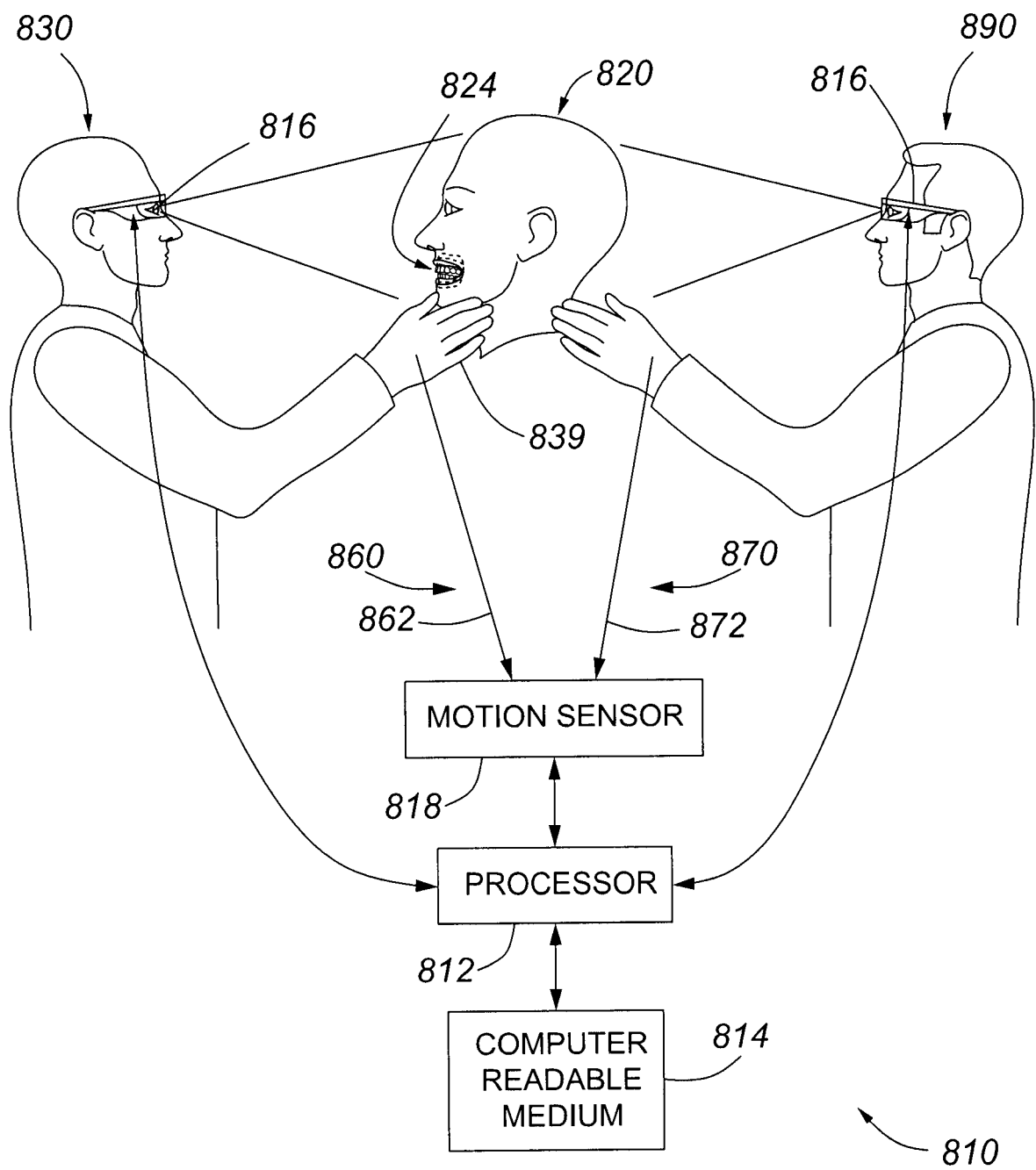
FIG. 32 is a schematic of a system for displaying and manipulating a 3D model of an edentulous individual.

FIG. 32 is a system 810 wherein the individual 830 and the second individual 890 each interact with the 3D model 820 through a motion sensor 818. The processor 812 may include instructions to allow both the individual 830 and the second individual 890 to freely interact with the 3D model 820, to bias towards one of the individual 830 and the second individual 890, to allow the individual 830 and the second individual 890 to take turns, or any suitable arrangement.

A system may also be prepared combining the features of the system 810 and the system 610, providing a system with both motion sensors and a BCI for one or both of the individual and the second individual (not shown). Such a system may also be prepared wherein separate 3D models are displayed and manipulated by the individual and the second individual, similarly to the system 710.

Acquisition of Scanned Feature Data

Figure 33:
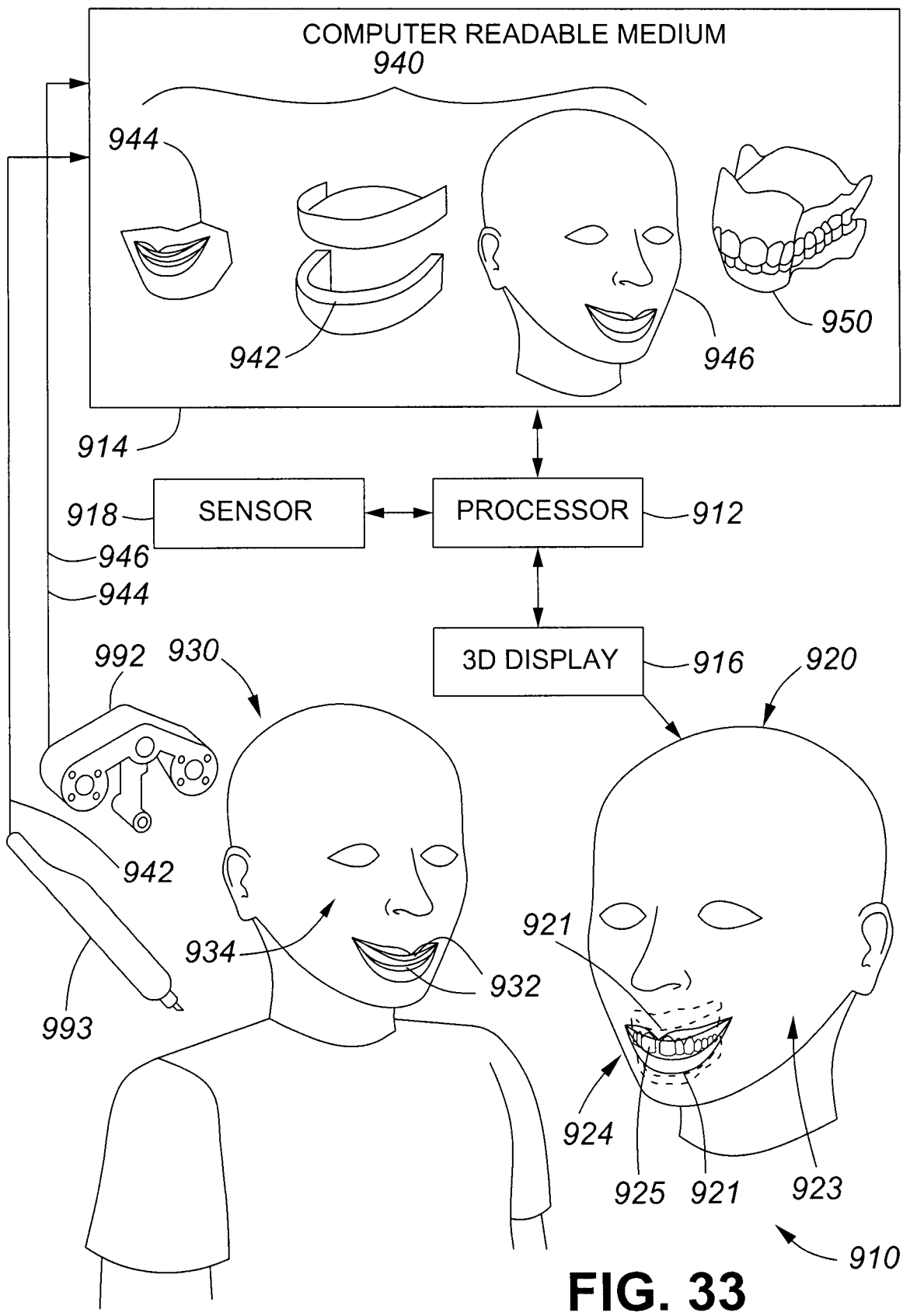
FIG. 33 is a schematic of a system for acquiring data to prepare a 3D model of an edentulous individual, and displaying and manipulating a 3D model.

FIG. 33 is a system 910 which includes scanners in communication with the computer readable medium 914 for acquiring the scanned features data 940. An intraoral optical scanner 993 is for acquiring the arches data 942 from the maxillary and mandibular dental arches 932. An extraoral optical scanner 992 is for acquiring the relational data 944 from the maxillary and mandibular dental arches 932 and the external features 934. The extraoral optical scanner 992 is also for acquiring the external features data 946 from the external features 934. Including the scanners in the system 910 facilitates acquiring the scanned features data 940 and using the 3D model 920 at the same location. The scanned features data 940 is provided from the extraoral optical scanner 992 and the intraoral optical scanner 993 to the computer readable memory 914 by any method using a wired connection, wireless connection, transfer of removable media, etc.

The external features data 946 may be acquired with or without a denture or other appliance in the mouth of the individual 930. Acquiring the external features data 946 with a denture or other appliance in the mouth of the individual 930 which approximates the proposed dental appliance 924 may improve modeling of the external features 934, as affected by a proposed dental appliance 924. The additional external features data 946 may improve modeling accuracy of proposed restorations. Existing dentures or bite rims could be placed in the mouth during external facial data capture, at different facial expressions, to improve the relationship between the proposed dental appliance 924 and the resultant modelled external features 923. Temporary material (e.g. dental wax, etc.) could be added to existing dentures to approximate an improved denture which is closer to the expected proposed dental appliance 924.

Figure 34:
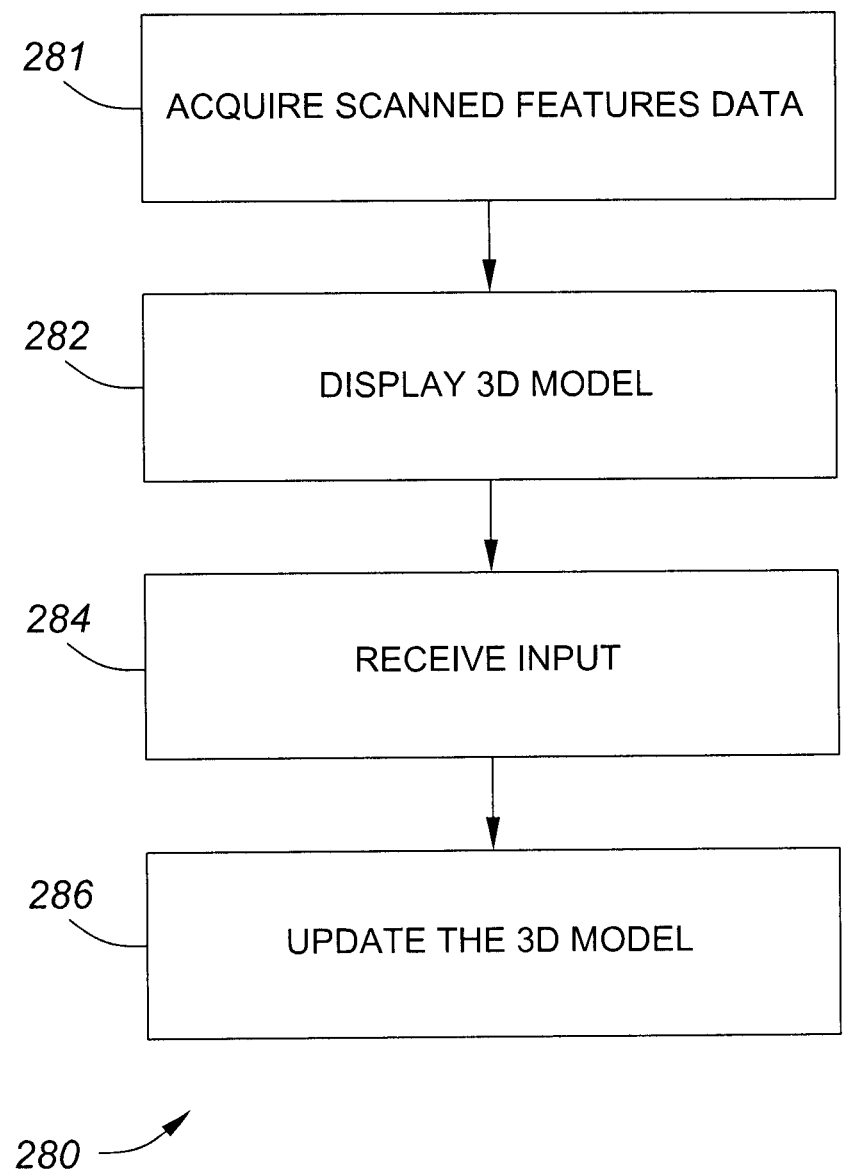
FIG. 34 is a flow chart of a method for acquiring data for, displaying, and manipulating the 3D model of FIG. 33.

FIG. 34 shows a method 280 for acquiring data for, displaying, and manipulating a 3D model. The method 280 includes acquiring the scanned features data 281, displaying the 3D model 282, receiving an input 284, and updating the 3D model 286 in response to receiving an input 284. The method 280 may be performed using the system 910. Displaying the 3D model 282 and updating the 3D model 286 may be completed on the 3D display 916 by execution of instructions by the processor 912 using data from acquiring the scanned features data 281, and which is stored in the computer readable medium 914. Receiving an input 284 may include detection of a hand gesture by the motion sensor 918 of the system 910, other voluntary inputs, involuntary inputs, or combinations of inputs.

Figure 35:
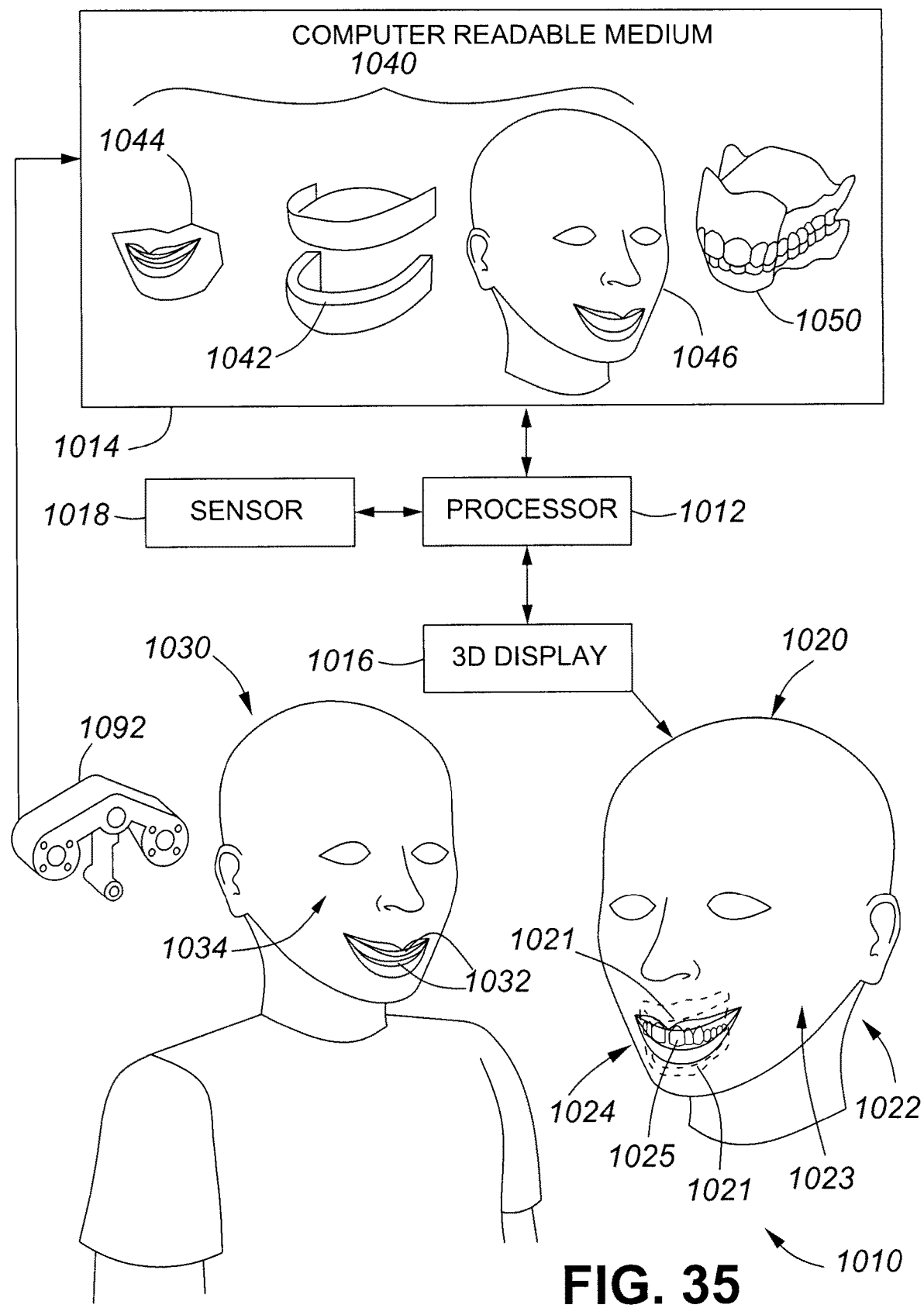
FIG. 35 is a schematic of a system for acquiring data to prepare a 3D model of an edentulous individual, displaying and manipulating a 3D model, and updating the 3D model.

FIG. 35 is a system 1010 which includes the extraoral optical scanner 1092 for updating the external features data 1046. The extraoral optical scanner 1092 may be a standalone unit as shown, or may be included as an outward-facing imaging sensor on the 3D display 1016 (e.g. a Leap or Kinect camera system and a projected holography/overlay element, etc.). The extraoral optical scanner 1092 may be used while the 3D model 1020 is being manipulated to acquire additional external features data 1046 for use in the 3D model 1020.

Figure 36:
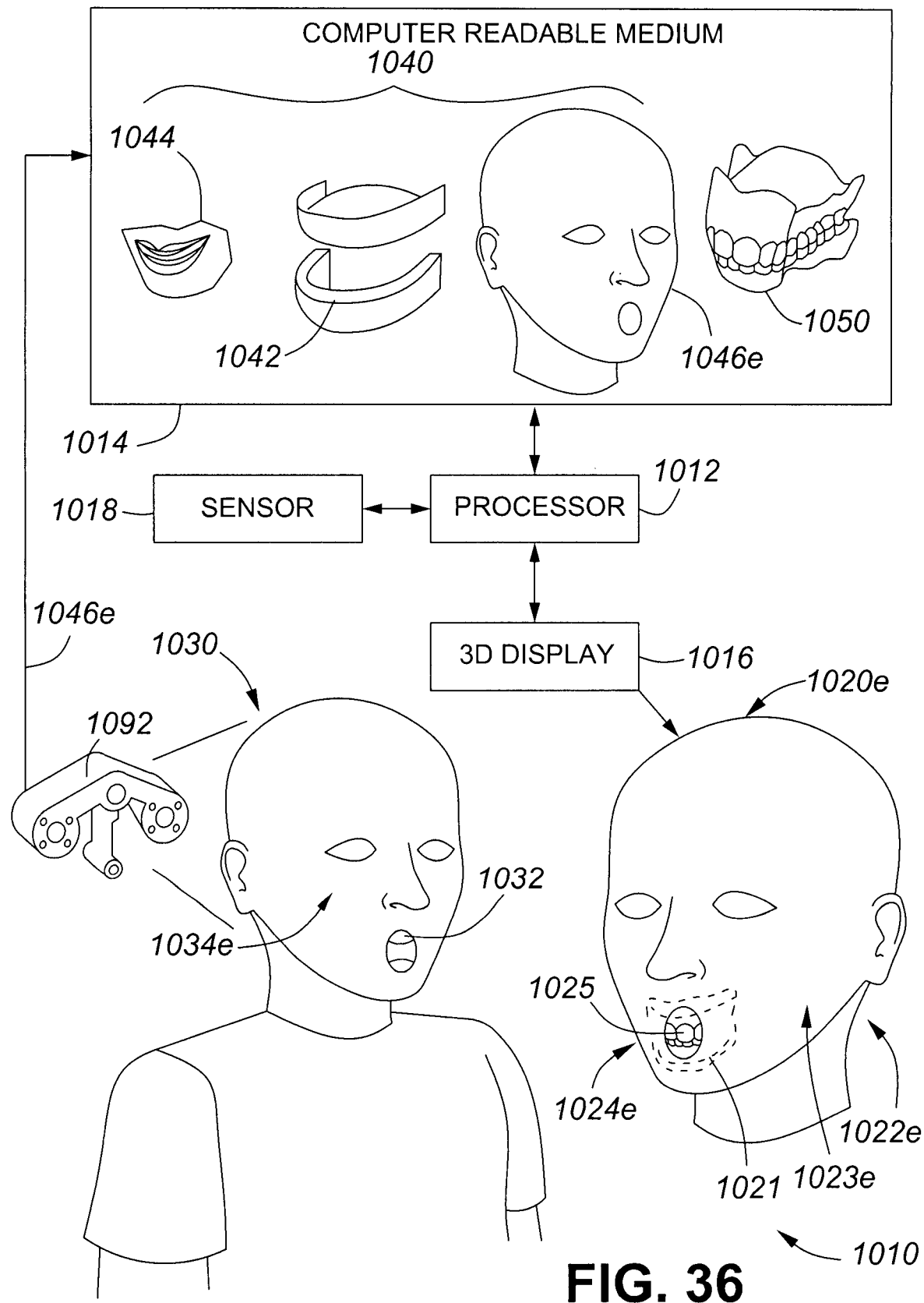
FIG. 36 is the system of FIG. 35 after updating external features data.

FIG. 36 is the system 1010 acquiring updated external features data 1046e from the individual 1030 in a pose having updated external features 1034e, which differ in appearance from the external features 1034 of FIG. 35 in that the individual 30 is adopting a different facial expression. The extraoral optical scanner 1092 is scanning the updated external features 1034e and providing the resulting updated external features data 1046e to the computer readable medium 1014 for use by the processor 1012 to render the updated 3D model 1020e having updated subject features 1022e, which include updated modeled external features 1023e. The 3D model 1020e is based on empirical data of the updated modeled external features 1023e, which may facilitate more accurate modelling of the updated modeled external features 1023e compared with moving the 3D model 1020 to a facial expression approximating that shown by the updated external features 1034e but without empirical data.

During use of the system 1010, the individual 1030 may decide that a given facial expression as shown on the 3D model 1020 would benefit from empirical data to more accurately reflect the appearance of the individual 1030 at the given facial expression. The individual may change their facial expression to the updated external features 1034e and activate the extraoral optical scanner 1092 to acquire the updated external features data 1046e, which is stored in the computer readable medium 1014. The processor 1012 updates the 3D model 1020 to include the updated external features data 1046e, providing the updated 3D model 1020e. The updated 3D model 1020e may be saved as a saved position 1026. The individual 1030 may include dentures on their maxillary and mandibular arches 1032 prior to acquiring the updated external features data 1046e where the facial expression would benefit from dentition (not shown).

Figure 37:
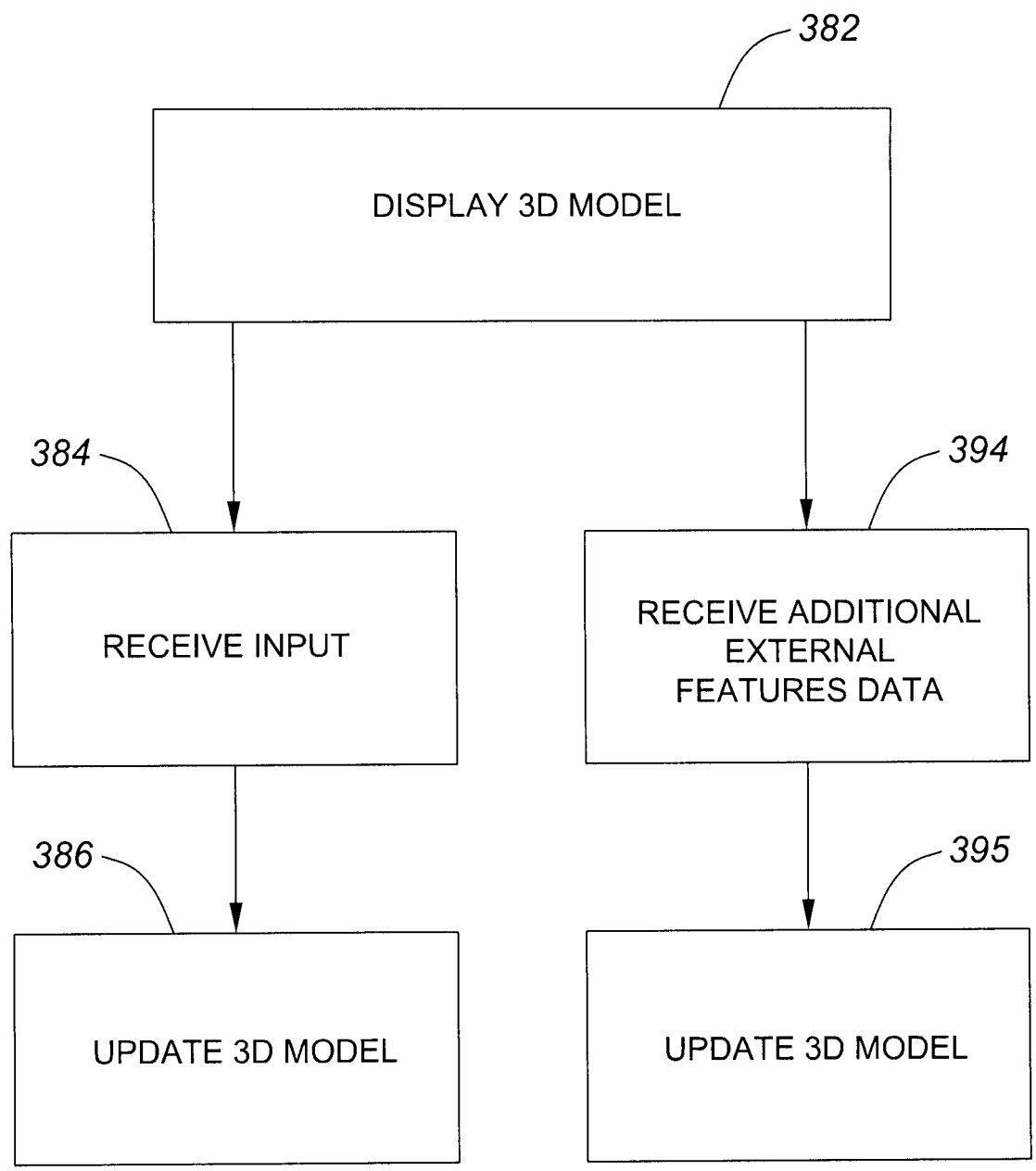
FIG. 37 is a flow chart of a method for displaying, manipulating, and updating the 3D model of FIG. 35.

FIG. 37 shows a method 380 of working with and updating a 3D model. The method 380 includes displaying the 3D model 382, receiving an input 384, and updating the 3D model 386 in response to receiving an input 384. In addition, the method 380 includes receiving additional external features data 394 and updating the 3D model in response to the additional external features data 395. The method 380 may be performed using the system 1010. Displaying the 3D model 382, updating the 3D model 386, and updating the 3D model in response to the additional external features data 395 may be completed on the 3D display 1016 by execution of instructions by the processor 1012 using data stored in the computer readable medium 1014, including the updated external features data 1046e. Receiving an input 384 may include detection of a hand gesture by the motion sensor 1018 of the system 1010, other voluntary inputs, involuntary inputs, or combinations of inputs.

The system 1010 may be used to continuously acquire the updated external features data 1046e, resulting in real-time updating of the 3D model 1020 to reflect the current facial expression of the individual 1030. This application of the system 1010 results in practicing the method 380 in real-time, and effectively allows the individual 1030 to view and manipulate a real-time augmented reality mirror showing the model 1020 in the same facial expression that the individual 1030 is currently holding, adjusted for the presence of the proposed dental appliance 1024. The real-time data acquisition and modelling could be on continuously, or transiently applied as selected by the individual 1030.

Figure 38:
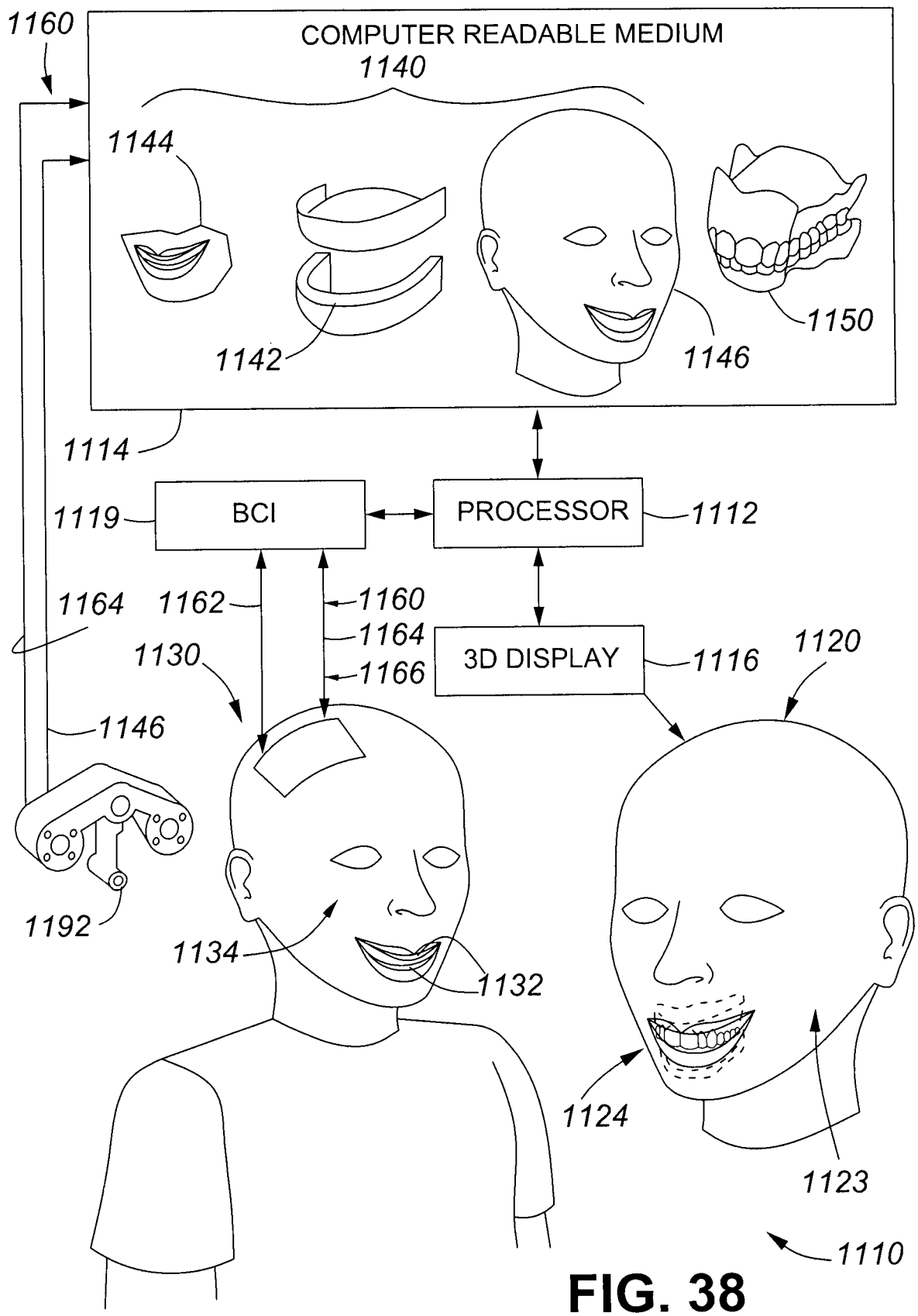
FIG. 38 is a schematic of a system for acquiring data to prepare a 3D model of an edentulous individual, displaying and manipulating a 3D model, and updating the 3D model.

FIG. 38 is a system 1110 including the extraoral optical scanner 1192 and the BCI 1119. The BCI 1119 may facilitate predictive acquisition of additional external features data 1146 and updating of the 3D model 1120 to include additional external features data 1146 in real time, or at given emotional or other states which affect the external features 1134 that are to be reflected in the modeled external features 1123, resulting in empirical data of a given facial expression, facilitating more accurately modelling of the facial expression by the 3D model 1120.

The BCI 1119 may also facilitate a comparison of the neural activity data 1166 with the additional external feature data 1146. The comparison may facilitate accurate correlation of the neural activity data 1166 with emotional states that may be recognized in the additional external features data 1146. In addition, real-time updating applications of the system 1110 may be facilitated compared with non-BCI equipped systems, such as the system 1010. The BCI 1119 may provide feedback on emotional response during precise moments of contemplation.

Figure 39:
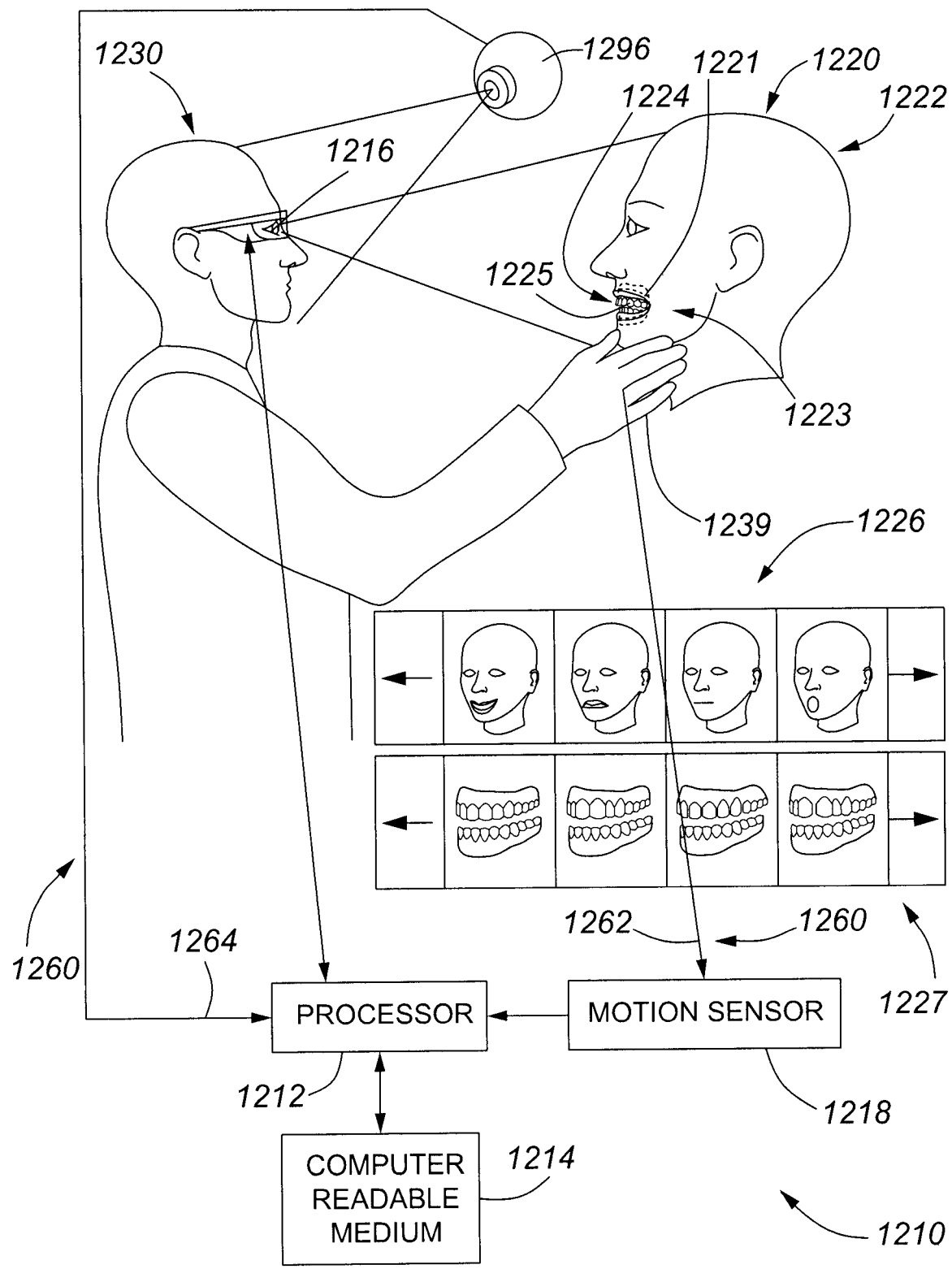
FIG. 39 is a schematic of a system for displaying and manipulating a 3D model of an edentulous individual.

FIG. 39 is a system 1210 wherein the involuntary response data 1264 is received without application of a BCI. The involuntary response data 1264 may be acquired through an optical sensor 1296 which detects facial expressions and other movements of the individual 1230 relevant to the emotional state of the individual 1230. The optical sensor 1296 may be directed to detecting microexpressions, pupil dilation, and other reliable indicators for the emotional state of the individual 1230, alone or in combination. In addition, other scanners which are not optical may receive the involuntary response data 1264 (not shown; e.g. a pulse meter, temperature gauges, etc.), and the involuntary response data 1264 may be received by a combination of multiple types of data (not shown; e.g. a polygraph of temperature, pulse, and pupil dilation, etc.). Other than the involuntary response data 1264 being acquired without the use of a BCI, the system 1210 functions similarly to the system 510, including with respect to the involuntary response data 1264 triggering a saved position 1226.

A system may also be prepared combining the features of the system 510 and the system 1210, providing a system with both an optical sensor (or other suitable non-BCI sensor; e.g. a polygraph of temperature, pulse, and pupil dilation, etc.) and a BCI (not shown). Input from the BCI and from the other sensor may be weighted differently. In addition, input from the other sensor may be used to calibrate the BCI to the individual using such a system.

The same hardware may perform the functions of the motion sensor (e.g. the motion sensor 18, the extraoral optical scanner 992, and the optical sensor 1296). Generally, scanners for acquiring the scanned features data may be more costly and subject to additional engineering bottlenecks compared with scanners for acquiring the first input data. However, a single scanner (optical or otherwise) may be applied available to acquire the scanned features data, the voluntary action data, and the involuntary response data, without departing from the methods and systems described herein.

Figure 40:
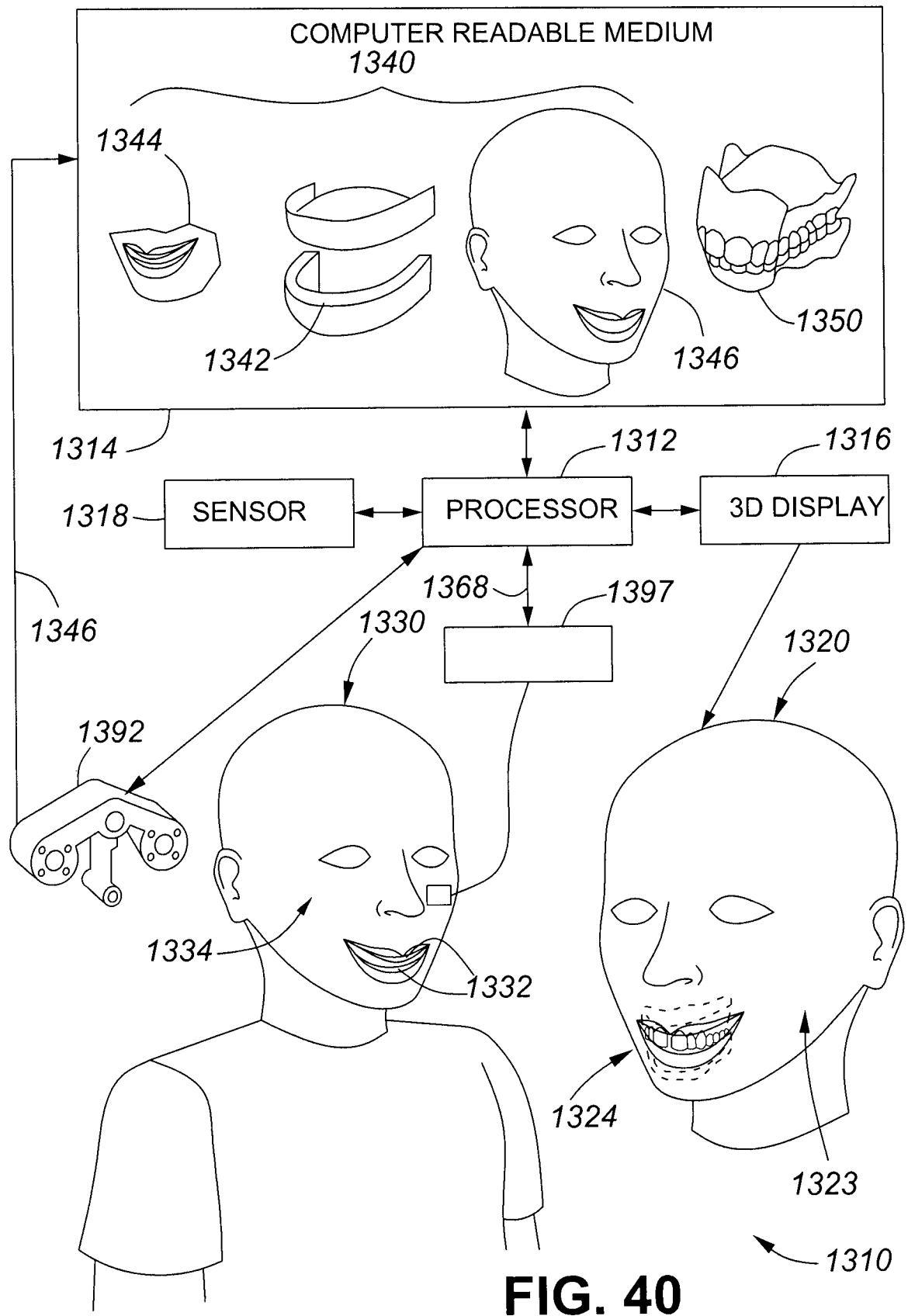
FIG. 40 is a schematic of a system for acquiring data to prepare a 3D model of an edentulous individual, displaying and manipulating a 3D model, and updating the 3D model.

FIG. 40 shows a system 1310 wherein a muscle activity sensor 1397 is engaged with the individual 1330 to measure activity of the individual 1330's jaw musculature. The muscle activity sensor 1397 may for example be an electromyography module. The system 1310 includes the extraoral scanner 1392 for acquiring additional external features data 1346. The muscle activity sensor 1397 detects when the muscle usage in jaw muscles of the individual 1330 is at a minimum, and sends a signal to the processor 1312 to direct the extraoral scanner 1392 to acquire additional external features data 1346. As such, acquisition of the external features data 1346 may be acquired at the rest position. In addition, a transcutaneous electrical nerve stimulation module may be applied to the individual's jaw musculature to exhaust the jaw musculature and force the maxillomandibular relationship to the rest position.

The 3D model 1320 may be used to check bite information. For an edentulous individual 1330, this would be possible with either nothing in their mouth, only an upper bite rim, or upper and lower bite rims or dentures (so long as the intraoral objects do not contact each other prior to the desired bite location). As the individual 1330 closes their jaw, the processor 1312 would facilitate determination of whether the individual 1330 is biting in the proper occlusal position, which could be used as further confirmation of the scanned features data 1340. As with WO 2013/071435, which shares an inventor with this application, electromyography to assess facial muscle activity at various positions, or transcutaneous electrical nerve stimulation to force the rest position, each facilitate acquisition of data in the rest position. This information could be considered when defining appropriate constraints within which the individual 1330 can make adjustments while keeping the physiological aspects of the bite consistent.

In some cases, imaging includes only maxillary data only. No bite information is required to model only upper front teeth. This does not change the data acquisition inputs, aside from foregoing the mandibular portion of the arches data and the portion of the relational data that relating to the mandibular arch.

Examples Only

In the preceding description, for purposes of explanation, numerous details are set forth to provide a thorough understanding of the embodiments. However, it will be apparent to one skilled in the art that these specific details are not required. In some instances, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

What is claimed is:

1. A method of designing a dental appliance for a subject individual comprising:
   displaying a 3D model of the subject individual on a 3D display, the 3D model comprising:
   a scanned feature comprising a dental arch of the subject individual, and a portion of a face of the subject individual and the arch for relating the arch to the face; and
   an augmented reality feature comprising a dental appliance for the subject individual;
   detecting a voluntary input with at least one sensor, wherein the voluntary input comprises at least one skilled input from an individual skilled in dental design and at least one layperson input from a layperson individual;
   modifying the dental appliance in response to the skilled input, the layperson input or both to provide a modified dental appliance;
   repositioning the scanned feature in response to the modified dental appliance to provide a repositioned scanned feature;
   updating the 3D model in response to the modified dental appliance and the repositioned scanned feature to provide an updated 3D model; and
   displaying the updated 3D model on the 3D display.

2. The method of claim 1 wherein the voluntary input comprises a gesture-based input.

3. The method of claim 2 wherein the gesture-based input comprises gripping a feature of the 3D model on the 3D display and manipulating the feature.

4. The method of claim 3 wherein gripping the feature comprises gripping the feature with a hand.

5. The method of claim 3 wherein the feature comprises dentition of the dental appliance.

6. The method of claim 5 wherein manipulating the feature comprises changing angulation of the dentition.

7. The method of claim 2 wherein the gesture-based input originates from the subject individual.

8. The method of claim 2 wherein the gesture-based input originates from a non-subject individual.

9. The method of claim 2 wherein the at least one sensor comprises a motion sensor.

10. The method of claim 1 wherein the voluntary input comprises a neural activity input, and the at least one sensor comprises a brain-computer interface.

11. The method of claim 10 wherein the neural activity input comprises a conceptualization of the modified dental appliance.

12. The method of claim 10 wherein the neural activity input comprises a conceptualization of modifying the dental appliance.

13. The method of claim 12 wherein conceptualization of modifying the dental appliance comprises conceptualizing gripping a feature of the 3D model on the display with a hand and manipulating the feature.

14. The method of claim 10 wherein the feature comprises dentition of the dental appliance.

15. The method of claim 14 wherein manipulating the feature comprises changing angulation of the dentition.

16. The method of claim 10 wherein the voluntary input comprises a gesture-based input, and the at least one sensor comprises a motion sensor.

17. The method of claim 10 wherein the neural activity input comprises neural activity input from the subject individual.

18. The method of claim 10 wherein the neural activity input comprises neural activity input from a non-subject individual.

19. The method of claim 1 wherein the voluntary input comprises constraining at least a portion of the scanned feature to a target position, and the modified dental appliance comprises a modified feature which facilitates the target position.

20. The method of claim 19 wherein the target position comprises a selected maxillomandibular relationship.

21. The method of claim 20 wherein the selected maxillomandibular relationship is a rest position, and the dentition provides a freeway space of between 1 and 4 mm at the rest position.

22. The method of claim 20 wherein the selected maxillomandibular relationship is at a selected occlusal position, and the dentition provides occlusion at the selected maxillomandibular relationship.

23. The method of claim 20 wherein the modified feature comprises dentition of the dental appliance.

24. The method of claim 1 further comprising:
   detecting an involuntary input with the at least one sensor;
   modifying the dental appliance in response to the involuntary input to provide the modified dental appliance;
   repositioning the scanned feature in response to the modified dental appliance to provide the repositioned scanned feature;
   updating the 3D model in response to the modified dental appliance and the repositioned scanned feature to provide the updated 3D model; and
   displaying the updated 3D model on the 3D display.

25. The method of claim 24 wherein the involuntary input comprises involuntary input from the subject individual.

26. The method of claim 24 wherein the involuntary input comprises involuntary input from a non-subject individual.

27. The method of claim 24 wherein the involuntary input comprises a neural activity input and the at least one sensor comprises a brain-computer interface.

28. The method of claim 24 wherein the involuntary input comprises a change in a facial expression and the at least one sensor comprises an optical sensor.

29. The method of claim 1 further comprising:
   detecting an involuntary input with the at least one sensor;
   correlating the involuntary input with a preference criterion and with the modified dental appliance to determine a preference of an individual;
   modifying the modified dental appliance to provide a suggested dental appliance correlated to the preference of the individual;
   repositioning the scanned feature in response to the suggested dental appliance to provide a suggested scanned feature;
   updating the 3D model in response to the suggested dental appliance and suggested scanned feature to provide a suggested 3D model; and
   displaying the suggested 3D model on the 3D display.

30. The method of claim 29 wherein the preference criterion comprises an emotional state of the individual.

31. The method of claim 29 wherein the preference criterion comprises a voluntary input of the individual.

32. The method of claim 29 wherein the involuntary input comprises involuntary input from the subject individual.

33. The method of claim 29 wherein the involuntary input comprises involuntary input from a non-subject individual.

34. The method of claim 29 wherein the involuntary input comprises a neural activity input and the at least one sensor comprises a brain-computer interface.

35. The method of claim 29 wherein the involuntary input comprises a change a facial expression and the at least one sensor comprises an optical sensor.

36. The method of claim 29 wherein the involuntary input is in response to the updated 3D model.

37. The method of claim 1 wherein the 3D model comprises a saved position, the saved position having a selected scanned feature of the face.

38. The method of claim 37 further comprising: repositioning the scanned feature to the saved position; updating the 3D model in response to the saved position and repositioned the scanned feature to provide a saved position 3D model; and displaying the saved position 3D model on the 3D display.

39. The method of claim 1 wherein the scanned feature comprises external feature data of the face for additional detail on the face in the 3D model.

40. The method of claim 39 wherein the external feature data of the subject individual's face comprises data for including substantially the entire face of the subject individual's face in the 3D model.

41. The method of claim 1 further comprising acquiring data of the scanned feature.

42. The method of claim 41 wherein acquiring data of the scanned feature comprises optically scanning the scanned feature.

43. The method of claim 41 wherein acquiring data of the scanned feature comprises ultrasonographically scanning the scanned feature.

44. The method of claim 41 wherein acquiring data of the scanned feature comprises acquiring additional data of the scanned feature in response to the voluntary input and updating the 3D model to include the additional data.

45. The method of claim 44 wherein acquiring additional data and updating the 3D model to include the additional data are each performed continuously and substantially in real-time.

46. The method of claim 44 wherein adoption of a facial expression by the subject individual results in updating the 3D model to include the additional data, and wherein the additional data includes external feature data of the subject individual adopting the facial expression.

47. The method of claim 46 wherein the voluntary input comprises a neural activity input, and the at least one sensor comprises a brain-computer interface.

48. The method of claim 41 wherein acquiring data of the scanned features comprises confirming that the subject individual is at a maxillomandibular relationship corresponding to a rest position for the subject individual and acquiring data of the face when the maxillomandibular relationship is at the rest position.

49. The method of claim 48 wherein confirming that the subject individual is at a maxillomandibular relationship corresponding to the rest position comprises measuring jaw muscle activity of the subject individual to confirm a maxillomandibular relationship having a minimum energy usage.

50. The method of claim 49 wherein measuring the jaw muscle activity comprises applying electromyography to the subject individual.

51. The method of claim 48 wherein confirming that the subject individual is at a maxillomandibular relationship corresponding to the rest position comprises exhausting jaw muscles of the subject individual.

52. The method of claim 51 wherein exhausting jaw muscles of the subject individual comprises applying transcutaneous electrical nerve stimulation to the jaw muscles.

53. The method of claim 1 wherein data for displaying the 3D model includes data of the face when the maxillomandibular relationship is at the rest position.

54. A system for designing a dental appliance for a subject individual comprising:
   a computer readable medium for storing a 3D model, the 3D model comprising a scanned feature comprising a dental arch of the subject individual and a portion of a face of the subject individual and the arch for relating the arch to the face, and an augmented reality feature comprising a dental appliance for the subject individual; a 3D display for displaying the 3D model;
   at least one sensor for detecting a voluntary input, wherein the voluntary input comprises at least one skilled input from an individual skilled in dental design and at least one layperson input from a layperson individual;
   a processor operatively connected with the computer readable medium for processing the 3D model, with the at least one sensor for detecting the voluntary input, and with the 3D display for displaying the 3D model, the processor configured and adapted to:
   modify the dental appliance in response to the skilled input, the layperson input or both to provide a modified dental appliance;
   reposition the scanned feature in response to the modified dental appliance to provide a repositioned scanned feature;
   update the 3D model in response to the modified dental appliance and the repositioned scanned feature to provide an updated 3D model; and
   display the updated 3D model on the 3D display.

55. The system of claim 54 wherein the at least one sensor comprises a motion sensor for detecting a gesture-based input on the 3D model.

56. The system of claim 54 wherein the at least one sensor comprises a brain-computer interface for detecting a neural activity-based input on the 3D model.

57. The system of claim 54 wherein the at least one sensor comprises a first input point for input from a first individual and a second input point for input from a second individual.

58. The system of claim 54 wherein the at least one sensor comprises an optical sensor for detecting a gesture-based input, a facial-expression-based input, or an ocular dilation-based input.

59. The system of claim 54 further comprising a scanner in communication with the computer readable medium for acquiring data of the scanned feature.

60. The system of claim 59 wherein the scanner comprises an intra-oral scanner for acquiring data of the dental arch.

61. The system of claim 59 wherein the scanner comprises an extraoral scanner for acquiring data of the portion of the face of the subject individual.

62. The system of claim 59 wherein the scanner comprises an optical scanner.

63. The system of claim 59 wherein the scanner comprises an ultrasonographic scanner.

64. The system of claim 59 further comprising a muscle activity sensor for measuring muscle activity of the subject individual's jaw.

65. The system of claim 64 wherein the muscle activity sensor comprises an electromyography module.

66. The system of claim 64 wherein:
the processor is in operative communication with the scanner for causing the scanner to acquire data for modelling the scanned feature; and
the muscle activity sensor is in communication with the processor for directing the scanner to acquire data for modelling the scanned feature when the muscle activity is at a selected value.

67. The system of claim 66 wherein the selected value is indicative of a rest position.

68. A computer readable medium having instructions encoded thereon for:
rendering a 3D model comprising a scanned feature and an augmented reality feature, the scanned feature comprising a dental arch of a subject individual and a portion of a face of the subject individual and the arch for relating the arch to the face, and the augmented reality feature comprising a dental appliance for the subject individual;
detecting a voluntary input from at least one sensor, wherein the voluntary input comprises at least one skilled input from an individual skilled in dental design and at least one layperson input from a layperson individual;
modifying the dental appliance in response to the voluntary skilled input, the layperson input or both to provide a modified dental appliance;
repositioning the scanned feature in response to the modified dental appliance to provide a repositioned scanned feature;
updating the 3D model in response to the modified dental appliance and the repositioned scanned feature to provide an updated 3D model; and
displaying the updated 3D model on a 3D display.

69. The computer readable medium of claim 68 wherein the voluntary input comprises a gesture-based input.

70. The computer readable medium of claim 69 wherein the gesture-based input comprises gripping a feature of the 3D model on the 3D display and manipulating the feature.

71. The computer readable medium of claim 70 wherein gripping the feature comprises gripping the feature with a hand.

72. The computer readable medium of claim 70 wherein the feature comprises dentition of the dental appliance.

73. The computer readable medium of claim 72 wherein manipulating the feature comprises changing angulation of the dentition.

74. The computer readable medium of claim 69 wherein the gesture-based input originates from a first individual.

75. The computer readable medium of claim 69 wherein the gesture-based input originates from a first individual and a second individual.

76. The computer readable medium of claim 69 wherein the at least one sensor comprises a motion sensor.

77. The computer readable medium of claim 68 wherein the voluntary input comprises a neural activity input, and the at least one sensor comprises a brain-computer interface.

78. The computer readable medium of claim 77 wherein the neural activity input comprises a conceptualization of the modified dental appliance.

79. The computer readable medium of claim 77 wherein the neural activity input comprises a conceptualization of modifying the dental appliance.

80. The computer readable medium of claim 79 wherein conceptualization of modifying the dental appliance comprises conceptualizing gripping a feature of the 3D model on the display with a hand and manipulating the feature.

81. The computer readable medium of claim 77 wherein the feature comprises dentition of the dental appliance.

82. The computer readable medium of claim 81 wherein manipulating the feature comprises changing angulation of the dentition.

83. The computer readable medium of claim 77 wherein the voluntary input comprises a gesture-based input, and the at least one sensor comprises a motion sensor.

84. The computer readable medium of claim 77 wherein the neural activity input comprises neural activity input from a first individual.

85. The computer readable medium of claim 77 wherein the neural activity input comprises neural activity input from a first individual and a second individual.

86. The computer readable medium of claim 68 wherein the voluntary input comprises constraining at least a portion of the scanned feature to a target position, and the modified dental appliance comprises a modified feature which facilitates the target position.

87. The computer readable medium of claim 86 wherein the target position comprises a selected maxillomandibular relationship.

88. The computer readable medium of claim 87 wherein the selected maxillomandibular relationship is at a rest position, and the dentition provides a freeway space of between 1 and 4 mm at the rest position.

89. The computer readable medium of claim 87 wherein the selected maxillomandibular relationship is at a selected occlusal position, and the dentition provides occlusion at the selected maxillomandibular relationship.

90. The computer readable medium of claim 87 wherein the modified feature comprises dentition of the dental appliance.

91. The computer readable medium of claim 68, the instructions encoded thereon further comprising:
detecting an involuntary input with the at least one sensor;

modifying the dental appliance in response to the involuntary input to provide the modified dental appliance;

repositioning the scanned feature in response to the modified dental appliance to provide the repositioned scanned feature;

updating the 3D model in response to the modified dental appliance and the repositioned scanned feature to provide the updated 3D model; and displaying the updated 3D model on the 3D display.

92. The computer readable medium of claim 91 wherein the involuntary input comprises involuntary input from a first individual.

93. The computer readable medium of claim 91 wherein the involuntary input comprises involuntary input from a first individual and a second individual.

94. The computer readable medium of claim 91 wherein the involuntary input comprises a neural activity input and the at least one sensor comprises a brain-computer interface.

95. The computer readable medium of claim 68 wherein the involuntary input comprises a change in a facial expression and the at least one sensor comprises an optical sensor.

96. The computer readable medium of claim 68, the instructions encoded thereon further comprising:

detecting an involuntary input from a first individual with the at least one sensor;

correlating the involuntary input with a preference criterion and with the modified dental appliance to determine a preference of the first individual;

modifying the modified dental appliance to provide a suggested dental appliance correlated to the preference of the first individual;

repositioning the scanned feature in response to the suggested dental appliance to provide a suggested scanned feature;

updating the 3D model in response to the suggested dental appliance and suggested scanned feature to provide a suggested 3D model; and displaying the suggested 3D model on the 3D display.

97. The computer readable medium of claim 96 wherein the preference criterion comprises an emotional state of the first individual.

98. The computer readable medium of claim 96 wherein the preference criterion comprises a voluntary input of an individual.

99. The computer readable medium of claim 96 wherein the involuntary input comprises involuntary input from a second individual, and the preference criterion comprises an emotional state of the second individual.

100. The computer readable medium of claim 96 wherein the involuntary input comprises a neural activity input and the at least one sensor comprises a brain-computer interface.

101. The computer readable medium of claim 96 wherein the involuntary input comprises a change a facial expression and the at least one sensor comprises an optical sensor.

102. The computer readable medium of claim 96 wherein the involuntary input is in response to the updated 3D model.

103. The computer readable medium of claim 68 wherein the 3D model comprises a saved position, the saved position having a selected scanned feature of the face.

104. The computer readable medium of claim 103, the instructions encoded thereon further comprising: repositioning the scanned feature to the saved position; updating the 3D model in response to the saved position and repositioned scanned feature to provide a saved position 3D model; and displaying the saved position 3D model on the 3D display.

105. The computer readable medium of claim 68 wherein the scanned feature comprises external feature data of the face for additional detail on the face in the 3D model.

106. The computer readable medium of claim 105 wherein the external feature data of the face comprises data for including substantially the entire face in the 3D model.

107. The computer readable medium of claim 68, the instructions encoded thereon further comprising acquiring data of the scanned feature with a scanner.

108. The computer readable medium of claim 107 wherein acquiring data of the scanned feature comprises optically scanning the scanned feature.

109. The computer readable medium of claim 107 wherein acquiring data of the scanned feature comprises ultrasonographically scanning the scanned feature.

110. The computer readable medium of claim 107 wherein acquiring data of the scanned feature comprises acquiring additional data of the scanned feature in response to the voluntary input and updating the 3D model to include the additional data.

111. The computer readable medium of claim 110 wherein acquiring additional data and updating the 3D model to include the additional data are each performed continuously and substantially in real-time.

112. The computer readable medium of claim 110 wherein adoption of a facial expression by the subject individual results in updating the 3D model to include the additional data, and wherein the additional data includes external feature data of the subject individual adopting the facial expression.

113. The computer readable medium of claim 112 wherein the voluntary input comprises a neural activity input, and the at least one sensor comprises a brain-computer interface.

114. The computer readable medium of claim 107 wherein acquiring data of the scanned features comprises confirming that the subject individual is at a maxillomandibular relationship corresponding to a rest position for the subject individual and acquiring data of the face when the maxillomandibular relationship is at the rest position.

115. The computer readable medium of claim 114 wherein confirming that the subject individual is at a maxillomandibular relationship corresponding to the rest position comprises measuring jaw muscle activity of the subject individual to confirm a maxillomandibular relationship having a minimum energy usage.

116. The computer readable medium of claim 115 wherein measuring the jaw muscle activity comprises applying electromyography to the subject individual.

117. The computer readable medium of claim 114 wherein confirming that the subject individual is at a maxillomandibular relationship corresponding to the rest position comprises exhausting jaw muscles of the subject individual.

118. The computer readable medium of claim 117 wherein exhausting jaw muscles of the subject individual comprises applying transcutaneous electrical nerve stimulation to the jaw muscles.

119. The computer readable medium of claim 68 wherein data for rendering the 3D model includes data of the face when the maxillomandibular relationship is at the rest position.

120. The method of claim 1 wherein the voluntary input originates from at least two individuals.

121. The method of claim 1 wherein detecting the voluntary input comprises detecting the skilled input and the layperson input in a single work session.

122. The method of claim 1 wherein detecting the voluntary input comprises detecting the skilled input in a first work session and detecting the layperson input in a second work session.

123. The method of claim 1 wherein detecting the voluntary input comprises detecting the skilled input and detecting the layperson input from the same network location.

124. The method of claim 1 wherein detecting the voluntary input comprises detecting the skilled input from a first network location and detecting the layperson input from a second network location.

125. The method of claim 1 wherein the at least one sensor comprises at least two sensors, the at least two sensors comprising a first sensor for detecting the skilled input and a second sensor for detecting the layperson input.

126. The method of claim 1 wherein the at least one sensor comprises a single sensor for detecting the skilled input and for detecting the layperson input.

127. The system of claim 54 wherein detecting the voluntary input comprises detecting the skilled input and detecting the layperson input from the same network location.

128. The system of claim 54 wherein detecting the voluntary input comprises detecting the skilled input from a first network location and detecting the layperson input from a second network location.

129. The system of claim 54 wherein the at least one sensor comprises at least two sensors, the at least two sensors comprising a first sensor for detecting the skilled input and a second sensor for detecting the layperson input.

130. The system of claim 54 wherein the at least one sensor comprises a single sensor for detecting the skilled input and for detecting the layperson input.

131. The computer readable medium of claim 68 wherein detecting the voluntary input comprises detecting the skilled input and the layperson input in a single work session.

132. The computer readable medium of claim 68 wherein detecting the voluntary input comprises detecting the skilled input in a first work session and detecting the layperson input in a second work session.

133. The computer readable medium of claim 68 wherein detecting the voluntary input comprises detecting the skilled input and detecting the layperson input from the same network location.

134. The computer readable medium of claim 68 wherein detecting the voluntary input comprises detecting the skilled input from a first network location and detecting the layperson input from a second network location.

135. The computer readable medium of claim 68 wherein the at least one sensor comprises at least two sensors, the at least two sensors comprising a first sensor for detecting the skilled input and a second sensor for detecting the layperson input.

136. The computer readable medium of claim 68 wherein the at least one sensor comprises a single sensor for detecting the skilled input and for detecting the layperson input.

* * * * *